(12) United States Patent
Swerdlow et al.

(10) Patent No.: US 12,257,196 B2
(45) Date of Patent: Mar. 25, 2025

(54) WHEELCHAIR FOR IMPROVED MUSCULAR SKELETAL SYSTEM ALIGNMENT

(71) Applicant: Aligned As Designed, LLC, Los Angeles, CA (US)

(72) Inventors: Linda Smith Swerdlow, Los Angeles, CA (US); Henning Zieger, Los Angeles, CA (US)

(*) Notice: Subject to any disclaimer, the term of this patent is extended or adjusted under 35 U.S.C. 154(b) by 642 days.

(21) Appl. No.: 17/437,011

(22) PCT Filed: Mar. 6, 2020

(86) PCT No.: PCT/US2020/021492
§ 371 (c)(1),
(2) Date: Sep. 7, 2021

(87) PCT Pub. No.: WO2020/181233
PCT Pub. Date: Sep. 10, 2020

(65) Prior Publication Data
US 2022/0175595 A1   Jun. 9, 2022

Related U.S. Application Data

(60) Provisional application No. 62/814,662, filed on Mar. 6, 2019.

(51) Int. Cl.
*A61G 5/02* (2006.01)
*A61G 5/08* (2006.01)
(Continued)

(52) U.S. Cl.
CPC ............. *A61G 5/026* (2013.01); *A61G 5/025* (2013.01); *A61G 5/0808* (2016.11);
(Continued)

(58) Field of Classification Search
CPC ...... A61G 5/026; A61G 5/0808; A61G 5/121; A61G 5/128; A61G 5/025; A61G 5/1037; A61G 2210/10
See application file for complete search history.

(56) References Cited

U.S. PATENT DOCUMENTS 3,666,292 A  5/1972  Bartos
4,274,651 A  6/1981  Dumont
(Continued)

OTHER PUBLICATIONS

PCT International Search Report for PCT/US2020/021492, mailed Jul. 17, 2020, 3 pages.
(Continued)

*Primary Examiner* — Kevin Hurley
*Assistant Examiner* — Michael R Stabley
(74) *Attorney, Agent, or Firm* — Husch Blackwell LLP

(57) ABSTRACT

A wheelchair configured to impart motion on one or more lower extremities of a user to inhibit inelasticity in joints of one or more lower extremities as a result of extended immobility, and to promote a more natural alignment of one or more upper extremities of the user during manipulation of the wheelchair. The wheelchair includes a seat and a backrest, at least two ground-engaging wheels, a hand mechanism assembly including a hand grip on each side of the wheelchair, and a foot mechanism assembly including a footrest on each of the wheelchair. When a force is applied to one of the hand grips, the wheels rotate for locomotion, and the foot mechanism assembly is actuated, causing the foot rest on the opposite side from the hand grip to move in an arced path, and vice versa, thereby imparting contralateral locomotion.

19 Claims, 46 Drawing Sheets

(51) Int. Cl.
*A61G 5/10* (2006.01)
*A61G 5/12* (2006.01)

(52) U.S. Cl.
CPC ........... *A61G 5/1037* (2013.01); *A61G 5/121* (2016.11); *A61G 5/128* (2016.11); *A61G 2210/10* (2013.01)

(56) References Cited

U.S. PATENT DOCUMENTS

| | | | |
|---|---|---|---|
| 5,242,179 A | | 9/1993 | Beddome et al. |
| 5,272,928 A | | 12/1993 | Young |
| 5,322,312 A | | 6/1994 | Cammack |
| 5,499,833 A | * | 3/1996 | Her .................. A61G 5/025 280/247 |
| 6,158,757 A | * | 12/2000 | Tidcomb .............. A61G 5/025 403/325 |
| 6,234,504 B1 | * | 5/2001 | Taylor ................ A61G 5/023 280/DIG. 10 |
| 6,648,354 B2 | * | 11/2003 | James ................ A61G 5/128 280/255 |
| 9,597,241 B2 | * | 3/2017 | Zondervan ........... A61G 5/024 |
| 10,124,666 B2 | * | 11/2018 | Cunningham ......... A61G 5/025 |
| 10,940,063 B2 | * | 3/2021 | Eason ................ A61G 5/1008 |
| 2010/0007114 A1 | * | 1/2010 | Papi .................. A61G 5/028 280/281.1 |

OTHER PUBLICATIONS

PCT Written Opinion of the ISA for PCT/US2020/021492, mailed Jul. 17, 2020, 5 pages.

\* cited by examiner

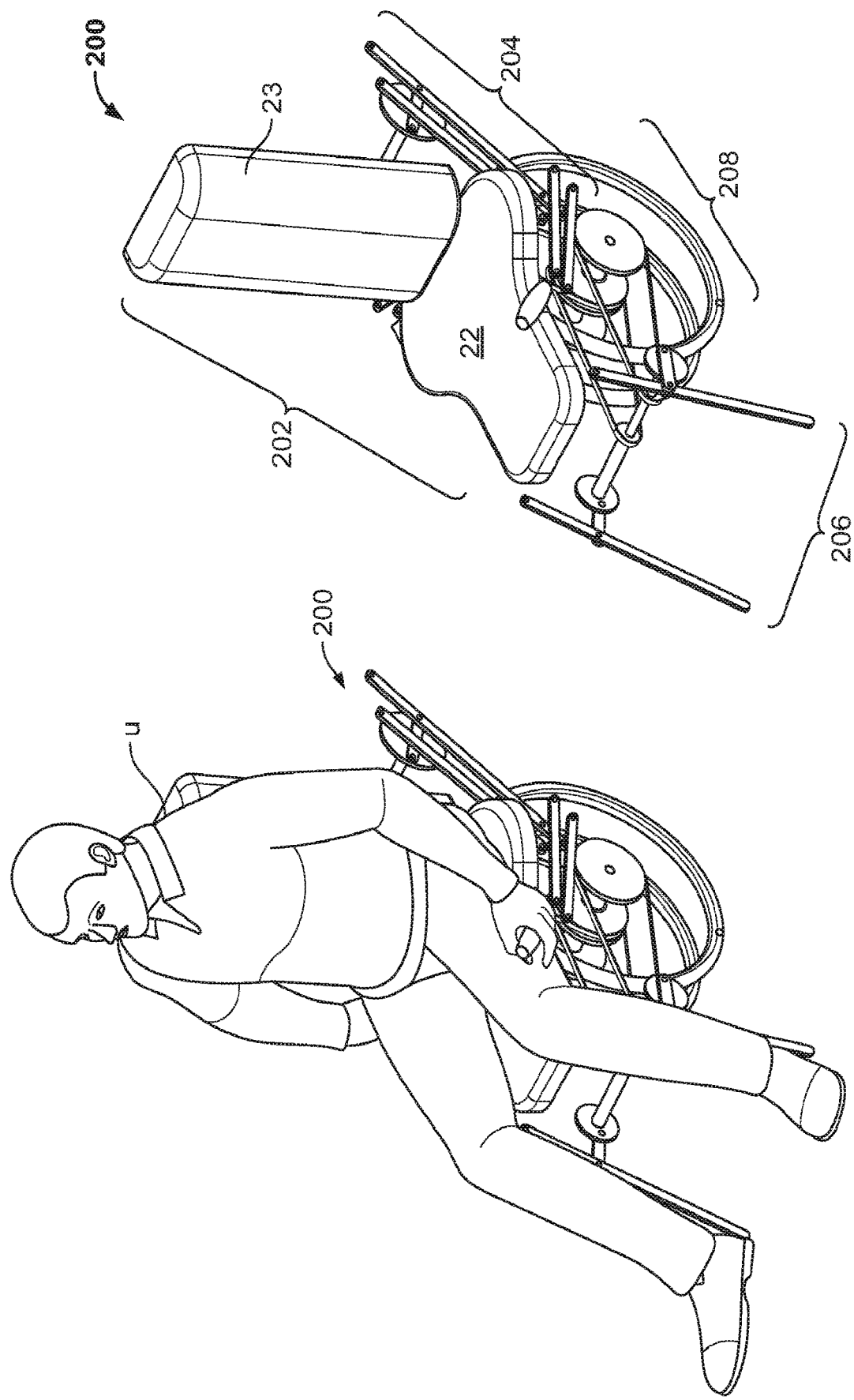

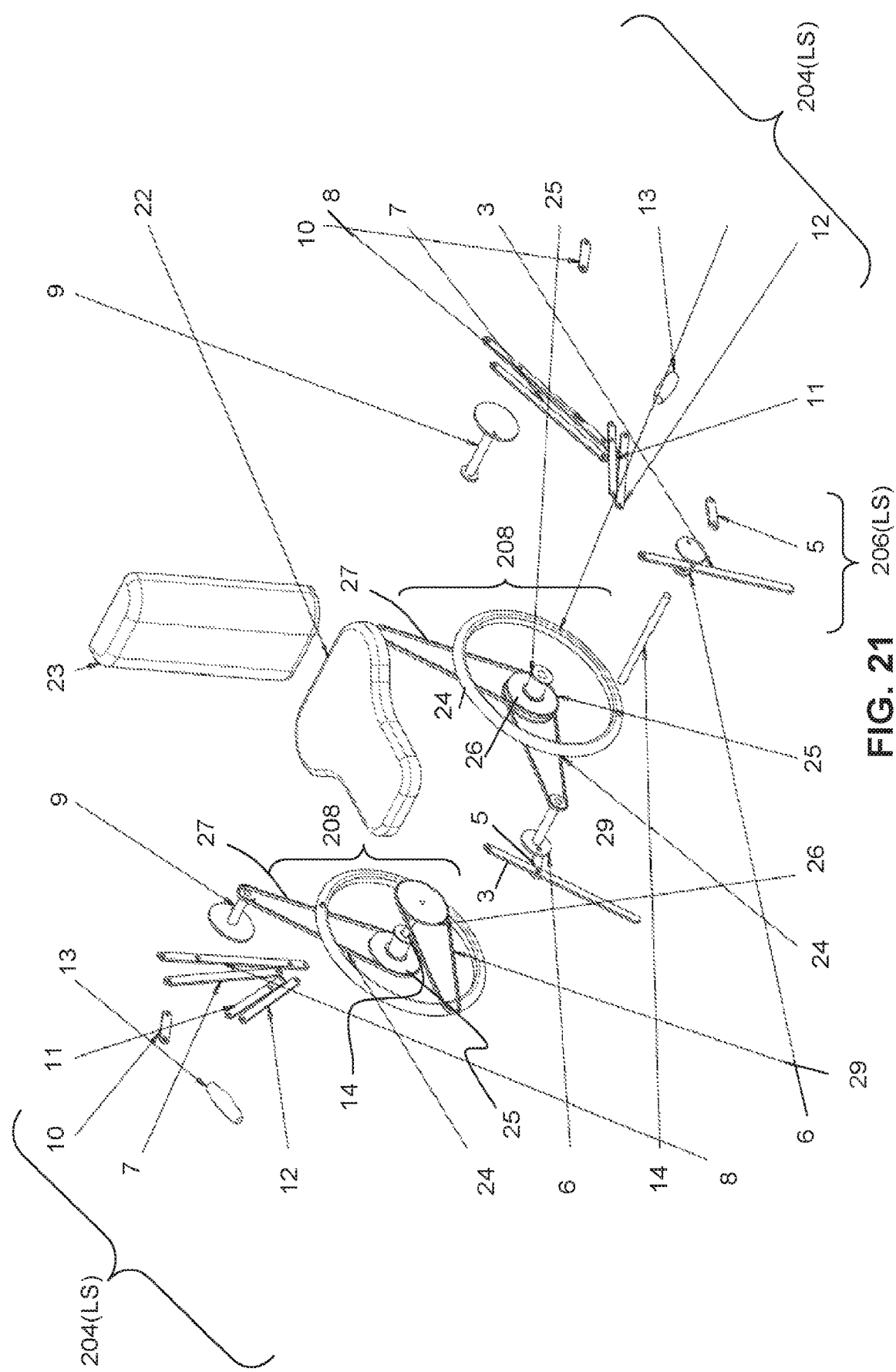

FIG. 22A
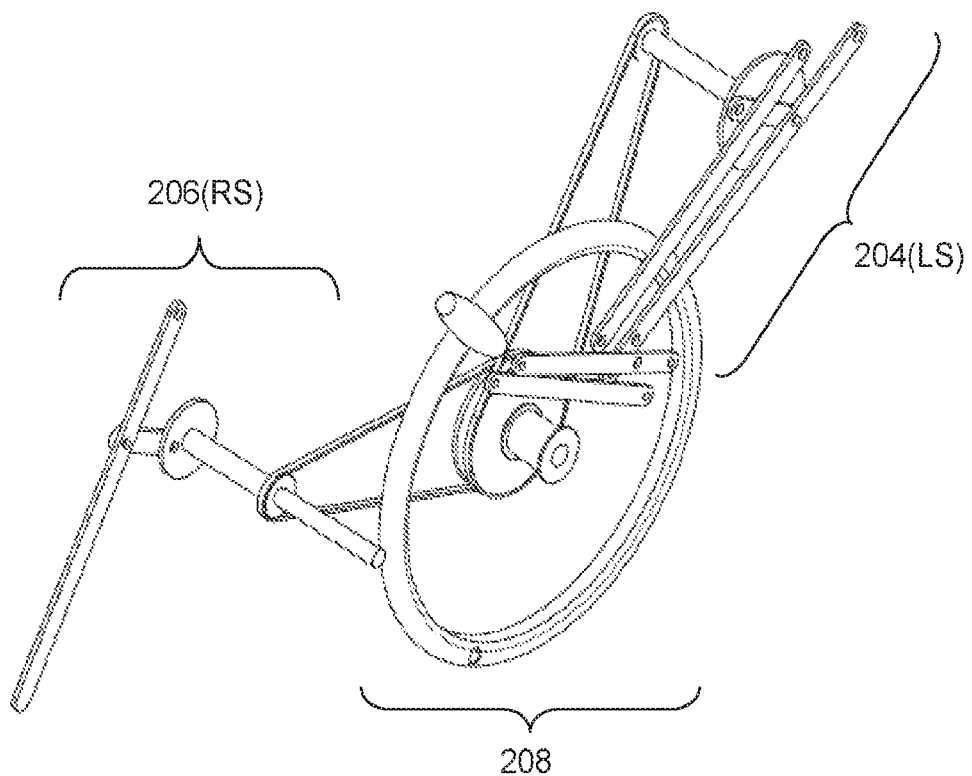
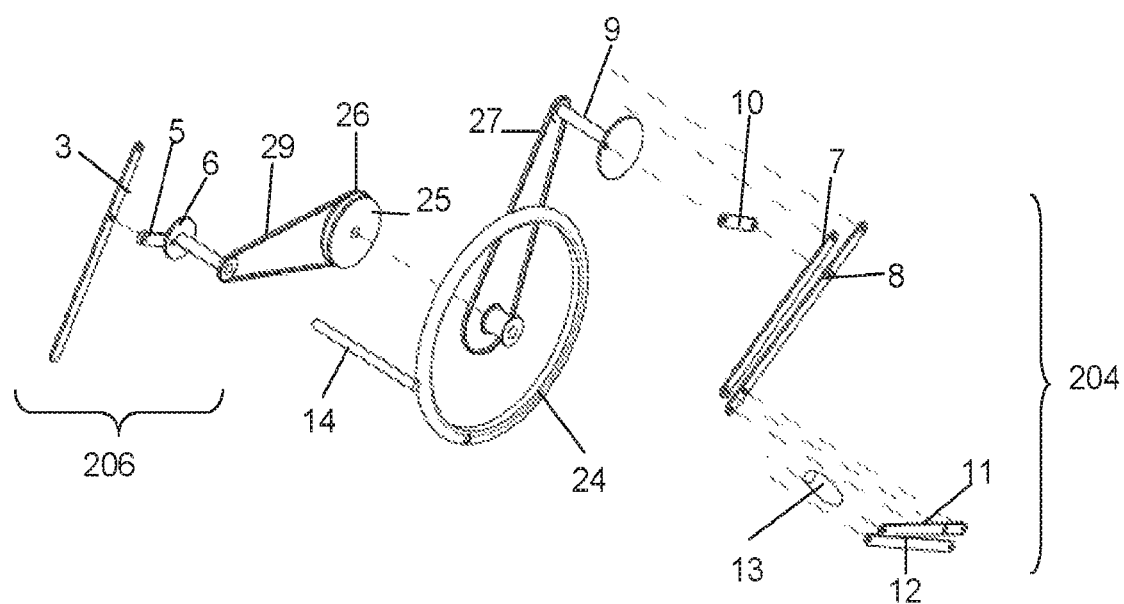
FIG. 22B

FIG. 23
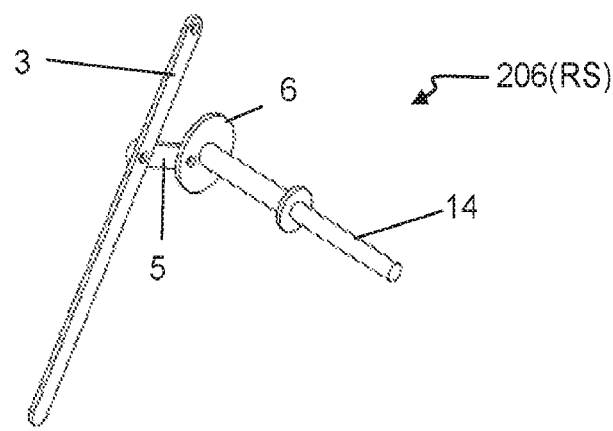
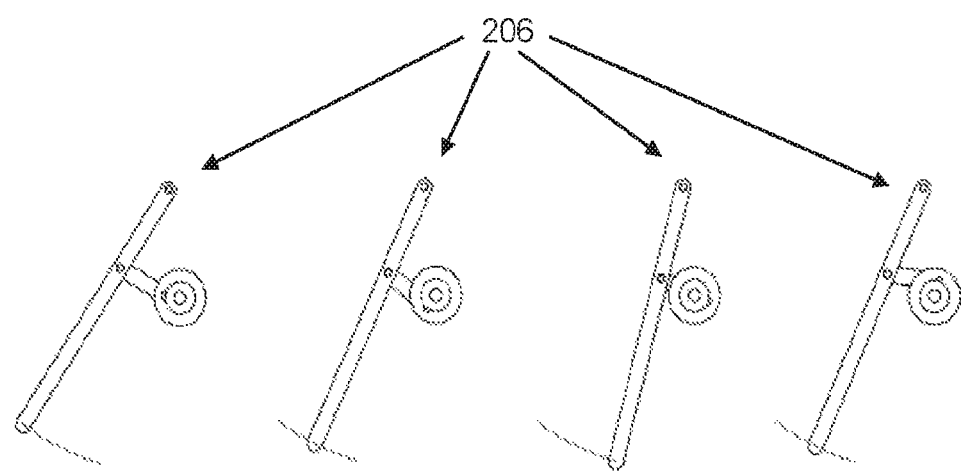
FIG. 24

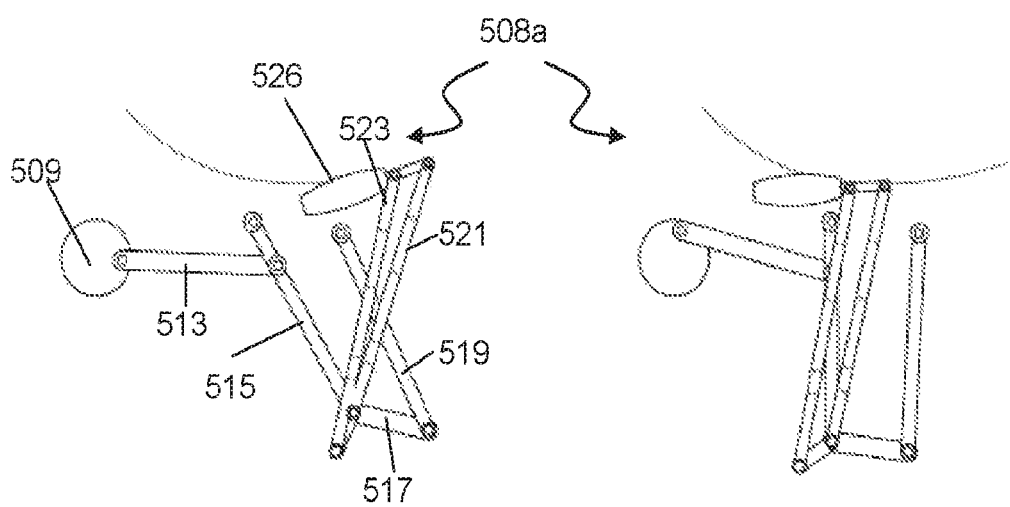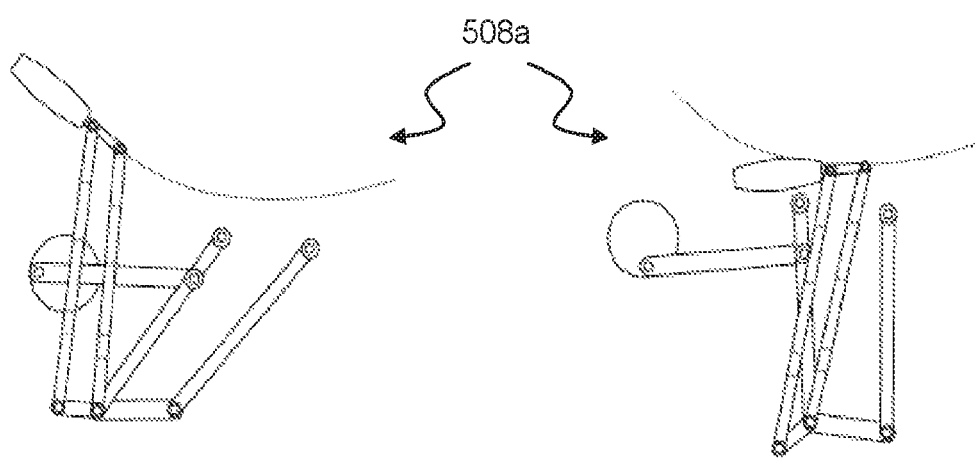
FIG. 36

FIG. 38A
FIG. 38B
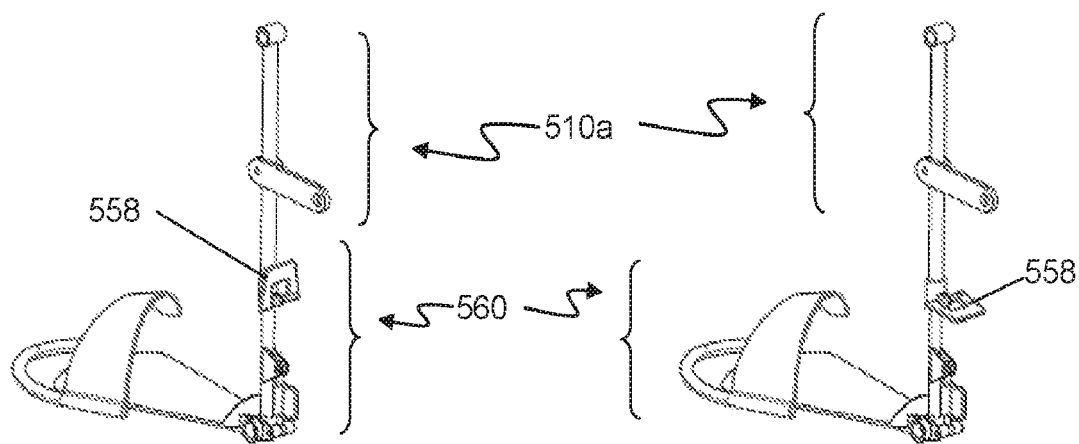
FIG. 38C
FIG. 38D
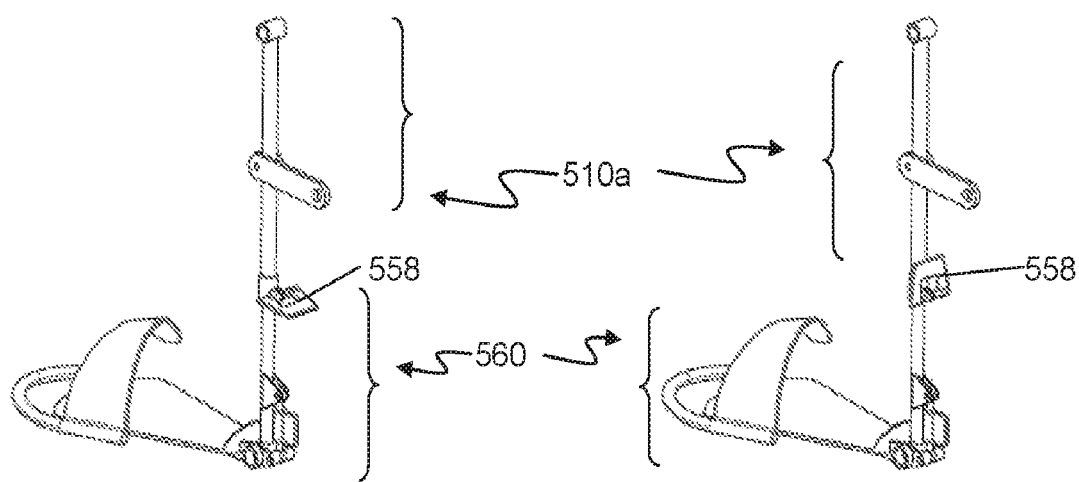

FIG. 42A
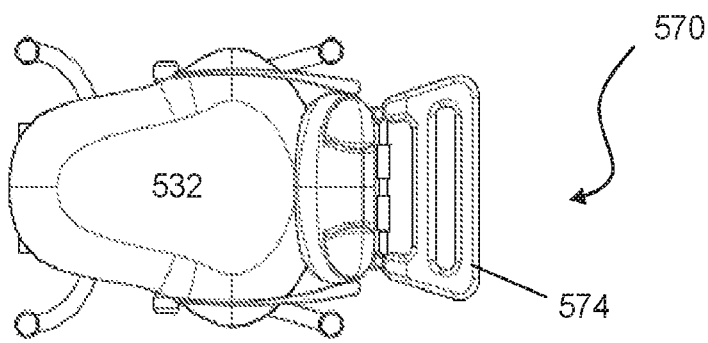
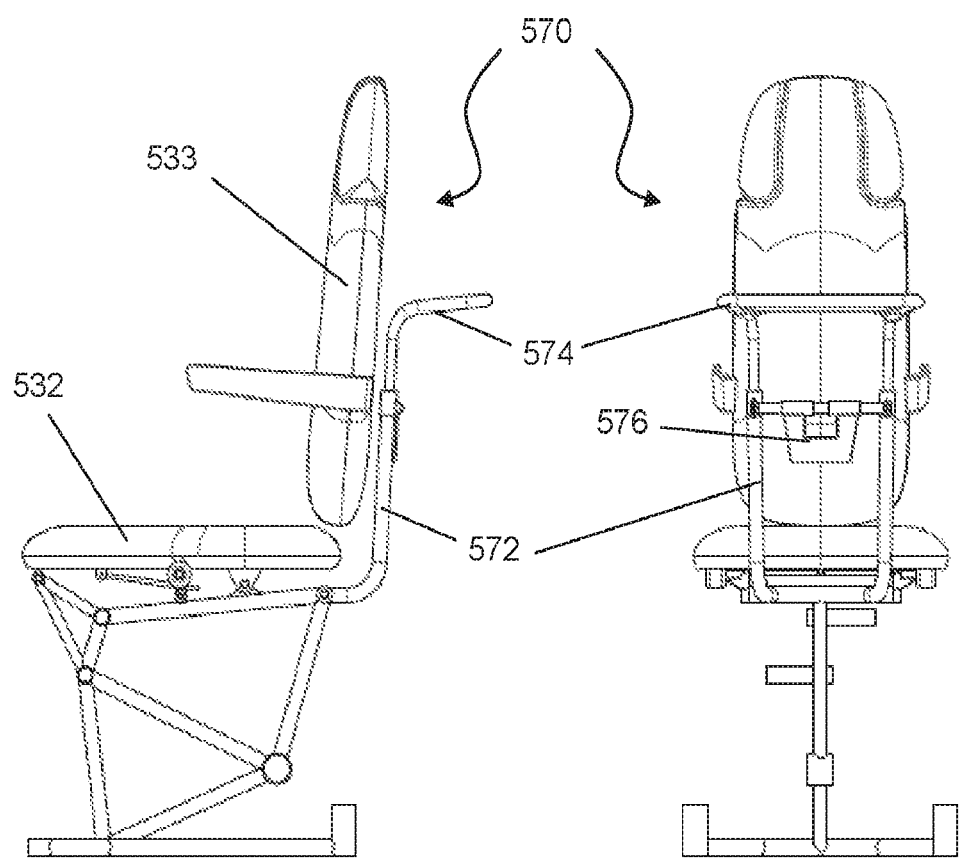
FIG. 42B  FIG. 42C

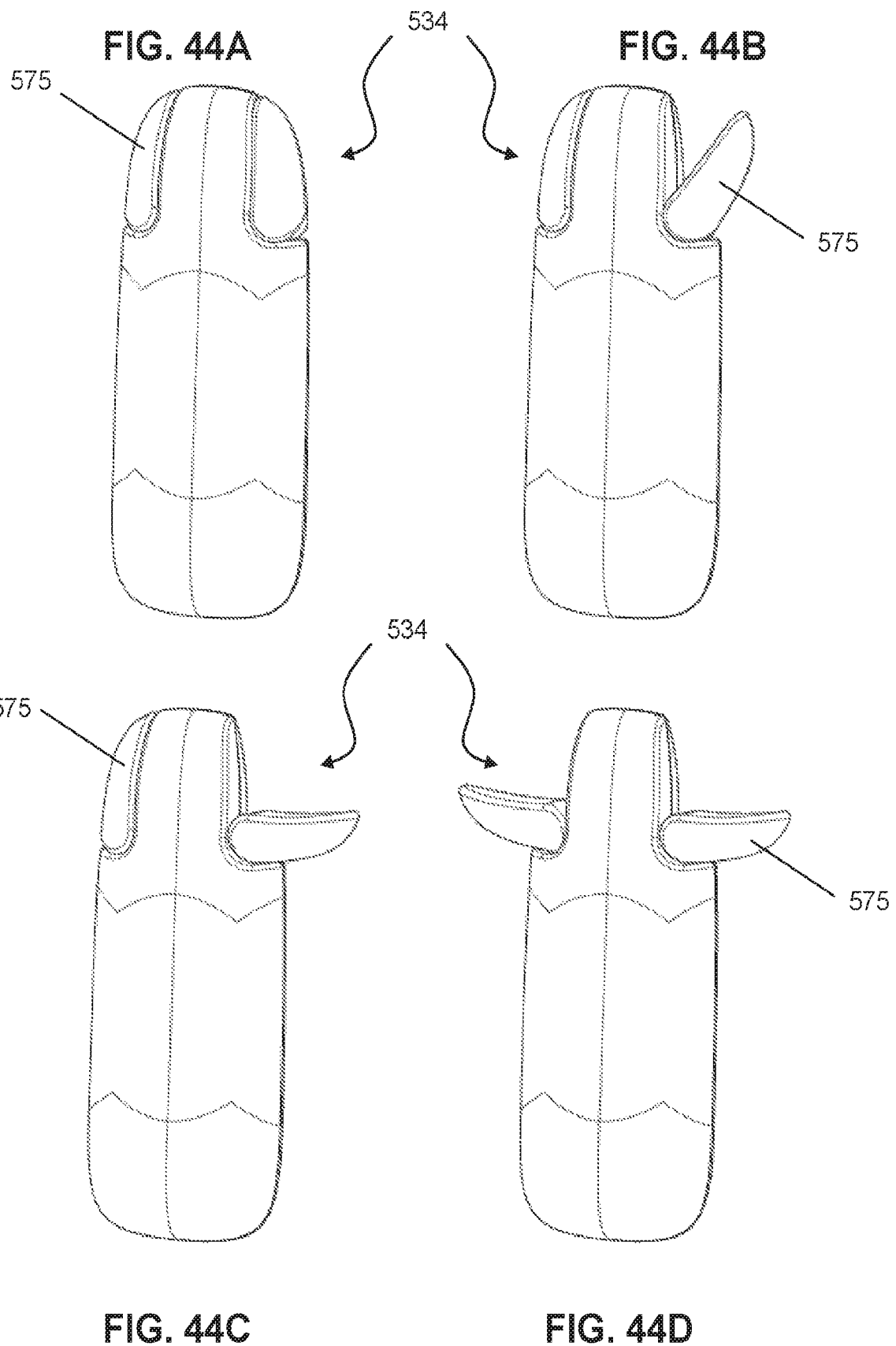

FIG. 45A
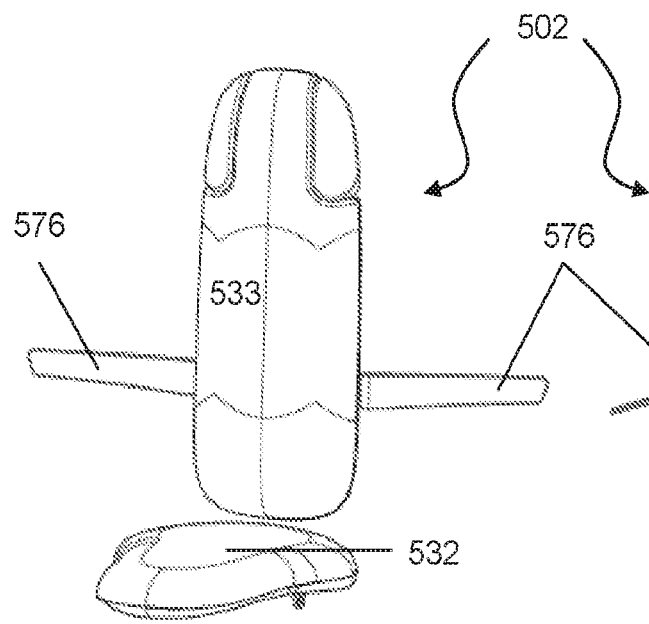
FIG. 45B
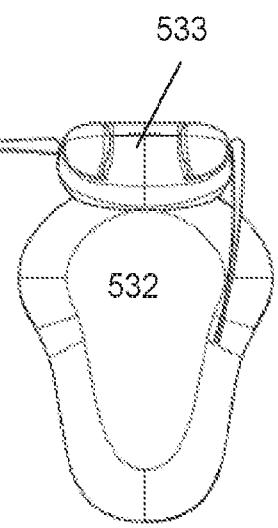
FIG. 45C
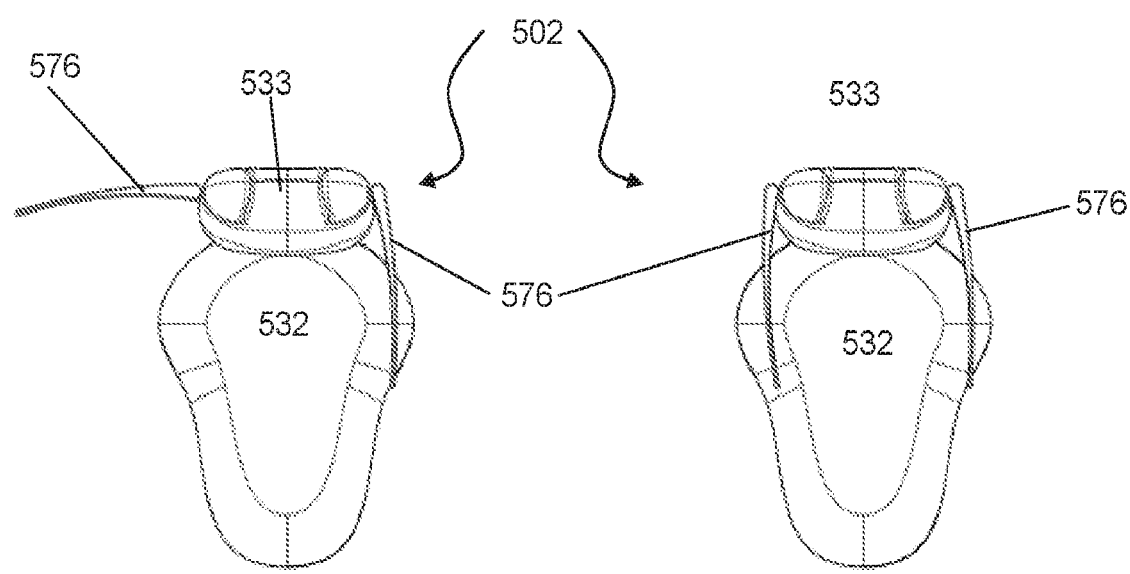
FIG. 45D

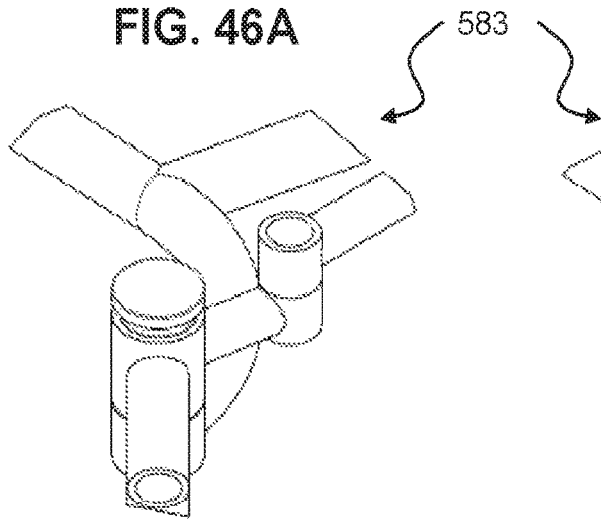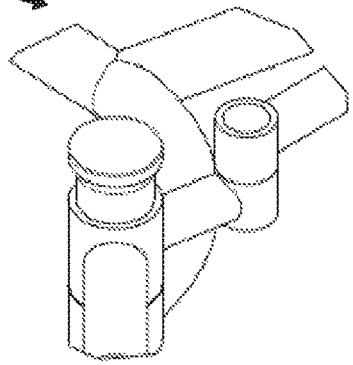
FIG. 46A  FIG. 46B
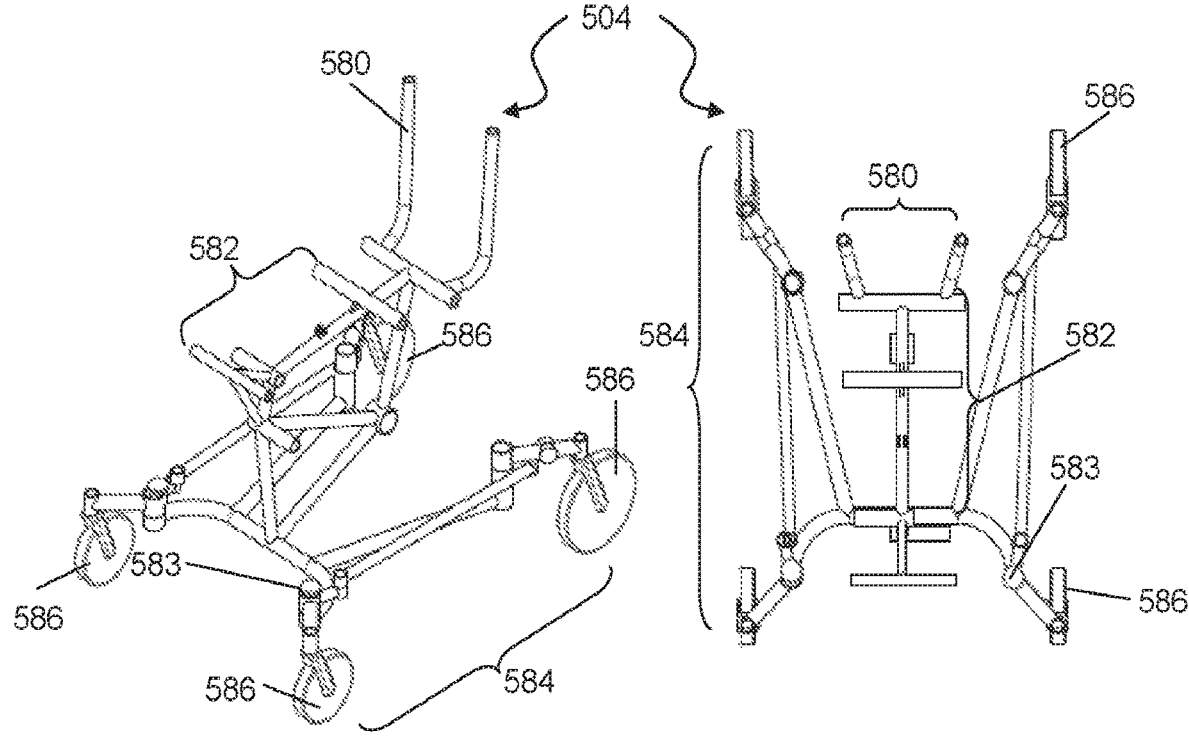
FIG. 47A  FIG. 47B

FIG. 47C
FIG. 47D
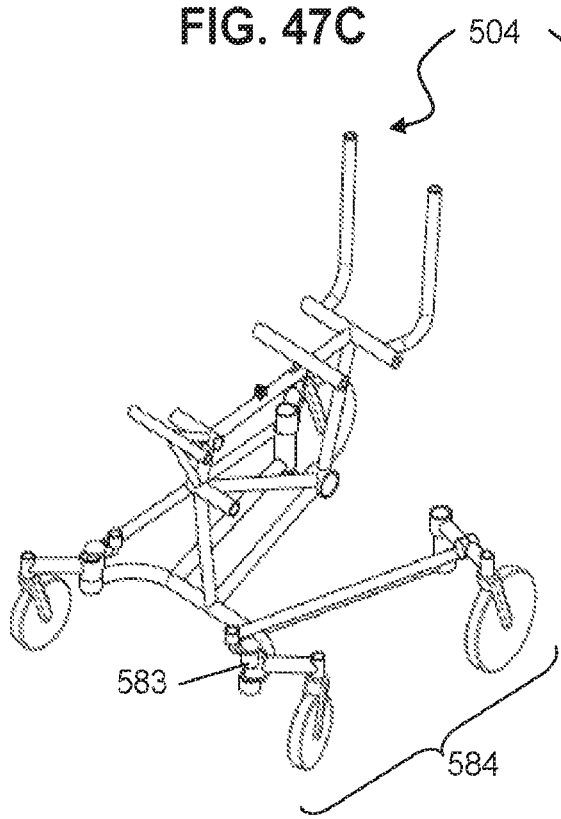
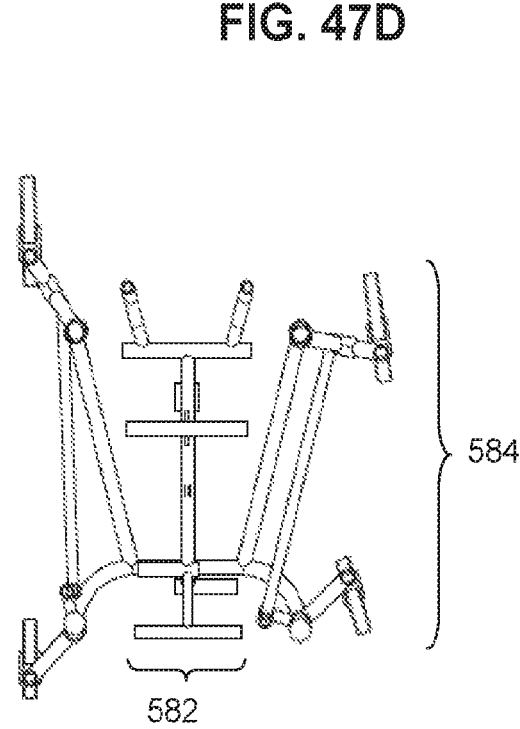
FIG. 47E
FIG. 47F
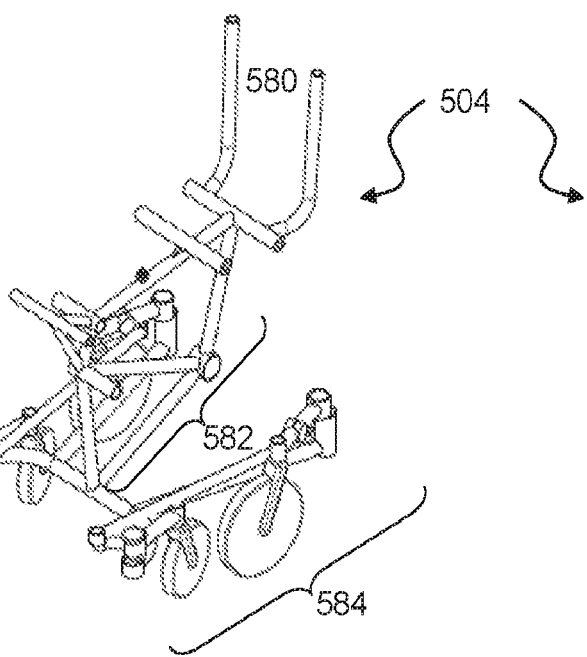
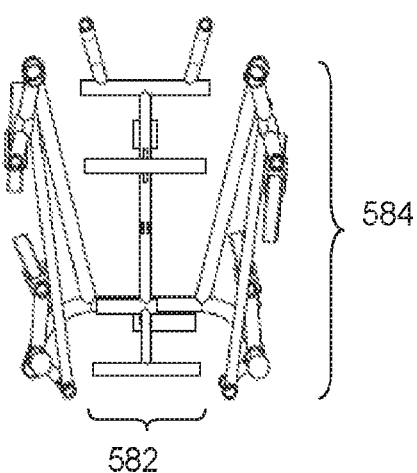

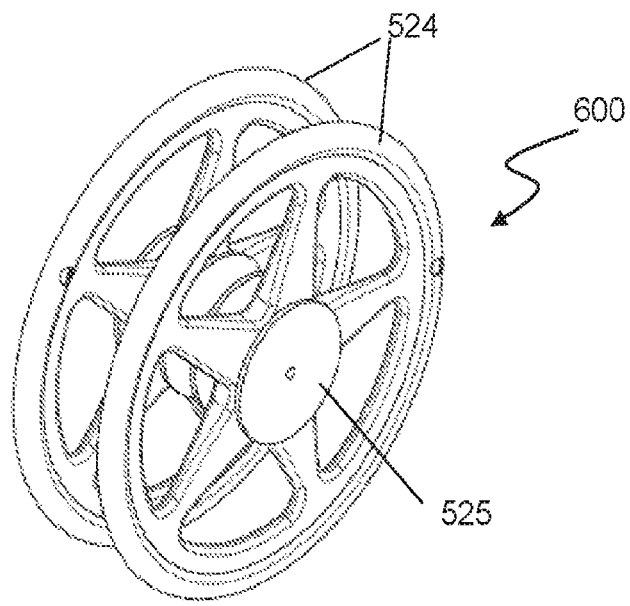
FIG. 49A
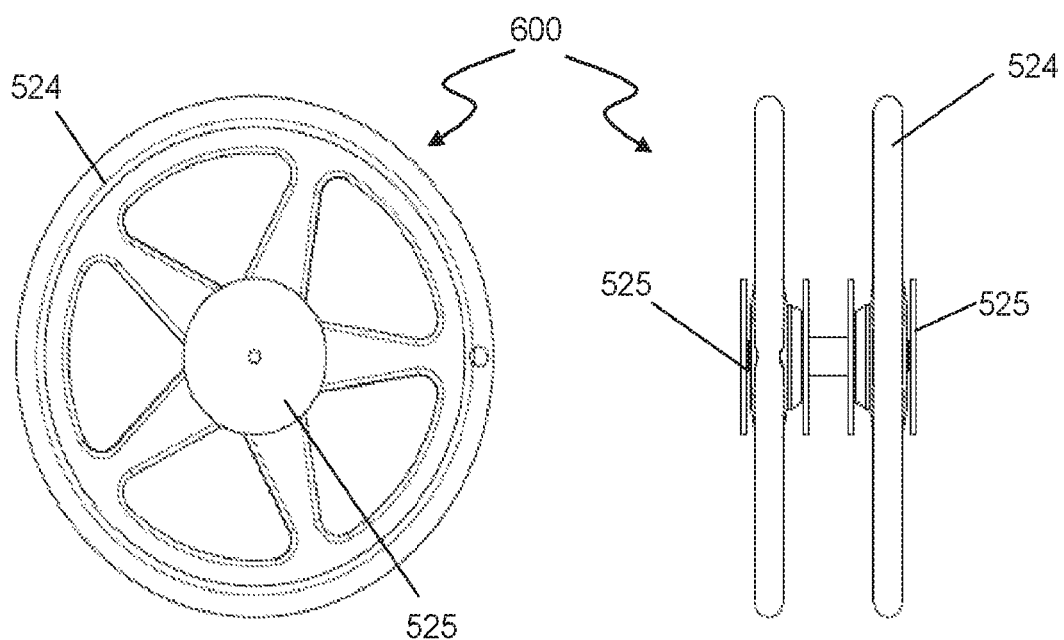
FIG. 49B
FIG. 49C

WHEELCHAIR FOR IMPROVED MUSCULAR SKELETAL SYSTEM ALIGNMENT

RELATED APPLICATIONS

The present application is a National Phase entry of PCT Application No. PCT/US2020/021492, filed Mar. 6, 2020, which claims the benefit of U.S. Provisional Application No. 62/814,662 filed Mar. 6, 2019, all of these disclosures being hereby incorporated herein by reference in their entirety.

TECHNICAL FIELD

The present disclosure relates generally to wheelchairs, and more particularly to wheelchairs configured to improve the muscular skeletal system alignment of users and to impart a linear, arcing, or swinging motion to a lower extremity of users to inhibit inelasticity of joints as a result of extended immobility, and instead promotes elasticity of joints.

BACKGROUND

Subjects with Spinal Cord Injuries (SCI) and other lower extremity injuries frequently utilize a wheelchair for the completion of acts of daily living and improved mobility. Traditional wheelchairs, such as that depicted in U.S. Pat. No. 3,282,605, the contents of which are hereby incorporated by reference herein to the extent that they do not contradict the teachings herein, typically include a chair frame including a seat and back operably coupled to a pair of large diameter primary ground engaging wheels for locomotion, as well as a pair of smaller diameter wheels adjacent to one or more optional footrests to create a four point base of stability.

Unfortunately, due to placement and positioning of the primary wheels of traditional wheelchairs, during locomotion a user must continually bend and extend their arms outwardly and away from the body's natural Center of Mass (COM), Center of Gravity (COG) and Base of Support (BOS). In particular, manual rotation of the primary wheels causes continuous, repetitive motion that bends and hyper-extends the elbows, wrists and shoulder joints away from the body's COG and BOS. As such, the shoulder joints lose vertical alignment and orientation with the shoulder girdle as they rotate down and forward. The pectoral girdle becomes anterior to the pelvic girdle, the cervical spine straightens as the user's head is thrust forward, and the chin rotates forward towards the chest on each rotation of the wheels, which in turn results in a reduced visual field of view. Further, locomotion of traditional wheelchairs, even those with extended rims or rails, require a user to repeatedly grasp a portion of the primary ground engaging wheels, thereby continuously exposing the user to dirt, water and debris. Meanwhile, the lower extremities of the user remain motionless.

When the muscles, tendons and ligaments of the legs and feet stop moving, less than adequate levels of synovial fluid are produced. As a result, the facia surrounding the bones and the tendons of the legs and feet constrict, thereby decreasing the subject's flexibility. The lack of lower body movement during traditional wheelchair use also causes an increase of the fat to muscle ratio of the body, which can lead to an increased risk of developing diabetes and heart disease. Spasticity leg contractions brought on by prolonged immobility are also common among wheelchair users.

The present disclosure addresses these concerns.

SUMMARY OF THE DISCLOSURE

Embodiments of the present disclosure provide a wheelchair in which a user's arms are more naturally aligned with the body's COM, COG and BOS during locomotion. Contralateral movement of the peripheral joints of the body maintains the structural integrity and alignment of the entire muscular system, as well as the afferent and efferent pathways of the central nervous system and peripheral nervous system. The user's head remains positioned over their body, and their line of sight remains fixed in the direction of locomotion (instead of the ground), which allows for a more natural curve of the spine as well as an improved field-of-view.

Additionally, embodiments of the present disclosure provide a wheelchair having footrests configured to move the user's lower extremities during locomotion, which results in less contraction of the Achilles tendons and facia of the feet and legs. In particular, embodiments of the present disclosure can include footrests operably coupled to an off-center axis of one or more ground engaging wheels, such that each rotation of a control wheel about a central axis causes a corresponding movement of a footrest on the opposite side of the wheelchair. The motion of the footrests can be circular, elliptical, linear, or any shape that promotes a more natural muscle stretching and joint articulation in the legs and feet of the user. In some embodiments, the foot rests can be weighted to aid the user in maintaining the heels of their feet lower than their toes during locomotion.

The human body is a biological movement machine designed to maintain a balanced COM and COG inside the body's natural BOS. Skeletal bones of the body form the framework, with ligaments attaching bone to bone to form articulating joints. Skeletal muscles move the framework, with tendons attaching the skeletal muscles to the skeletal bones, and facia surrounding the bones, ligaments and tendons. Together the skeletal bones, ligaments, skeletal muscles, tendons, and facia cooperate to maintain postural alignment of the body. Locomotion that keeps the joints aligned inside the body's natural BOS, also keeps the skeletal muscles and facia strong and flexible and helps the body to produce synovial fluid, which serves to lubricate the joints, absorb shock, reduce friction, bring essential nutrients to the joints, and remove carbon dioxide and metabolic waste from the joints. In particular, of the thirty-three joints in the human foot, twenty are synovial joints, which have no blood supply of their own and rely on movement from surrounding bone and tissue to produce synovial fluid.

When the body loses its ability to use the lower extremities in ambulation, the lack of motion of the legs and feet can have devastating long-term effects to the bones, muscles, ligaments, tendons and facia of the musculoskeletal system of the entire body. In particular, the lack of motion results in less than adequate levels of synovial fluid production, which in turn results in the facia surrounding the bones and the tendons of the legs and feet to constrict in a manner that decreases the subject's flexibility. Additionally, muscle loss and atrophy typically begins within a few days following a loss of the ability to use the lower extremities. Physical therapy several times a week will slow the devastating loss to the bones, muscles, ligaments, tendons, and facia, but will not stop the atrophy and decreased flexibility without daily movement of all four limbs. The lack of lower body movement during traditional wheelchair use also causes an increase of the fat to muscle ratio of the body, which can lead to an increased risk of developing diabetes and heart disease. Spasticity leg contractions brought on by prolonged immobility are also common among wheelchair users.

The stability of the body during locomotion depends on the gravitational balance and stability of the arms and legs. Injury or movement of a joint outside of the body's natural BOS creates under loading or overloading to all other joints. Under loading or overloading of a joint, or movement that causes hyperextension of a joint or its supporting tissue can result in a loss of physical stability and postural alignment. Over time, repetitive movement that does not maintain the body's COM and COG over its natural BOS will result in physical and functional disability that is unrelated to the initial injury.

Wolff's Law states that bone function changes cause bone structure modification. Davis's Law states that the tendency of soft tissue is to shorten and contract unless it is subject to frequent stretching; "nature never wastes her time and material in maintaining a muscle or ligament at its original length when the distance between their points of origin and insertion is for any considerable time, without interruption, shortened" To quote Dr. Davis, "[u]se it or lose it." The SAID Principle (specific adaptation to imposed demands) states that the body will gradually adapt to stresses and overloads that it is subjected to. Hook's Law states that tissue strain is directly proportional to apply compressive or stretching stress, so long as the tissue elasticity is not exceeded. Accordingly, repetitive motion that bends and hyper-extends the elbows, wrists and shoulder joints away from the body's natural BOS (e.g., during manipulation of the wheels of a traditional wheelchair) can cause long-term negative effects as the body adapts to the stresses and overloads that it is subjected to.

Repetitive motion that forces the joints outside of the body's natural BOS can also negatively affect the body's central nervous system and peripheral nervous system. The levers or skeletal bones and the fulcrums or joints create movement using afferent efferent neuron impulses. Afferent sensory neurons throughout the body receive information from the eyes and skin and carry that information via pathways to the central nervous system. The efferent neurons carry motor impulses from the brain to the spinal cord via inter-neurons. Each movement that a subject or person takes reinforces and determines the quality and quantity of the movement and information that their body and brain receive. People create functional and physical ability or disability with each movement they take. When a person is injured or engages in motor behavior that stops them from being aligned with the body's COM, COG and BOS, the afferent efferent interneuron highway that determines how we move and the way we move is negatively affected.

Voluntary movement is a result of muscles in the central nervous system working together. The cerebral cortex creates the body's voluntary movement using muscle contraction. The basal ganglia controls and maintains posture and equilibrium during movement. The cerebellum integrates sensory impulses in motor information. The peripheral nervous system, the central nervous system, and the spinal cord form motor pathways of the body. The body can grow more neurons and create more motor pathways throughout life. New pathways are created through movement. Continuous movement that keeps the body from being naturally aligned rewrites the afferent efferent pathways of the body for physical and functional disability. To change or improve damaged or broken motor behavior, the body needs to have continuous repetitive motion that reinforces and improves the afferent efferent message of the body's natural pathways.

One embodiment of the present disclosure provides a wheelchair configured to impart a translational or linear motion (such as swinging or arcing motion) on one or more lower extremities of the user to inhibit inelasticity of joints of the one or more lower extremities as a result of extended immobility, and to provide a natural alignment of one or more upper extremities of the user during manipulation of the wheelchair. The wheelchair can include a frame having a seat, the seat being movable from a horizontal position to one or more inclined positions to aid a user in moving into and out of the wheelchair and to adequately support the spine, a forward set of ground engaging wheels operably coupled to the frame, a rearward set of ground engaging wheels operably coupled to the frame, a set of control wheels operably coupled to the frame and positioned below the seat at a distance configured to promote a natural alignment of the one or more upper extremities of the user during manipulation of the set of control wheels, each control will of the set of control wheels configured to drive a corresponding one wheel of at least one of the forward set of ground engaging wheels and a rear set of ground engaging wheels, and a pair of footrests operably coupled to the forward set of ground engaging wheels, wherein rotation of each wheel of the forward set of ground engaging wheels imparts a corresponding arcing, linear or swinging motion of each foot rest of the pair of footrests, so as to impart motion on the one or more lower extremities of the user to inhibit in elasticity in the joints of the one or more lower extremities as a result of extended immobility.

In one particular embodiment, when a user engages a control wheel on a first side of the wheelchair, it drives a corresponding ground engaging wheel (either on the same side or opposite side) to impart motion on a footrest on an opposite side of the wheelchair, such that the motion mimics the contra lateral movement associated with walking. In a specific configuration, a user's lower arm and hand are in a most rearward position during the linear or swinging motion, e.g. behind a user's torso or spine, when the opposite foot is in a most forward extended position in the foot rest.

In another embodiment of the disclosure, a wheelchair is configured to impart motion on one or more lower extremities of a user to inhibit inelasticity in joints of the one or more lower extremities as a result of extended immobility, and to promote a natural alignment of one or more upper extremities of the user during manipulation of the wheelchair. The wheelchair can comprise, for example, a seat assembly comprising a seat and a backrest, at least two ground-engaging wheels, a hub assembly including a first drive-wheel and a first chain, and a second drive-wheel and a second chain, the first drive-wheel being operably coupled to the second drive-wheel, a hand mechanism assembly including a first arm drive-wheel operably coupled to the first drive-wheel via the first chain, the first arm drive-wheel being configured to be operated using a first upper extremity of a user, and a foot mechanism assembly including a first leg drive-wheel operably coupled to the second drive-wheel via the second chain, the first leg drive-wheel being configured to impart motion of a first lower extremity of the user on a side opposite the first upper extremity used to operate the hand mechanism assembly. The wheelchair is configured such that actuation of the first arm drive-wheel of hand mechanism assembly by the upper extremity actuates the first leg drive-wheel of the foot mechanism assembly to impart the motion on the first lower extremity, and causes at least one of the ground-engaging wheels to rotate, thereby resulting in contralateral locomotion.

In this embodiment, rotation of the first arm drive-wheel by one of a right hand or a left hand of the user actuates the first leg drive-wheel of the foot mechanism assembly to impart motion of the other of a right leg or left leg of the user. The foot mechanism assembly can further comprise a footrest operably coupled to the first leg drive-wheel, and wherein rotation of the first leg drive-wheel imparts one of a linear or arcing motion on the footrest, thereby allowing the lower extremity of the user to swing back and forth.

In this embodiment, the hand mechanism assembly can further comprise a linkage fixedly coupled to the first arm drive-wheel, at least one elongate grip link pivotably coupled at a first end, either directly or indirectly, the first linkage, and a grip coupled to a second end of one of the at least one elongate grip links, the grip being configured to be moved when force is applied thereto by the first upper extremity of the user. The linkage converts translational movement of the grip into rotational movement of the first arm drive-wheel.

In this embodiment, the leg mechanism assembly further comprises a linkage fixedly coupled to the first leg drive-wheel, a leg link coupled to the second linkage at a first end, and a foot rest coupled to a second end of the leg link. The linkage converts rotational movement of the first leg drive-wheel into translational movement of the leg link and foot rest.

In an embodiment, the hub assembly can further comprise a third drive-wheel and a third chain, and a fourth drive-wheel and a fourth chain, the third drive-wheel being operably coupled to the fourth drive-wheel. The hand mechanism assembly further comprises a second arm drive-wheel operably coupled to the third drive-wheel via the third chain, the second arm drive-wheel being configured to be operated using a second upper extremity of a user on a side opposite the first upper extremity. The foot mechanism assembly further comprises a second leg drive-wheel operably coupled to the fourth drive-wheel via the fourth chain, the second leg drive-wheel being configured to impart motion of a second lower extremity of the user on a side opposite the second upper extremity used to operate the hand mechanism assembly. The wheelchair is further configured such that actuation of the second arm drive-wheel of the hand mechanism assembly by the second upper extremity actuates the second leg drive-wheel of the foot mechanism assembly to impart the motion on the second lower extremity, and causes the other of the at least one of the ground-engaging wheels to rotate, thereby resulting in contralateral locomotion. This motion mimics the contralateral motion of walking.

In this embodiment, the hand mechanism assembly can further comprise a third linkage fixedly coupled to the second arm drive-wheel, at least one elongate grip link pivotably coupled at a first end, either directly or indirectly, to the third linkage, and a grip coupled to a second end of one of the at least one elongate grip links, the grip being configured to be moved when force is applied thereto by the second upper extremity of the user. This linkage also converts translational movement of the grip into rotational movement of the second arm drive-wheel. Similarly, the leg mechanism assembly can further comprise a linkage fixed coupled to the second leg drive-wheel, a leg link coupled to the fourth linkage at a first end, and a foot rest coupled to a second end of the leg link. This linkage converts rotational movement of the second leg drive-wheel into translational movement of the leg link and foot rest.

In embodiments, the first drive-wheel of the hub assembly is fixedly coupled to a first end of a first axel, and the second drive-wheel is fixedly coupled to a second end of the axel, thereby defining an inner hub. The third drive-wheel of the hub assembly is fixedly coupled to a first end of a second axel, and the fourth drive-wheel is fixedly coupled to a second end of the second axel, thereby defining an outer hub. The outer hub is operably coupled to the inner hub such that the second axel covers a portion of the first axel of the inner hub, and the third and forth drive-wheels are positioned between the first and second drive-wheels.

In embodiments, the inner hub is operably coupled to the outer hub via a clutch drive positioned radially over the axel of the inner hub, and between the axels. The clutch drive is configured to engage the inner hub and outer hub to rotate both simultaneously, and configured to disengage the inner hub from the outer hub for independent rotation. In an embodiment, a portion of the outer surface of the clutch drive includes structure thereon defining a thread, and an inner surface of the axel of the outer hub includes structure thereon defining a corresponding thread. The hub assembly is configured such that when the threads of the clutch drive and the outer hub are engaged, the outer hub rotates with the clutch drive and the inner hub, and when the threads are disengaged, the inner hub rotates with the clutch drive and the outer hub does not rotate with the clutch drive.

In embodiments, the first and second ground-engaging wheels are operably coupled to the clutch drive. The first ground-engaging wheel is positioned between the first drive-wheel of the inner hub and the third drive-wheel of the outer hub, and the second ground-engaging wheel is positioned between the second drive-wheel of the inner hub and the fourth drive-wheel of the outer hub, and wherein the first and second drive. When the clutch drive is disengaged, only one of the first and second ground-engaging wheels rotates, and when the clutch drive is engaged, both of the first and second ground-engaging wheels rotates.

In embodiments, the wheelchair can comprise a foldable base frame, the base frame comprising a rectangular frame comprising at least four members, each member being pivotably coupled to an adjacent member, and further comprising an anti-tip wheel coupled to each corner of the rectangular frame. The foldable base frame folds towards a vertical axis of the wheelchair.

In embodiments, the wheelchair includes foot rest on each side. The footrest is adjustable along a longitudinal axis of the leg link and/or about the longitudinal axis of the leg link. The wheelchair can also include a height adjustable handlebar assembly.

Wheelchairs according to embodiments of the disclosure are configured such that when the first lower extremity is extended in a forward position, the second lower extremity is in a bent, unextended position, and vice versa, thereby mimicking the contralateral motion of walking.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIGS. 18A and 18B are perspective views of a wheelchair with and without a seated user in accordance with another embodiment of the disclosure.

FIG. 21 is an exploded view of the wheelchair of FIG. 20.

FIG. 22A is a perspective view of an assembled one-half combined foot and hand mechanism assemblies of the wheelchair of FIG. 20.

FIG. 22B is an exploded view of the one-half combined foot and hand mechanism assemblies of FIG. 22A.

FIG. 23 is a perspective view of an assembled foot mechanism assembly of FIG. 22A.

FIG. 24 is a series of side views depicting an arced path of the foot mechanism assembly of FIG. 23 through one stroke.

FIG. 36 is a series of side views depicting an arced path of the hand mechanism assembly of FIG. 35A through one stroke.

FIG. 38A-38H is a series of perspectives views depicting telescoping height adjustment and pivoting foot rest adjustment of the foot rest assembly of FIG. 37A.

FIG. 42A is a top plan view of the handlebar and seat assemblies of FIG. 41.

FIG. 42B is a left hand side elevational view of the handlebar and seat assemblies of FIG. 41.

FIG. 42C is a rear elevational view of the handlebar and seat assemblies of FIG. 41.

FIGS. 44A-44D is a series of perspective views depicting various finial configurations of the backrest of FIG. 33A.

FIGS. 45A-45D is a series of perspective views depicting various backrest wing configurations of the backrest of FIG. 33A.

FIGS. 46A and 46B are perspective view of pivoting couplers of the tubular frame assembly of FIG. 33A.

FIG. 47A is a perspective view of the tubular frame assembly of FIG. 33A in an unfolded configuration.

FIG. 47B is a top plan view of the tubular frame assembly of FIG. 47A.

FIG. 47C is a perspective view of the tubular frame assembly of FIG. 33A in a half folded configuration.

FIG. 47D is a top plan view of the tubular frame assembly of FIG. 47C.

FIG. 47E is a perspective view of the tubular frame assembly of FIG. 33A in a folded configuration.

FIG. 47F is a top plan view of the tubular frame assembly of FIG. 47E.

FIG. 49A is a perspective view of a wheel and hub assembly of FIG. 33A.

FIG. 49B is a left hand side elevational view of the assembly of FIG. 49A.

FIG. 49C is a front elevational view of the assembly of FIG. 49A.

Figure 1:
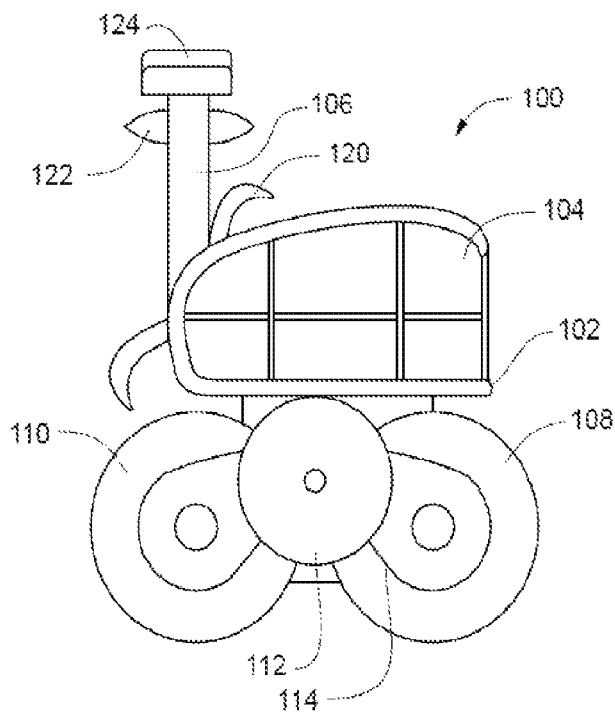
FIGS. 1-17 depict various embodiments of a wheelchair in accordance with the disclosure.
Figure 2:
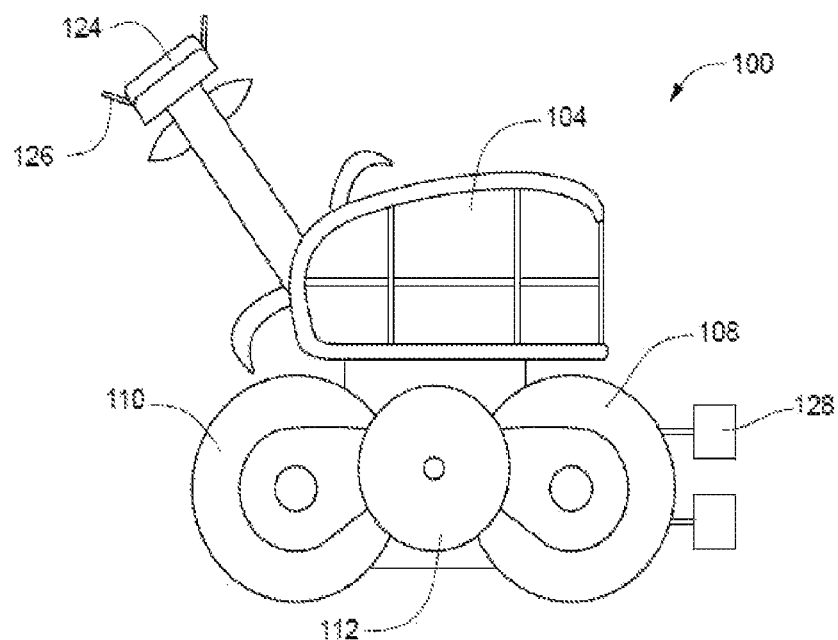

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIGS. 1-17 various embodiments of a wheelchair 100 are depicted in accordance with the disclosure. In some embodiments, the wheelchair 100 is configured to impart motion on one or more lower extremities of a user to inhibit inelasticity in joints of one or more lower extremities as a result of extended immobility, and to promote a natural alignment of one or more upper extremities of the user over a Base of Support (BOS) during manipulation of the wheelchair to impart locomotion.

In one embodiment, the wheelchair 100 can include a frame 102, which can include a seat 104 and optional reclining backrest 106. The wheelchair 100 can further include six main wheels, with three wheels positioned on each lateral side of the wheelchair 100. For example, in one embodiment, the wheelchair 100 can include a forward set of ground engaging wheels 108, a rearward set of ground engaging wheels 110, and a set of control wheels 112 configured for user manipulation for locomotion of the wheelchair 100. The forward set of ground engaging wheels 108 and the rearward set of ground engaging wheels 110 can be configured to contact the ground on each lateral side of the wheelchair 100. The set of control wheels 112 can be configured to propel the forward set of ground engaging wheels 108 and/or the rearward set of ground engaging wheels 110. For example, in one embodiment, each of the control wheels 112 can be configured to drive a corresponding one of the at least one of forward set of ground engaging wheels 108 and/or rearward set of ground engaging wheels 110. In one embodiment, the set of control wheels 112 can be operably coupled to the forward set of ground engaging wheels 108 and/or the rearward set of ground engaging wheels 110 via a gear system 114. In one embodiment, the gear system 114 can be configured to enable the forward set of ground engaging wheels 108 and/or the rearward set of ground engaging wheels 110 to move contralaterally to one another.

Figure 7:
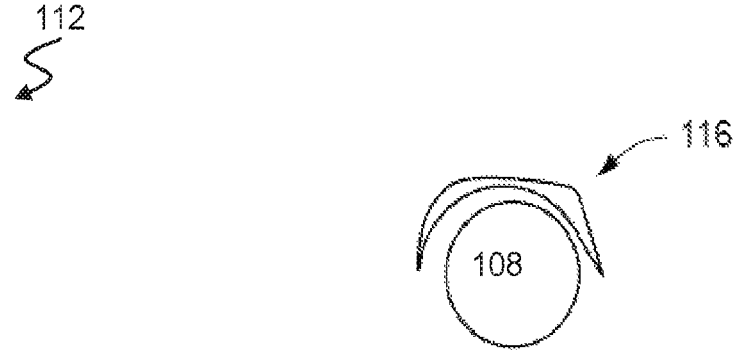
Figure 8:
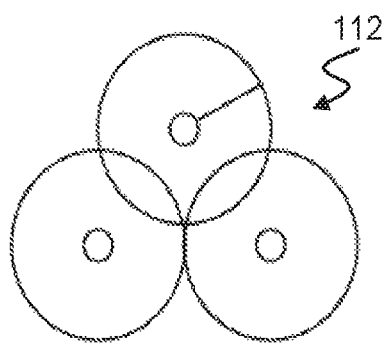
Figure 10:
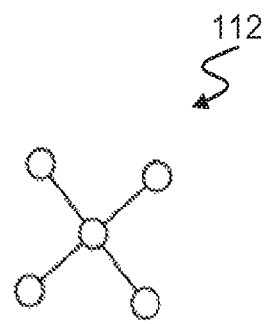
Figure 11:
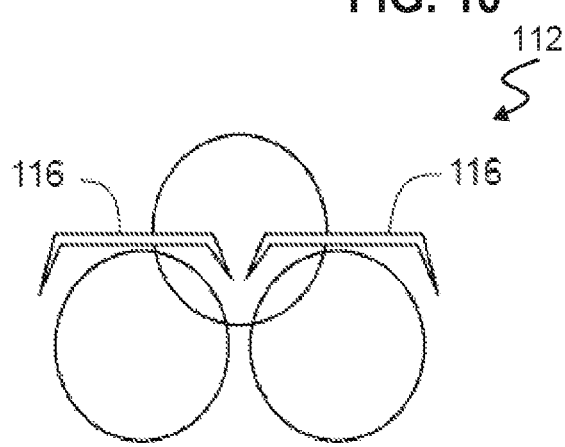
Figure 9:
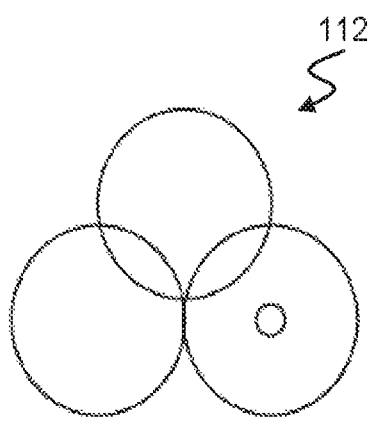
Figure 12:
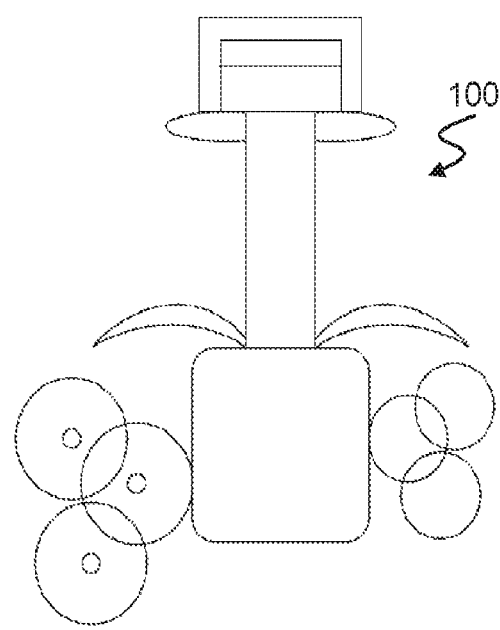
Figure 13:
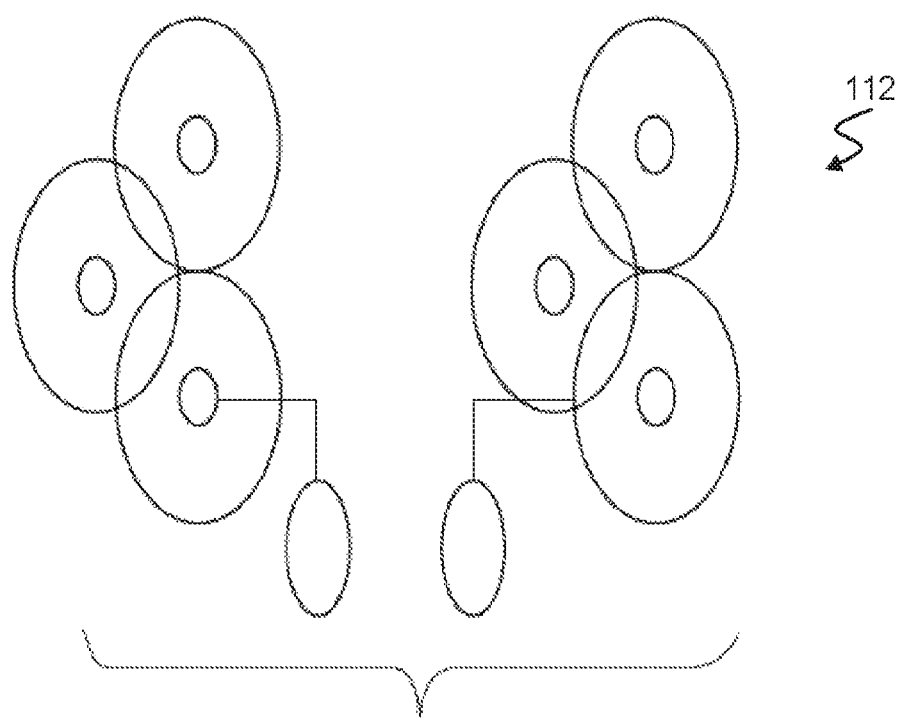
Figure 14:
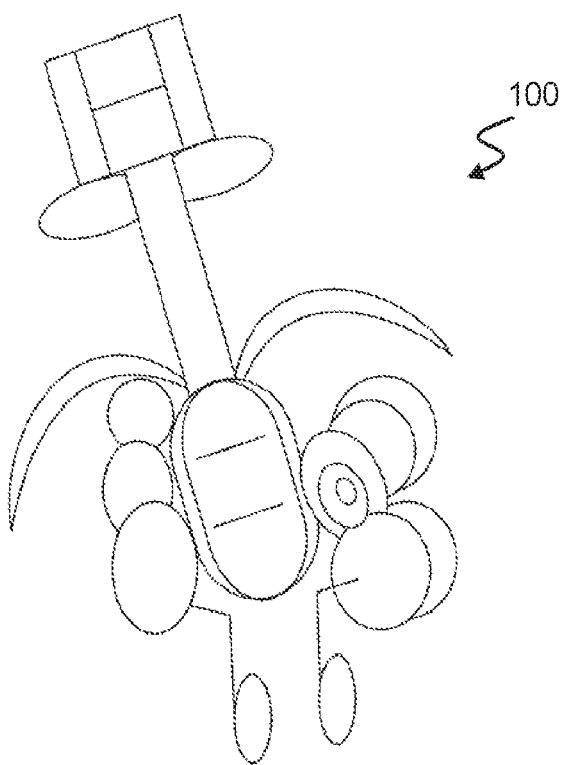

In one embodiment, at least one of the forward set of ground engaging wheels 108 and/or the rearward set of ground engaging wheels 110 can include wheel guards or fenders 116 (as depicted in FIGS. 7 and 11) configured to inhibit dirt, debris and water from coming in contact with control wheels 112 and the wheelchair user. In some embodiments, the fenders 116 can include battery or solar powered lights for improved visibility.

Figure 3:
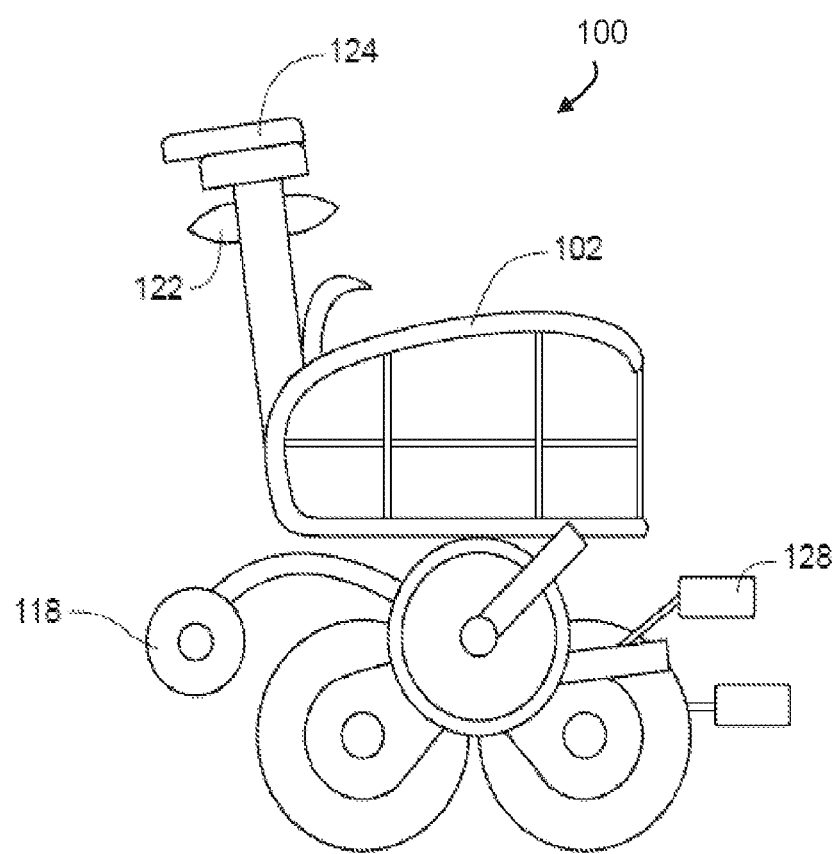
Figure 4:
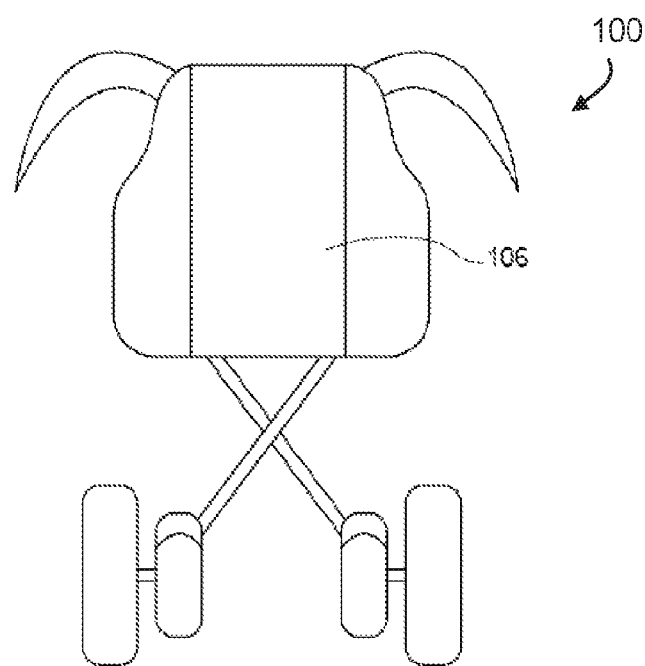
Figure 5:
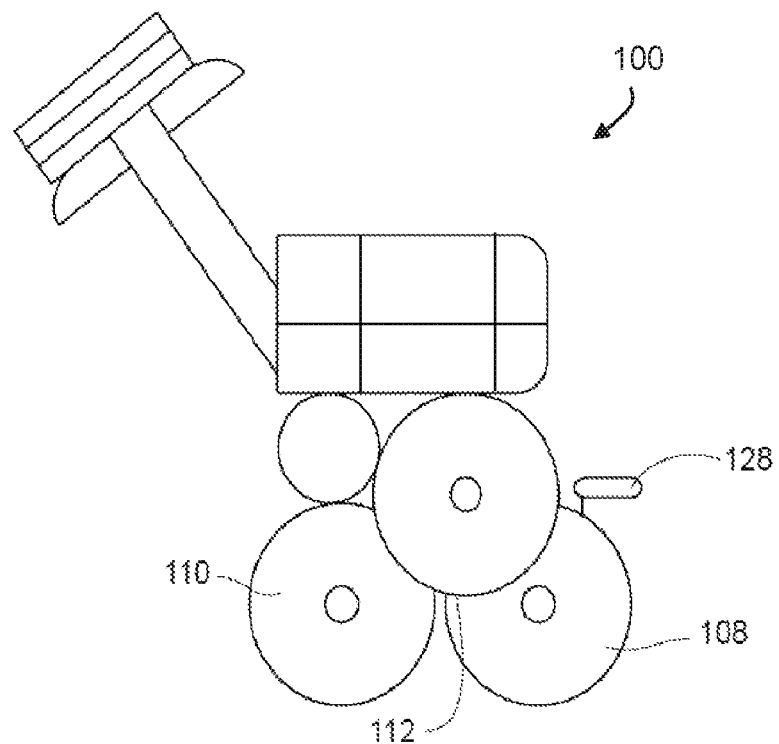
Figure 6:
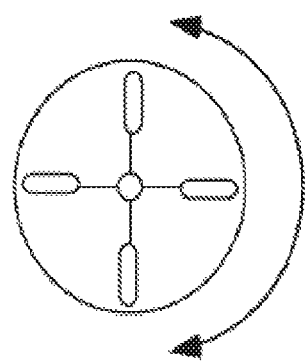

In one embodiment, the wheelchair 100 can include one or more anti-tipping wheels 118 (as depicted in FIG. 3) positioned on the lateral sides or ear portion of the wheelchair 100. The wheelchair 100 can include a braking system 119 operably coupled to the set of control wheels 112, such that the braking system 119 can be selectively, partially engaged when operating on a slanted or inclined surface, and selectively, fully engaged when the wheelchair 100 is at rest.

In one embodiment, the control wheels 112 can be positioned adjacent to a bottom portion of the wheelchair seat 104, thereby enabling the arms of the user to remain relatively straight, such that the user's shoulder girdle remains within the natural BOS during manipulation and locomotion. In one embodiment, the seat 104 of the wheelchair 100 can be firmly padded, and can be integrally attached to the frame 102 to lock in place horizontally across the frame 102 in an in-use position. Seat 104 can be inclined (either by battery power or manually) to one or more non-horizontal positions to adequately support a user's spine and back. When the wheelchair 100 is folded, the seat 104 can be unlocked and pivotably moved to a vertical position and optionally attached to the frame 102 for securement in a storage position.

In one embodiment, the seat 104 can be between about 18 inches and about 22 inches in width, and about 20 inches in length. In one embodiment, the seat 104 can be shaped to narrow in width towards a back of the seat 104. In one embodiment, the lateral outside edges of the seat 104 can be slightly raised for improved stability of the user and for improved comfort. In one embodiment, the wheelchair 100 can further include a seatbelt; for example, a four point seatbelt.

Figure 15A:
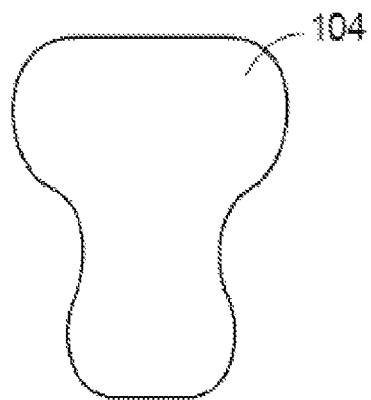
Figure 15B:
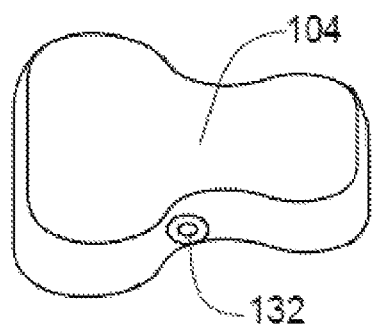

As further depicted in FIGS. 15A-B, in one embodiment, the seat 104 can have a saddle shape having a generally narrow forward portion configured to enable ease of a user of moving into and out of the seat 104. In one embodiment, the angle and tilt of the seat 104 relative to the frame 102 can be adjusted, for example, via mechanical actuation controllable by one or more control buttons 131 located on a side portion of the seat 104. In one embodiment, the seat 104 can be at least partially constructed of one or more layers of memory foam for improved comfort. In one embodiment, the backrest 106 can additionally be padded for spinal support.

The optional backrest 106 can be shaped and sized to minimize interference with movement of the user's arms during locomotion, thereby enabling a more naturally aligned arm swing during actuation. The natural swinging of the arms over the user's natural BOS during locomotion enables the user's pectoral girdle to remain aligned over the user's pelvic girdle. For example, in one embodiment, the backrest 106 of the wheelchair 100 can be between about 20 inches and about 24 inches in height, between about 10 inches and about 12 inches in width, and between about 3 inches and about 5 inches in depth. The backrest 106 can fully padded to help support the alignment and positioning of the head and spine of the user. In embodiments, backseat 106 can be in a substantially vertical position or can be inclined in a plurality of positions to accommodate various heights of a subject pushing the wheelchair 100 and/or to support the spine of a user comfortably.

In one embodiment, the wheelchair 100 can include movable padded armrests 120, which can be selectively positioned either vertically or horizontally when the wheelchair is at rest. In some embodiments, the armrests 120 can be positioned around a torso of the user to help maintain the user's torso in a desired orientation and position during locomotion, thereby enabling the user's elbows to swing backward while enabling continued alignment between the user's shoulder girdles and the user's arms. In one embodiment, one or more handholds 122 can be operably coupled to a top of the backrest 118. The one or more handholds 122 can be padded and can be used as an aid when positioning the user into or out of the wheelchair 100. Additionally, bags, purses or other items can be hung from the one or more handholds 122.

One or more crossbar handles 124 can be operably coupled to a frame 102 of the wheelchair 100 and can be vertically adjustable to accommodate users of different heights. One example of such a crossbar handle 124 is depicted in U.S. patent application Ser. No. 16/007,720, the contents of which are hereby incorporated by reference herein. In one embodiment, the one or more crossbar handles 124 can be pivotably coupled to the frame, so as to selectively lock in a horizontal position when use is desired. When the wheelchair is folded in the storage position, the one or more crossbar handles 124 can be unlocked and pivotably moved to a vertical position. In some embodiments, the one or more crossbar handles 124 can optionally include a brake actuator 126 configured to serve as an actuator to the braking system 118.

A pair of footrests 128 can be operably coupled to the forward set of ground engaging wheels 108, wherein rotation of each wheel of the forward set of ground engaging wheels 108 can be configured to impart a corresponding translational motion, such as a linear, arcing, or swinging motion of each footrest of the pair of footrests 128, so as to impart motion on the one or more lower extremities of the user to inhibit inelasticity in joints of the one or more lower extremities as a result of extended immobility. For example, in one embodiment, the wheelchair can include footrests 128 operably coupled to an off-center axis of one or more ground engaging wheels, such that each rotation of the wheel about a central axis causes a corresponding movement of the footrest 128. The motion of the footrests 128 can be arcing, circular, elliptical, linear, or any shape that promotes a more natural muscle stretching and joint articulation in the legs and feet of the user. In some embodiments, the foot rests 128 can be weighted to aid the user in maintaining the heels of their feet lower than their toes during locomotion.

Figure 16:
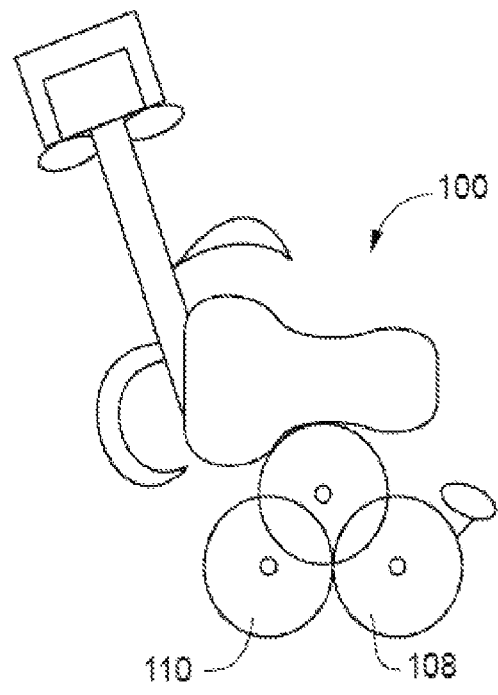
Figure 17:
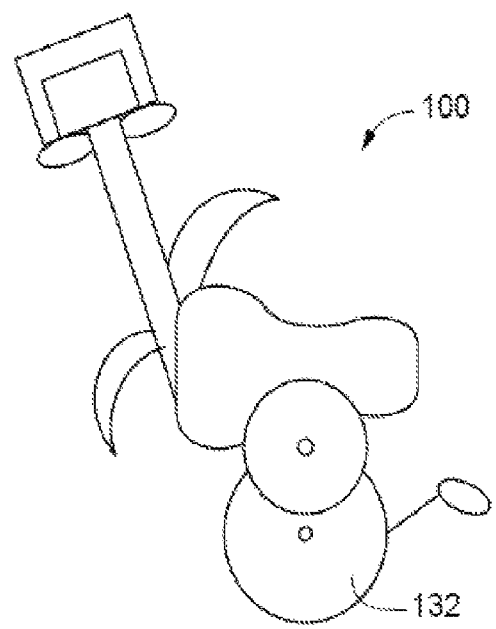
Figure 19C:
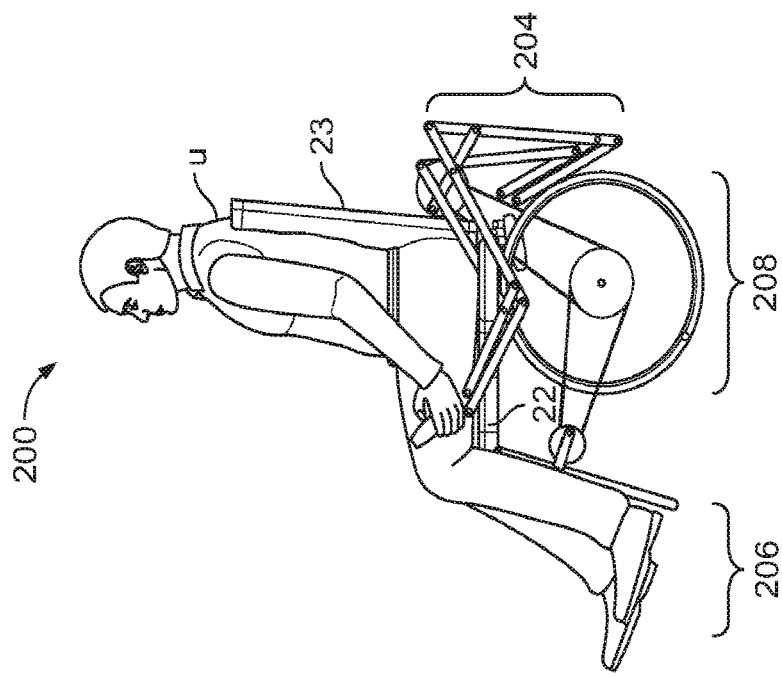
FIG. 19C is a left hand side elevational view of the wheelchair of FIG. 18A with a seated user.
Figure 19B:
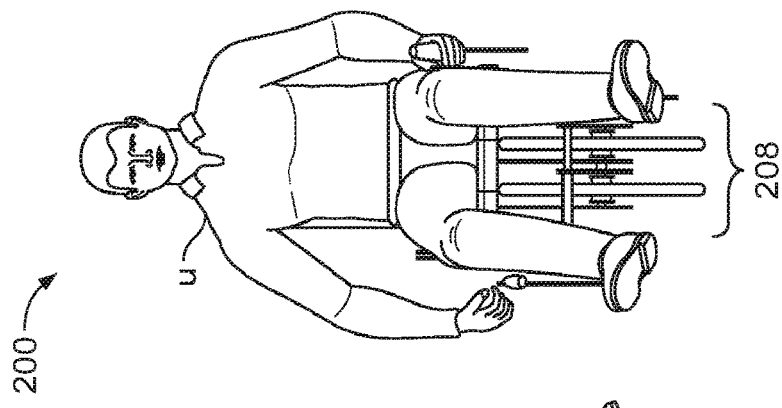
FIG. 19B is a front elevational view of the wheelchair of FIG. 18A with a seated user.
Figure 19A:
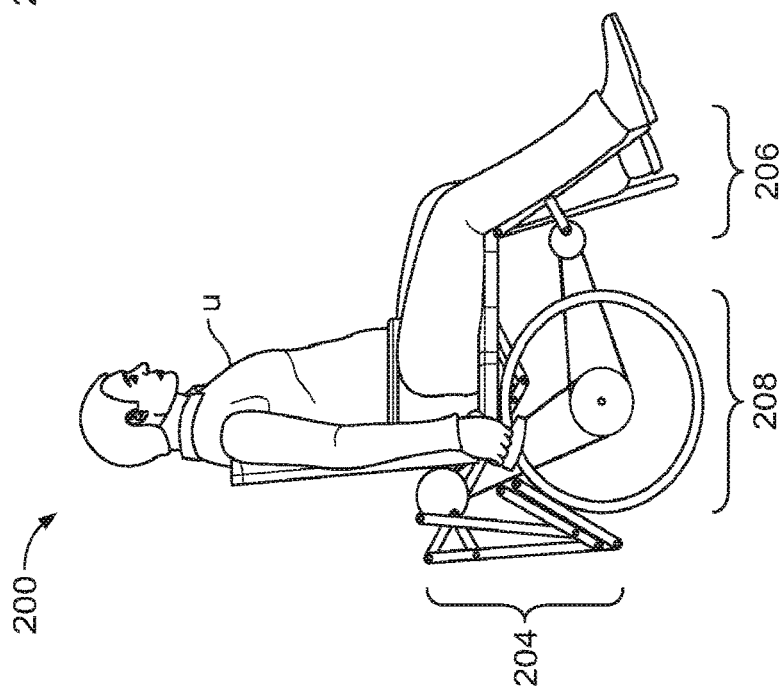
FIG. 19A is a right hand side elevational view of the wheelchair of FIG. 18A with a seated user.
Figure 19E:
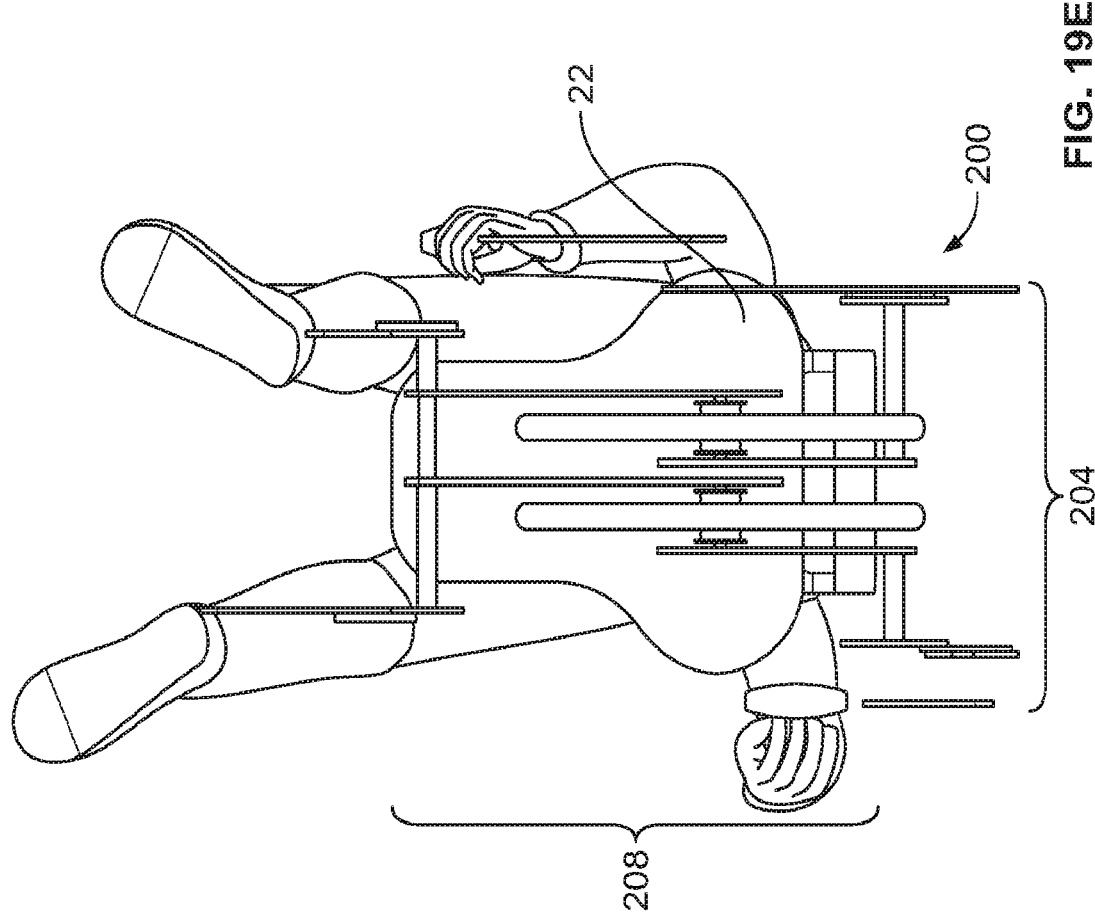
FIG. 19E is a bottom plan view of the wheelchair of FIG. 18A with a seated user.
Figure 19D:
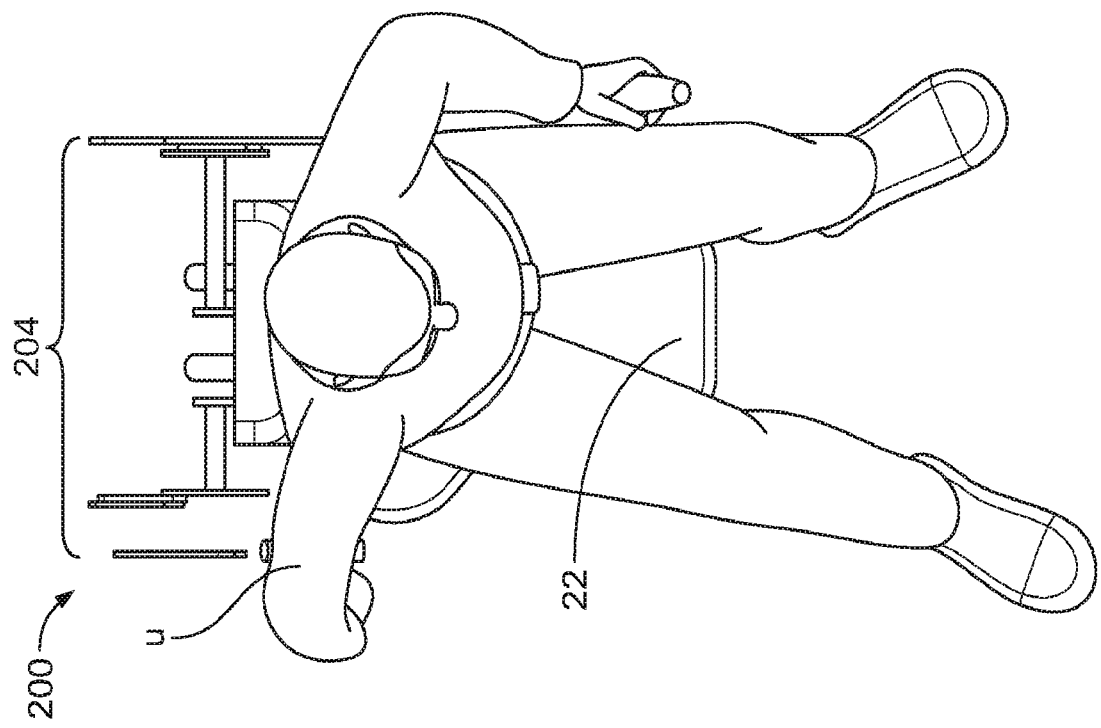
FIG. 19D is a top plan view of the wheelchair of FIG. 18A with a seated user.

Referring to FIGS. 16 and 17, in one embodiment, the wheelchair 100 can include four ground engaging wheels (including a forward set of ground engaging wheels 108 and a rearward set of ground engaging wheels 110). In another embodiment, the wheelchair can include two primary ground engaging wheels 132, which can be in combination with an anti-tipping wheel 118 and/or a stability augmentation device (not depicted) configured to aid in stability of the wheelchair 100 during use. Other wheel configurations are also contemplated.

Now referring to an embodiment depicted in FIGS. 18A-26D, a wheelchair 200 generally includes a seat assembly 202, a hand mechanism assembly 204, and a foot mechanism assembly 206 coupled to hand mechanism assembly 204 via a drive-wheel and chain assembly 208. Wheelchair 200 is configured to impart contralateral movement of one or more lower extremities of a user to inhibit inelasticity in joints of one or more lower extremities as a result of extended immobility, and to promote a natural alignment of one or more upper extremities of the user over a Base of Support (BOS) during manipulation of the wheelchair to impart locomotion.

Figure 20:
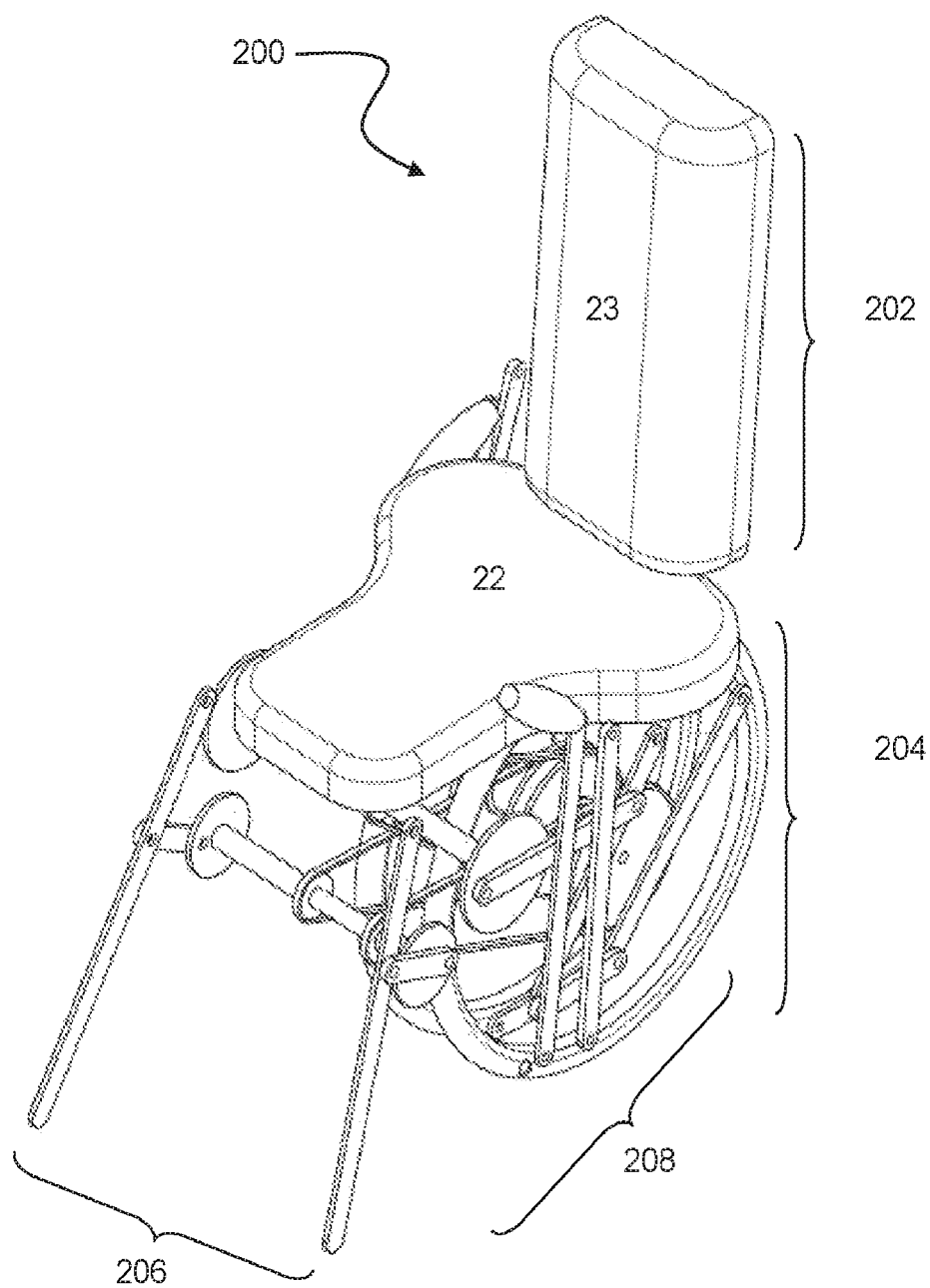
FIG. 20 is a perspective view of the wheelchair of FIG. 18B.

Referring to FIGS. 20 and 21, seat assembly generally 202 includes a seat 22 and a backrest 23. Seat 22 and backrest 23 can be similar to seat 104 and backrest 106, as described above, and can be optionally movable with respect to one another for inclination of backrest 23 and/or seat 22. Hand mechanism assembly 204 and foot mechanism assembly 206 are coupled to seat assembly 202 and each other via drive-wheel and chain assembly 208. For example, in the embodiment shown, such as in FIGS. 19A-19E, drive-wheel and chain assembly 208 is primarily coupled to an underside and rear portion of seat 22, while foot mechanism assembly 206 is primarily coupled to a front side portion of seat 22 and drive-wheel and chain assembly 208, and hand mechanism assembly 204 is coupled to drive-wheel and chain assembly 208 proximate a rear side portion of seat 22.

Referring back to FIGS. 20 and 21, drive-wheel and chain assembly 208 can comprise two drive-wheel subassemblies (right side (RS) and left side (LS)) positioned primarily underneath seat 22. Each subassembly generally includes a wheel 24, such as a rubber wheel as known to one of ordinary skill in the art, a first drive-wheel hub 25 is positioned on a first side of wheel 24 at its center, and a second drive-wheel hub 26 is positioned on a second side of each wheel 24 at its center. An axel 14 extends between first and second drive-wheel hubs 25, 26 and between each wheel 24 such that all hubs 24, 25 and the subassemblies are connected. First drive-wheel hubs 25 are each coupled to a leg drive chain 29 for operably coupling foot mechanism assembly 206 to drive-wheel and chain assembly 208, and second drive-wheel hubs 26 are each coupled to an arm drive chain 27 for operably coupling hand mechanism assembly 204 to drive-wheel and chain assembly 208. First and second drive-wheel hubs 25, 26, and wheels 24 rotate together, such as in a dual clutch transmission assembly mode (described infra), and transfer energy from hand mechanism assembly 204 to drive-wheel and chain assembly 208 and from drive-wheel and chain assembly 208 to foot mechanism assembly 206. More specifically, one drive-wheel subassembly connects a RS hand mechanism subassembly to a LS foot mechanism subassembly, while the other drive-wheel subassembly connects a LS hand mechanism subassembly to a RS foot mechanism assembly, as will be described in more detail below.

As shown in FIGS. 21, 22A, 22B, and 23, drive-wheel and chain assembly 208 is operably coupled to foot mechanism assembly 206 by the pair of leg drive chains 29 which transfer energy from second drive-wheel hubs 26 to foot mechanism assembly 206. Foot mechanism assembly 206 generally includes two subassemblies (RS and LS) positioned on each side of chair 200, each of which include a leg drive-wheel 6, linkage 5, and a leg link 3. More specifically, and referring to the RS subassembly depicted in FIGS. 22A and 22B, chain 29 is coupled at a first end to second drive-wheel hub 26, and a second end to a leg drive-wheel 6 of foot mechanism assembly 206. Referring to FIG. 23, leg drive-wheel 6 is fixedly coupled to a first end of linkage 5, which is pivotably coupled at a second end to a position along leg link 3 near a top end of link 3. A bottom end of link 3 can be coupled to a foot rest or pedal (not shown) for a user to rest its foot thereon.

As best depicted in FIG. 24, in use, as second drive-wheel hubs 26 of drive-wheel and chain assembly 208 rotate, chains 29 transfer energy to leg drive-wheels 6 causing leg drive-wheels 6 and axel 14 to rotate. The rotational movement of leg drive-wheels 6 is converted to an arcing movement of leg link 3 via linkage 5. This allows the user's leg to move in an arced fashion, which simulates the gait of a walker. Foot mechanism assembly 206 is assembled to mimic contra-lateral movement of a user's gait when walking.

Figure 25A:
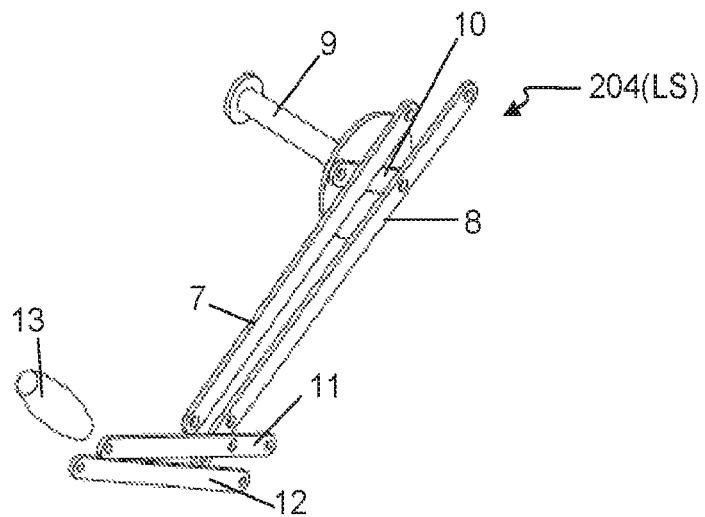
FIG. 25A is a perspective view of an assembled hand mechanism assembly of FIG. 22A.
Figure 25B:
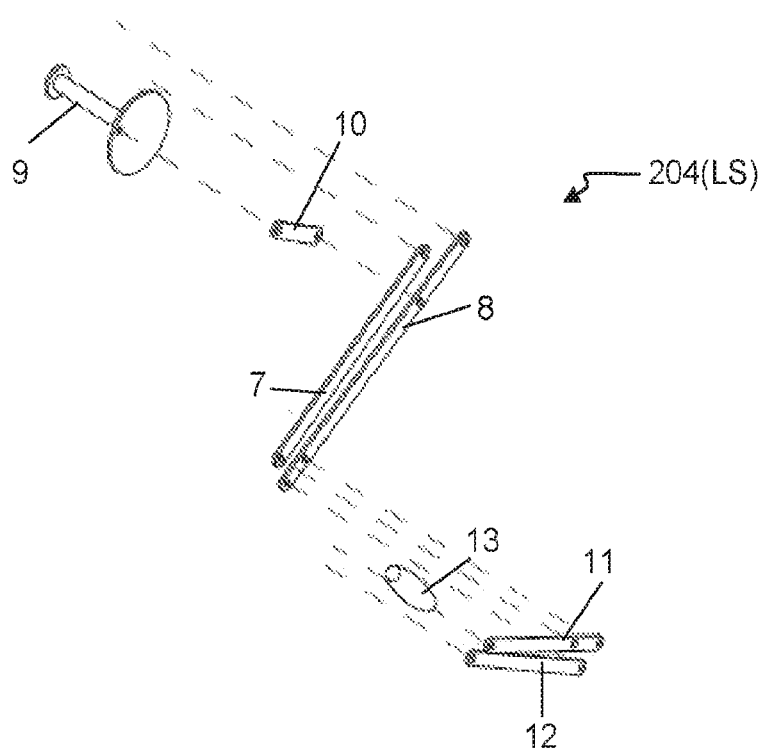
FIG. 25B is an exploded view of the hand mechanism assembly of FIG. 25A.
Figures 26A, 26B:
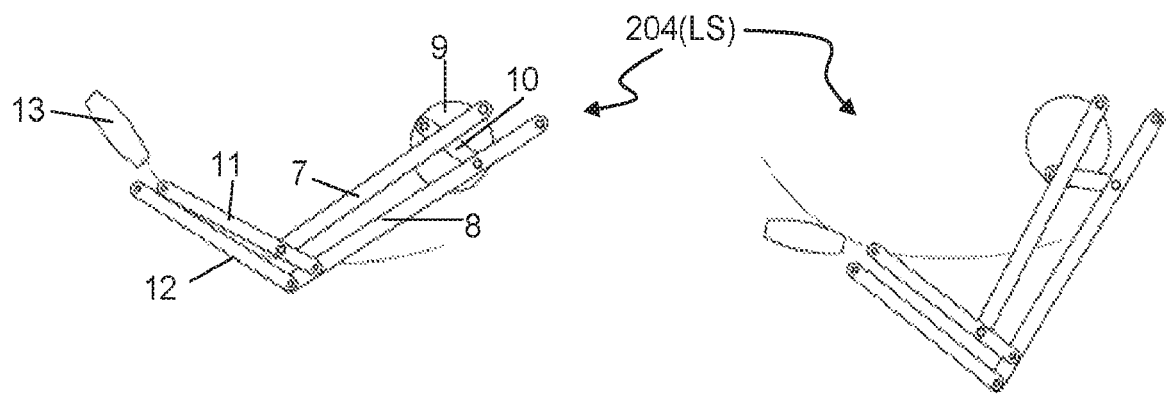
FIGS. 26A-26D is a series of side views depicting an arced path of the hand mechanism assembly of FIG. 23 through one stroke.
Figures 26C, 26D:
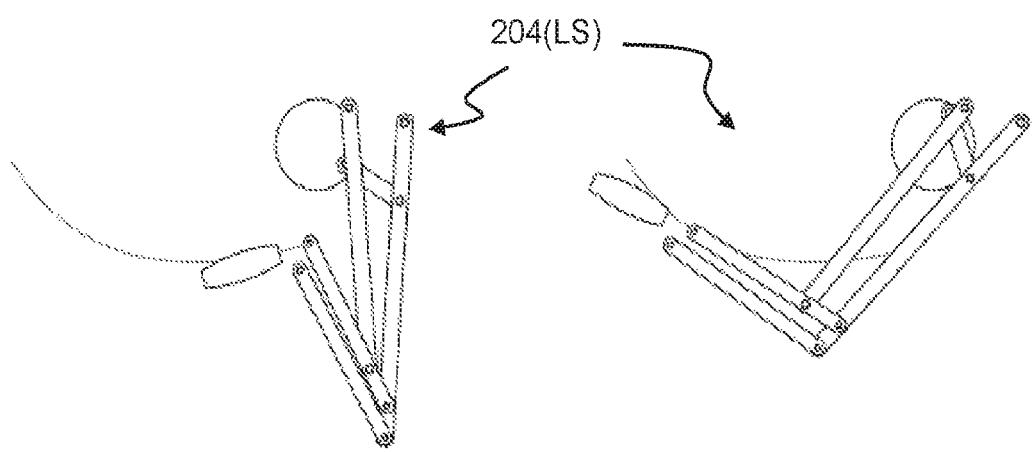

Now referring to FIGS. 21, 22A, 22B, 25A, and 25B, drive-wheel and chain assembly 208 is also operably coupled to hand mechanism assembly 204 by the pair of arm drive chains 27 which transfer energy from hand mechanism assembly 204 to first drive-wheel hubs 25. Hand mechanism assembly 204 generally includes two subassemblies (RS and LS) positioned on each side of seat 22, each of which include an arm drive-wheel 9 positioned behind backrest 23, linkage 10, a pair of arm links 7, 8, a pair of grip links 11, 12, and a grip or handle 13. More specifically, and referring to the LS subassembly depicted in FIGS. 22A and 22B, chain 27 is coupled at a first end of first drive-wheel hub 25, and a second end to an arm drive-wheel 9 of hand mechanism assembly 204. Referring to FIGS. 25A and 25B, arm drive-wheel 9 is fixedly coupled to a first end of linkage 10, which is pivotably coupled at along a top portion of arm link 8. Arm link 8 is pivotably coupled near a second end to a terminal end of grip link 11, and arm link 8 is pivotably coupled at its terminal second end to a terminal end of grip link 12 such that grip link 11 is positioned above grip link 12. Arm link 7 is also pivotably coupled at a second end to grip link 11 near its second end and above where grip link 11 is coupled to arm link 8. Grip 13 is then pivotably coupled to a second terminal end of grip link 11.

As depicting in FIGS. 26A-26D, in use, this interlink four-sided geometry follows a curved or arced path causing the angle of grip 13 to adjust to be tangent to the arc path. More specifically, a user grips left hand grip 13 with the user's hand. As force is applied to downward to grip 13, the force causes grip 13 to pivot, which in turn causes LS grip links 11, 12 to pivot with respect to LS arm links 7, 8, which in turns causes LS drive-wheel 9 to rotate via linkage 10, which converts the pivoting translational motion of LS interlinked links 7, 8, 11, and 12 into rotational movement of LS drive-wheel 9. This rotation causes energy to be transferred via LS drive chain 27 to LS drive-wheel hub 25. Due to RS drive-wheel hub 26 being coupled to LS drive-wheel hub 25, RS drive-wheel hub 26 then rotates, transferring energy to RS foot mechanism subassembly for movement described above with respect to FIG. 24. Wheels 24 also rotate and chair 200 moves forward or backward (depending on the direction of motion of grips 13), and equally the LS foot mechanism subassembly 206 moves contralateral with respect to RS hand mechanism subassembly 204. In other words, forcing RS grip 13 in forward motion ultimately causes LS foot link 3 to move forward, and chair 200 to move forward, and vice versa, mimicking the contralateral movement of walking.

Figure 27:
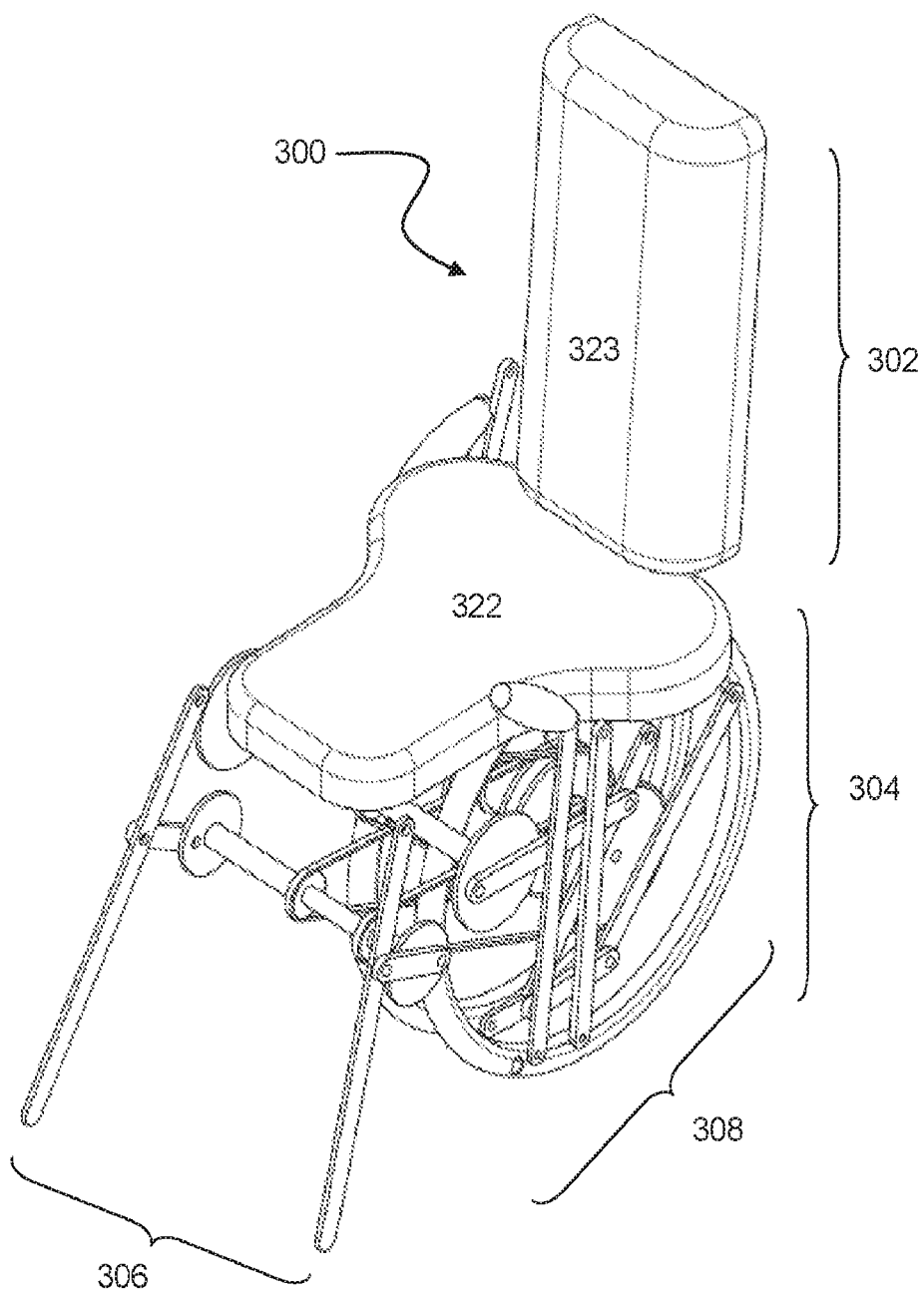
FIG. 27 is a perspective view of a wheelchair with and without a seated user in accordance with another embodiment of the disclosure.

In another embodiment of the invention, and referring to FIGS. 27-30D, a wheelchair 300 generally includes a seat assembly 302, similar to seat assembly 202 described above, a hand mechanism assembly 304, and a foot mechanism assembly 306 coupled to hand mechanism assembly 304 via a drive-wheel and chain assembly 308. Referring to FIG. 27, seat assembly generally 302 includes a seat 322 and a backrest 323, and is similar in configuration to seat assembly 202 described above. Hand mechanism assembly 304 and foot mechanism assembly 306 are coupled to seat assembly 302 and each other via drive-wheel and chain assembly 308. In the embodiment shown, drive-wheel and chain assembly 308 is primarily coupled to an underside and war portion of seat 322, while foot mechanism assembly 306 is primarily coupled to a front side portion of seat 322 and drive-wheel and chain assembly 308, and hand mechanism assembly 304 is coupled to drive-wheel and chain assembly 308 proximate a rear side portion of seat 322.

Figure 28A:
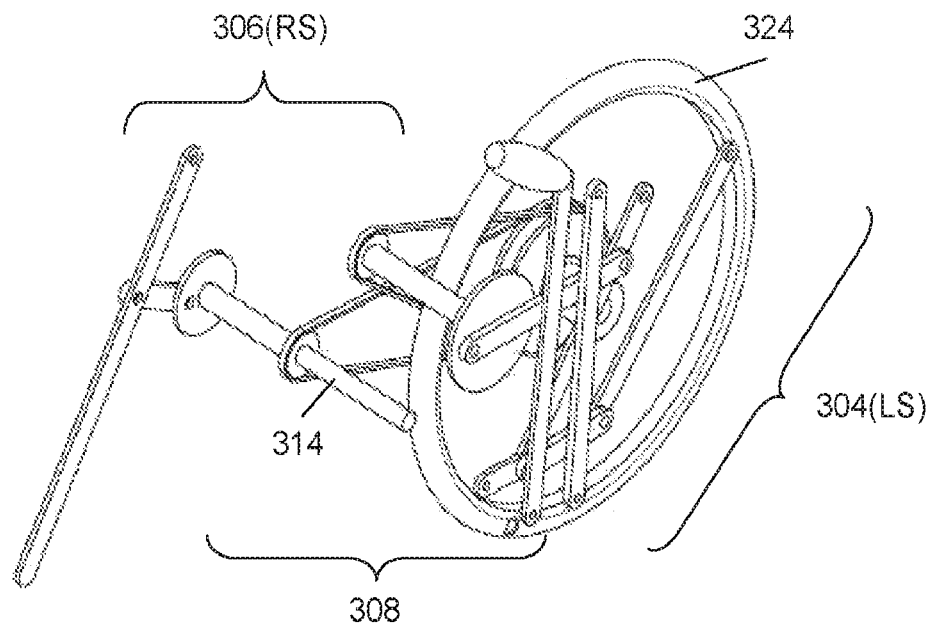
FIG. 28A is a perspective view of an assembled one-half combined foot and hand mechanism assemblies of the wheelchair of FIG. 27.
Figure 28B:
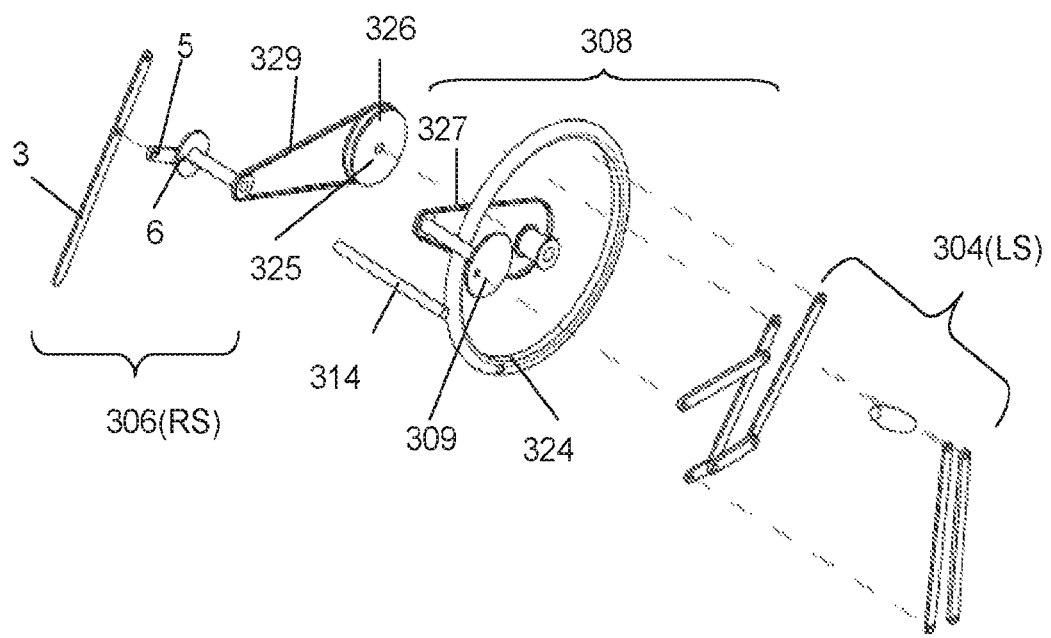
FIG. 28B is an exploded view of the one-half combined foot and hand mechanism assemblies of FIG. 28A.
Figure 29A:
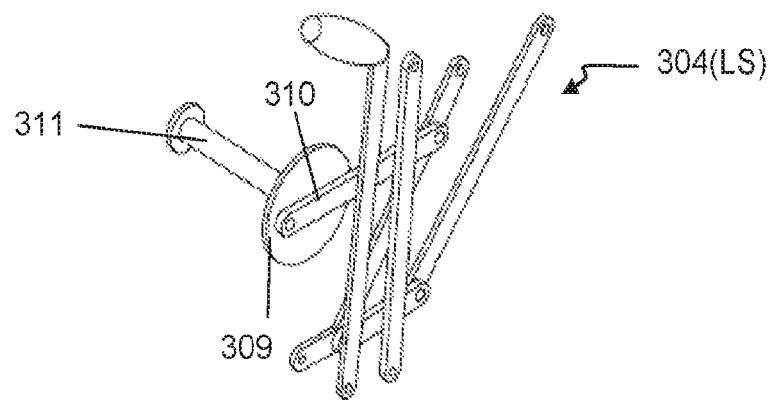
FIG. 29A is a perspective view of an assembled hand mechanism assembly of FIG. 28A.
Figure 29B:
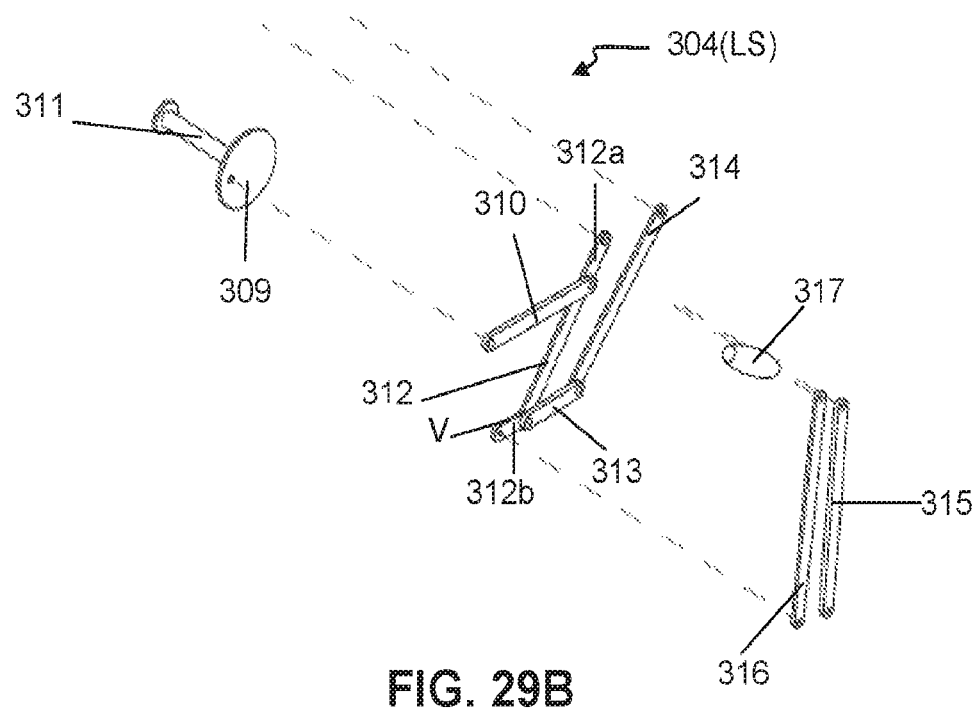
FIG. 29B is an exploded view of the hand mechanism assembly of FIG. 29A.
Figures 30A, 30B:
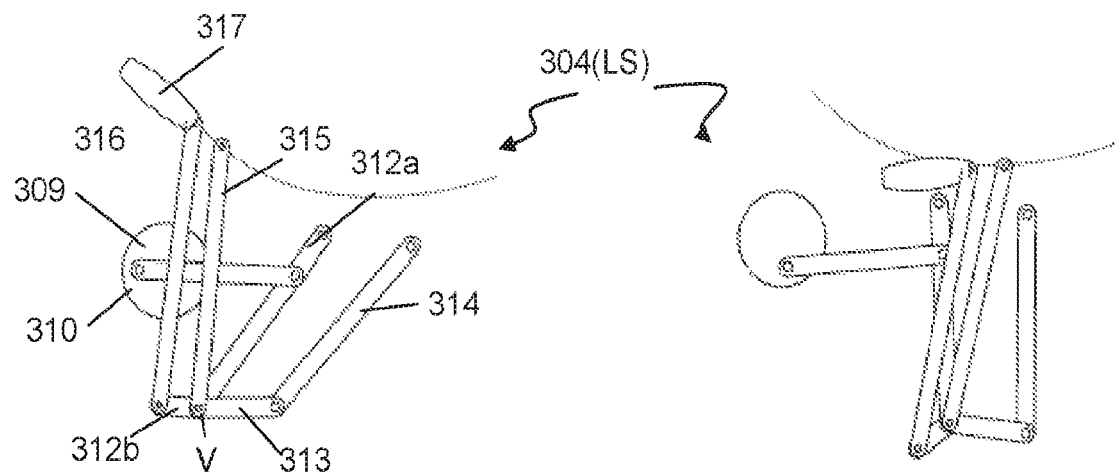
FIGS. 30A-30D is a series of side views depicting an arced path of the hand mechanism assembly of FIG. 29 through one stroke.
Figures 30C, 30D:
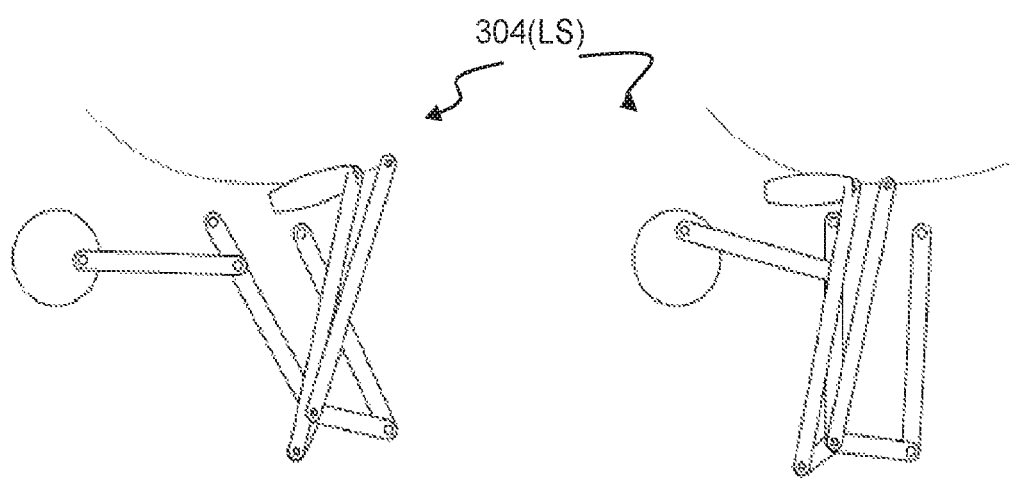
Figure 31C:
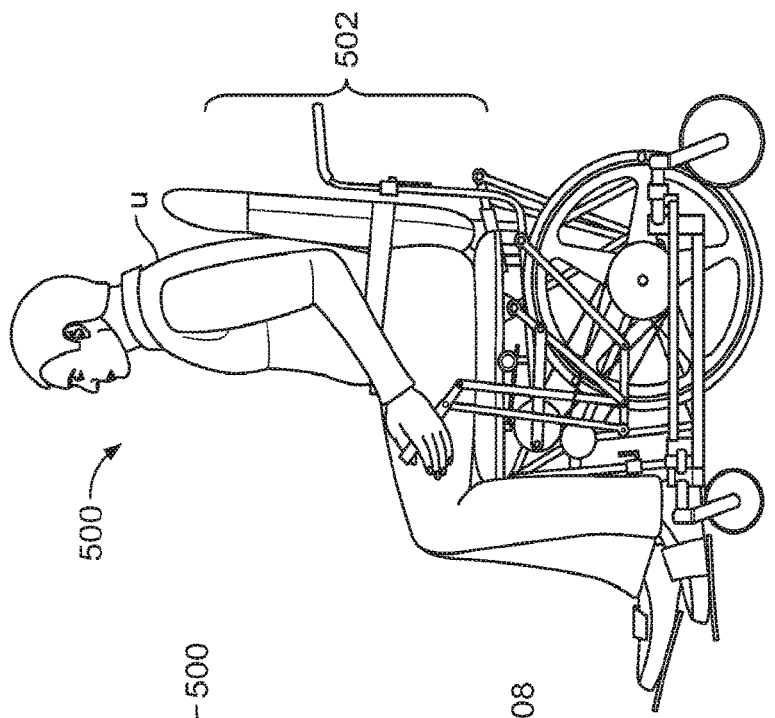
FIG. 31C is a left hand side elevational view of the wheelchair of FIG. 31A with a seated user.
Figure 31B:
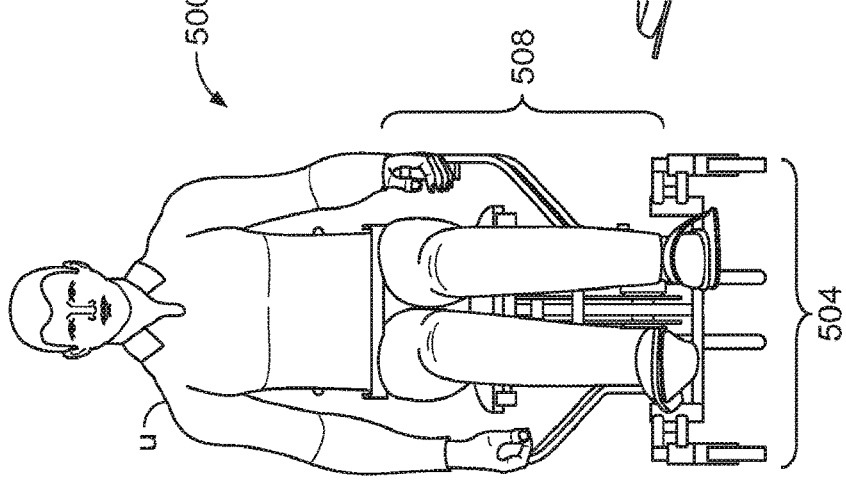
FIG. 31B is a front elevational view of the wheelchair of FIG. 31A with a seated user.
Figure 31A:
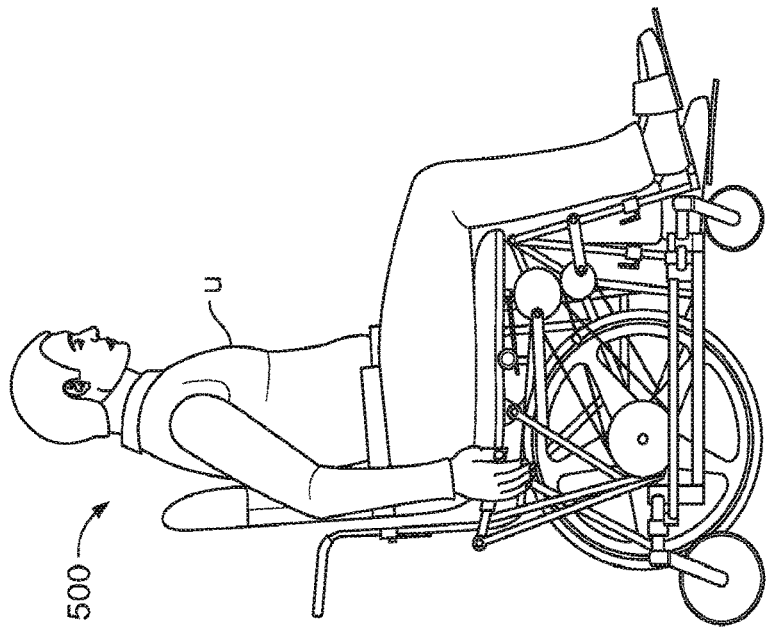
FIG. 31A is a right hand side elevational view of a wheelchair with a seated user in accordance with another embodiment of the disclosure.
Figure 31E:
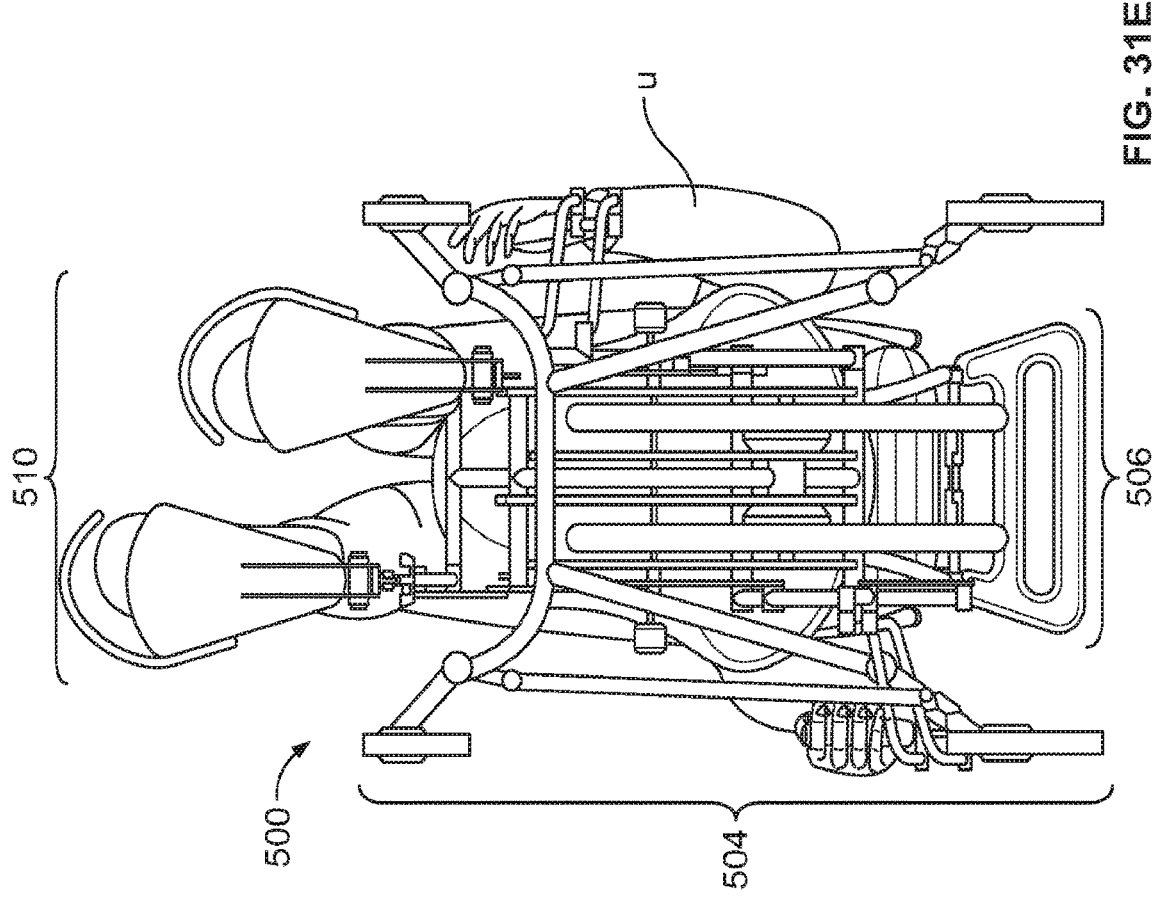
FIG. 31E is a bottom plan view of the wheelchair of FIG. 31A with a seated user.
Figure 31D:
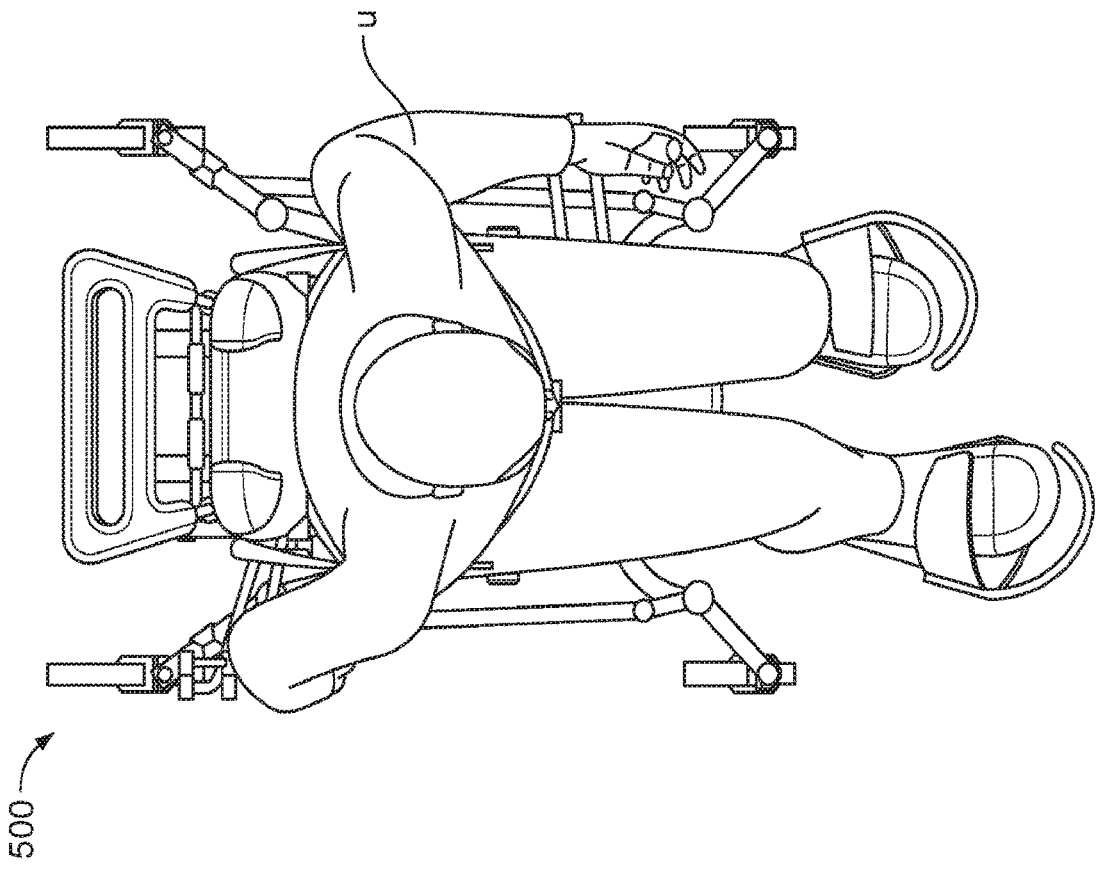
FIG. 31D is a top plan view of the wheelchair of FIG. 31A with a seated user.

Referring now to FIGS. 27, 28A, and 28B, drive-wheel and chain assembly 308 can comprise two drive-wheel subassemblies (right side and left side) positioned on each side of chair 300, each of which includes a wheel 324, such as a rubber wheel as known to one of ordinary skill in the art, a first drive-wheel hub 325 positioned on a first side of wheel 324 at its center, and a second drive-wheel hub 326 positioned on a second side of each wheel 324 at its center. An axel 314 extends between first and second drive-wheel hubs 325, 326 and between each wheel 324 such that all hubs 324, 325 are connected. First drive-wheel hubs 325 are each coupled to a leg drive chain 329 for operably coupling foot mechanism assembly 306 to drive-wheel and chain assembly 308, and second drive-wheel hubs 326 are each coupled to an arm drive chain 327 for operably coupling hand mechanism assembly 304 to drive-wheel and chain assembly 308. First and second hubs 325, 326, and wheels 324 rotate together and transfer energy from hand mechanism assembly 304 to drive-wheel and chain assembly 308 and from drive-wheel and chain assembly 308 to foot mechanism assembly 306.

As shown in FIGS. 27, 28A, and 28B, drive-wheel and chain assembly 308 is operably coupled to foot mechanism assembly 306 by the pair of leg drive chains 329 which transfer energy from second drive-wheel hubs 326 to foot mechanism assembly 306. Foot mechanism assembly 306 is the same as described above (including RS and LS subassemblies with leg drive-wheel 6, linkage 5, and leg link 3) with respect to foot mechanism assembly 206, and as depicted FIGS. 23 and 24, and is not repeated herein for efficiencies.

Now referring to FIGS. 28A, 28B, 29A, and 29B, drive-wheel and chain assembly 308 is also operably coupled to hand mechanism assembly 304 by the pair of arm drive chains 327 which transfer energy from hand mechanism assembly 304 to first drive-wheel hubs 325. Hand mechanism assembly 304 generally includes two subassemblies (RS and LS) positioned on each side of chair 300, each of which includes an arm drive-wheel 309 having an axel 311 that is positioned in front of wheel 324. More specifically, and referring to the left subassembly depicted in FIGS. 29A and 29B, a linkage 310 is fixedly coupled on a first terminal end to drive-wheel 309. A second terminal end of linkage 310 is pivotally coupled to an angled member 312 having a first arm 312a connect to a second arm 312b at a vertex V, forming an obtuse angle. Linkage 310 is coupled near a top portion of first arm 312a. A second linkage 313 is coupled at a first terminal end to the vertex V of angled member 312, and is pivotably coupled at a second terminal end to first terminal end of an arm link 314. A first grip link 315 is pivotably coupled to the first terminal end of second linkage 313 and vertex V of angled member 312. A second grip link 316 is pivotably coupled at a first terminal end to a terminal end of second arm 312b of angled member 312. A grip 317 is pivotably coupled to a second terminal end of second grip link 316.

Similar to hand mechanism assembly 204, in use, this interlinked four-sided geometry follows a curved or arced path causing the angle of grip 317 to adjust to be tangent to the arc path. More specifically, a user grips left hand grip 317 with the user's hand. As force is applied to downward to grip 317, the force causes grip 317 to pivot, which in turn causes LS grip links 315, 316 to pivot with respect to LS arm links 312, 314, which in turns causes LS drive-wheel 309 to rotate via linkage 310 because linkage 310 converts the translational or pivoting motion of LS interlinked links 312, 314, 315, and 316 into rotational movement of LS drive-wheel 309. This rotation causes energy to be transferred via drive chain 327 to LS drive-wheel hub 325. Due to RS leg drive-wheel hub 326 being coupled to LS arm drive-wheel hub 325, which are all coupled to wheels 324, chair 300 moves forward or backward (depending on the direction of motion of grips 13), and the RS foot mechanism subassembly moves contralateral with respect to LS hand mechanism subassembly 304. In other words, forcing right grip 317 in forward motion ultimately causes left foot link 3 to move forward, and chair 300 to move forward, and vice versa, mimicking the contralateral movement of walking.

Referring now to another embodiment of the invention, and referring to FIGS. 31A-53B, a wheelchair 500 generally can comprise a seat assembly 502, a foldable tubular stability frame assembly 504, a drive-wheel and chain assembly 506, a hand mechanism assembly 508, and a foot mechanism assembly 510, similar to that described for wheelchair 300.

Referring to FIGS. 33A-33F, one-half of a drive-wheel and chain assembly 506, a LS hand mechanism subassembly 508, and a RS foot mechanism assembly 510, similar to that described for wheelchair 300, is depicted. In this embodiment, each of drive-wheel and chain assembly 506, hand mechanism assembly 508, and a foot mechanism assembly 510 can comprise two subassemblies, making up the RS and LS of chair 500. Drive wheel subassembly 506a, hand mechanism assembly 508a, and foot mechanism subassembly 510a are depicted in FIGS. 33A-33F, in which drive wheel subassembly 506a links LS hand mechanism subassembly 508a to RS foot mechanism assembly 510a. Drive wheel subassembly 506a includes a wheel 524a, such as a rubber wheel as known to one of ordinary skill in the art. A drive-wheel hub assembly 525 is positioned within wheel 524a, which will be described in more detail. Hub assembly 525 is coupled to a leg drive chain 529 for operably coupling RS foot mechanism subassembly 510a to drive-wheel and chain subassembly 506a, and is coupled to an arm drive chain 527 for operably coupling LS hand mechanism subassembly 508a to drive-wheel and chain subassembly 506a. Hub assembly 525 and wheel 524a rotate together and transfer energy from hand mechanism subassembly 508a to drive-wheel and chain subassembly 506a and from drive-wheel and chain subassembly 506a to foot mechanism subassembly 510a. Subassemblies 506b, 508b, and 510b, operate in a manner as described with respect to the previous embodiments, and which is not repeated here for efficiencies.

Figure 34A:
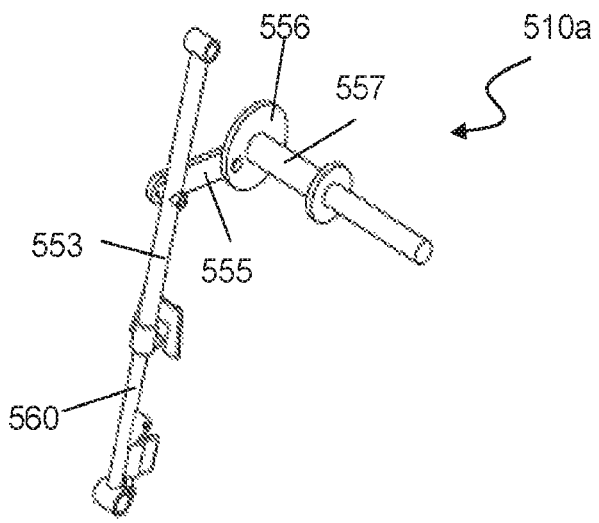
FIG. 34A is a perspective view of an assembled foot mechanism assembly of FIG. 33A.
Figure 34B:
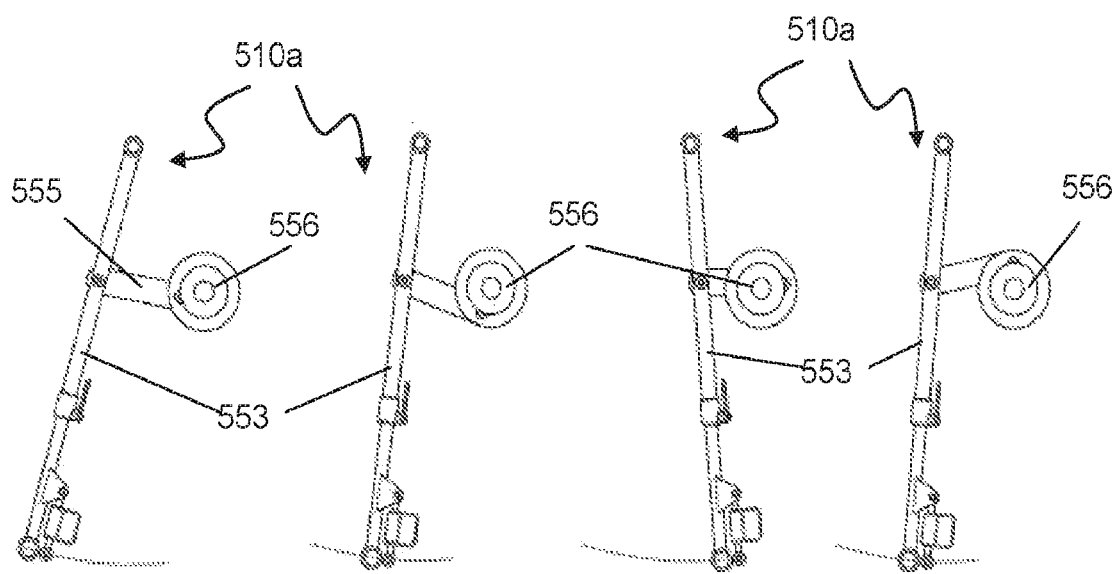
FIG. 34B is a series of side views depicting an arced path of the foot mechanism assembly of FIG. 34B through one stroke.

As shown in FIGS. 32A-33B, drive-wheel and chain assembly 506 is operably coupled to foot mechanism assembly 506 by the pair of leg drive chains 529 which transfer energy from hub assembly 525 to foot mechanism assembly 510. Referring now to FIG. 34A, foot mechanism assembly 510 generally includes two subassemblies (right side and left side) positioned on each side of chair 500, each of which include a leg drive-wheel 556, linkage 555, and a leg link 553. More specifically, and referring to the RS subassembly 510a, the drive chain (not shown) is coupled at a second end to leg drive-wheel 556 of foot mechanism subassembly 510a. Leg drive-wheel 556 is in turn fixedly coupled of linkage 555, which is pivotably coupled at a position along leg link 553. A bottom end of link 553 can be adjustable (or alternatively fixedly) coupled to a foot rest assembly 560 for a user to rest its foot thereon, which will be described in more detail infra. Foot mechanism assembly 510 moves in an arced path as described above with respect to foot mechanism assembly 206, and as depicted FIG. 34B.

Figure 32A:
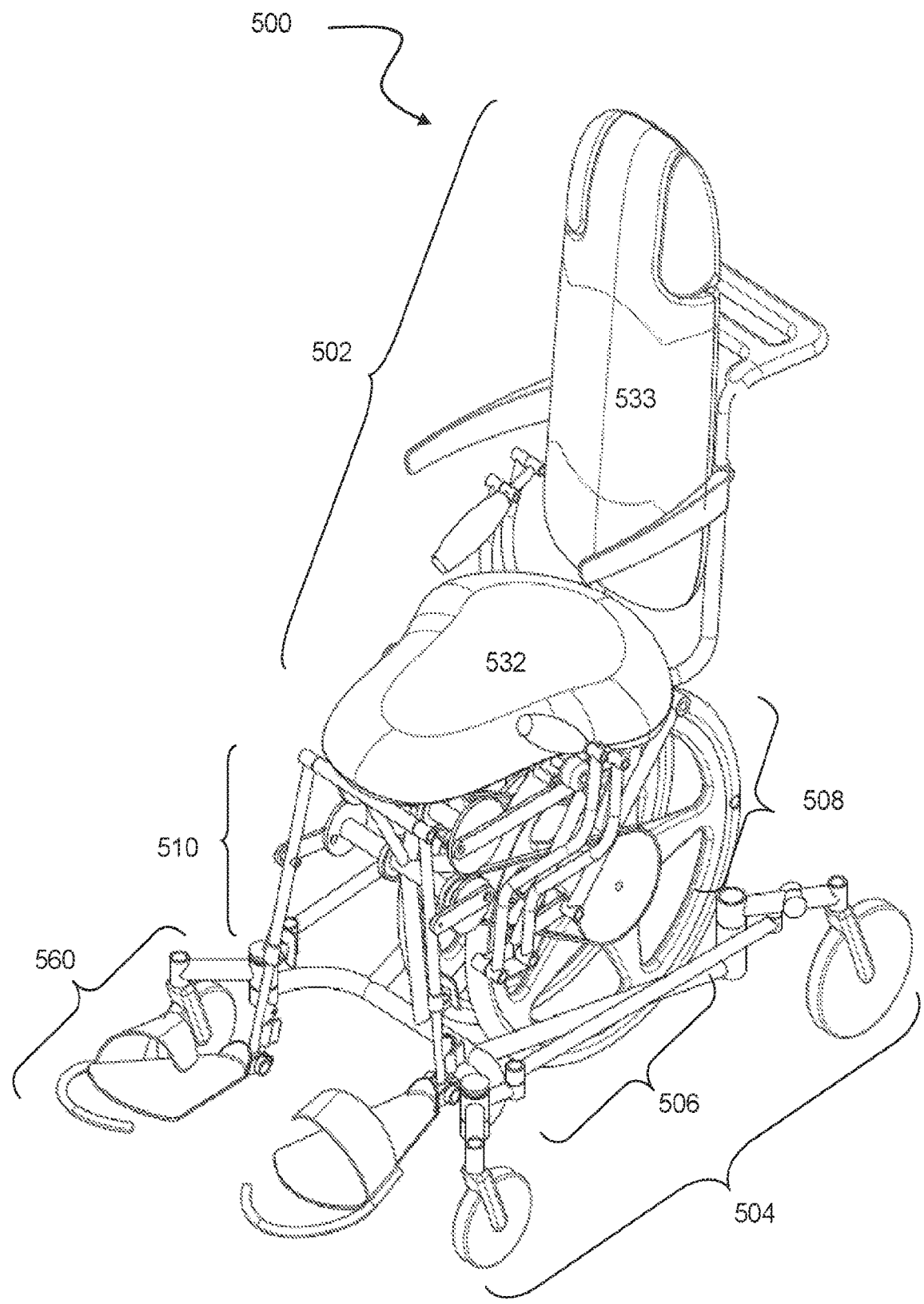
FIG. 32A is a perspective view of the wheelchair of FIG. 31A.
Figure 32B:
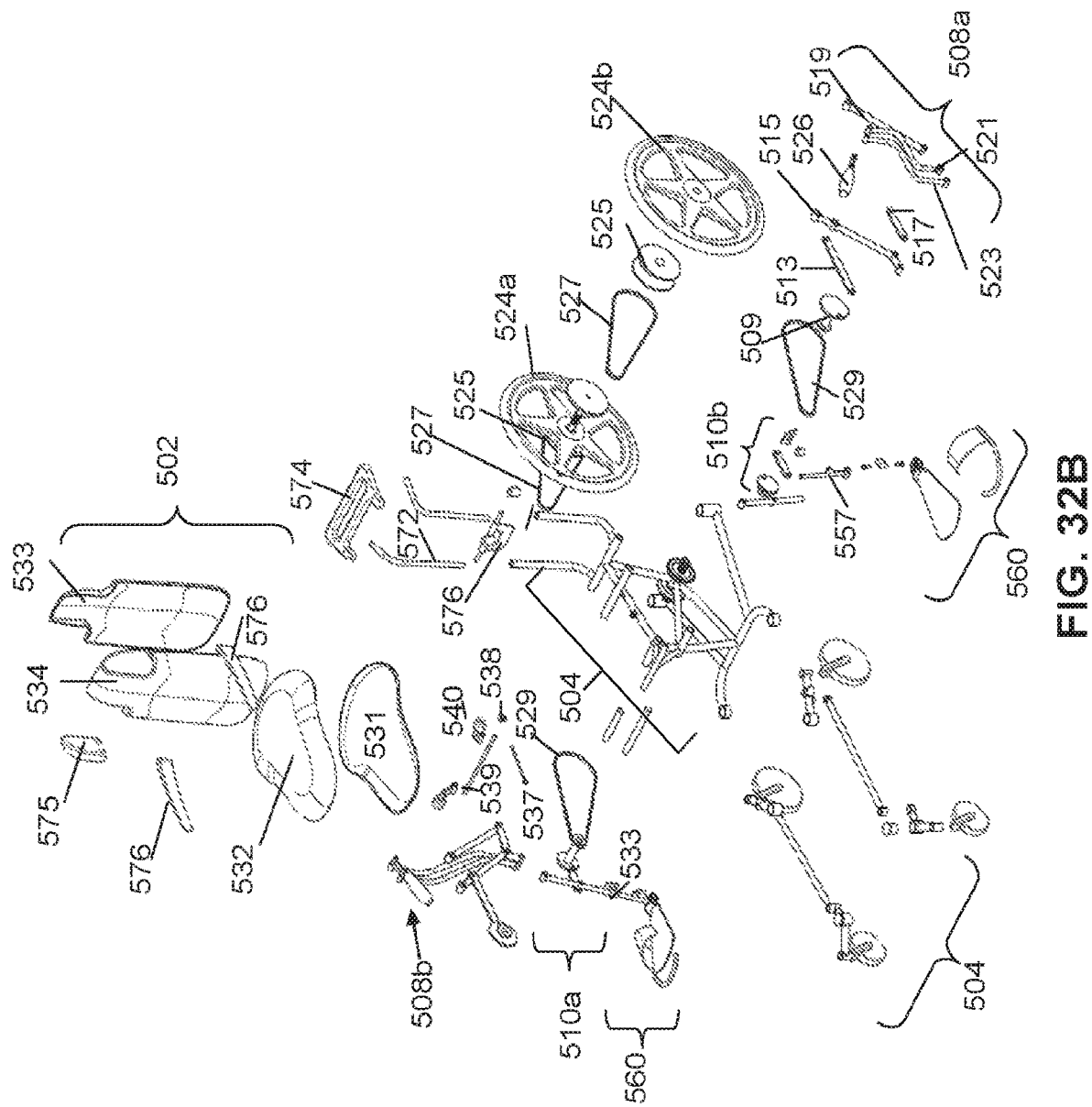
FIG. 32B is an exploded view of the wheelchair of FIG. 32A.
Figure 33A:
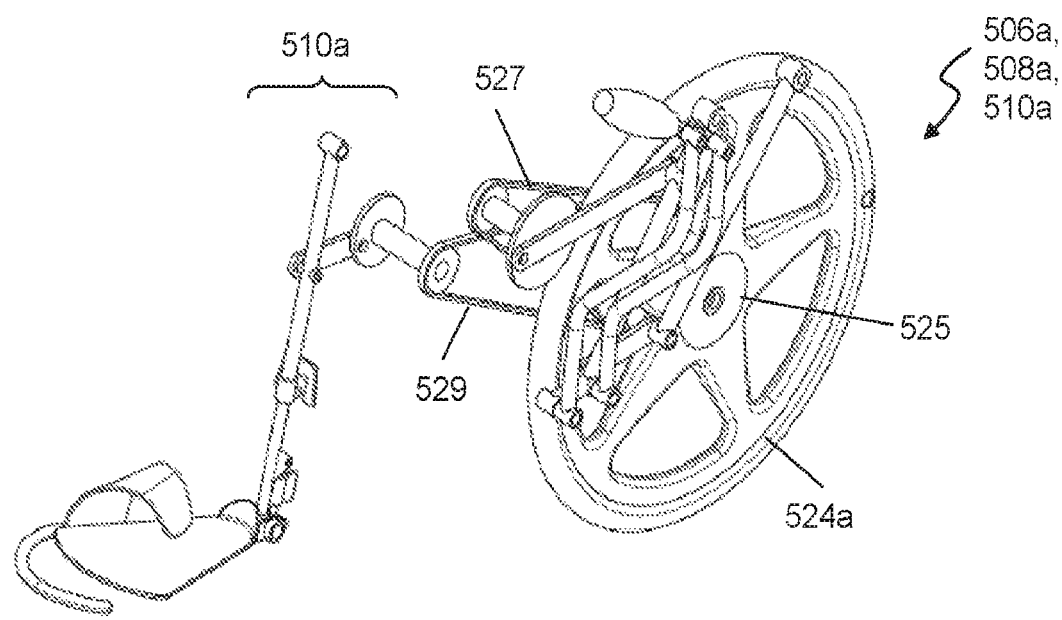
FIG. 33A is a perspective view of an assembled one-half combined foot and hand mechanism assemblies of the wheelchair of FIG. 32A.
Figure 33B:
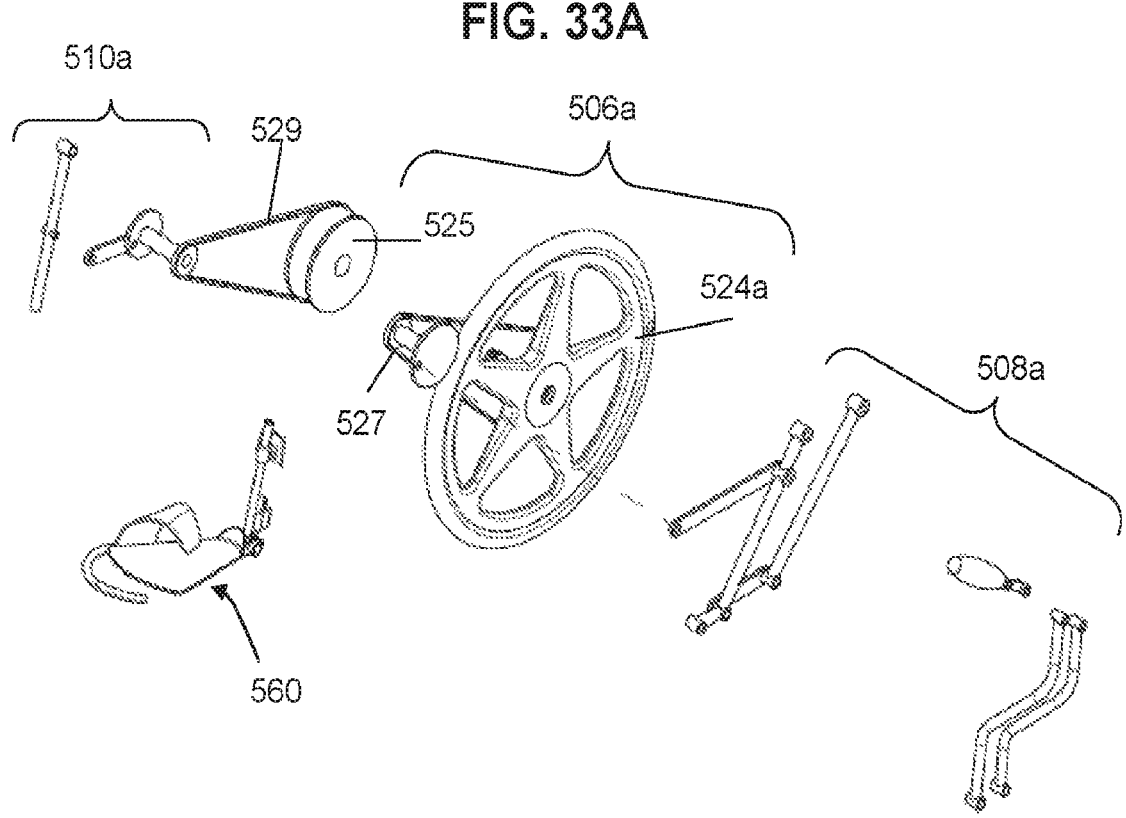
FIG. 33B is an exploded view of the one-half combined foot and hand mechanism assemblies of FIG. 33A.
Figure 33C:
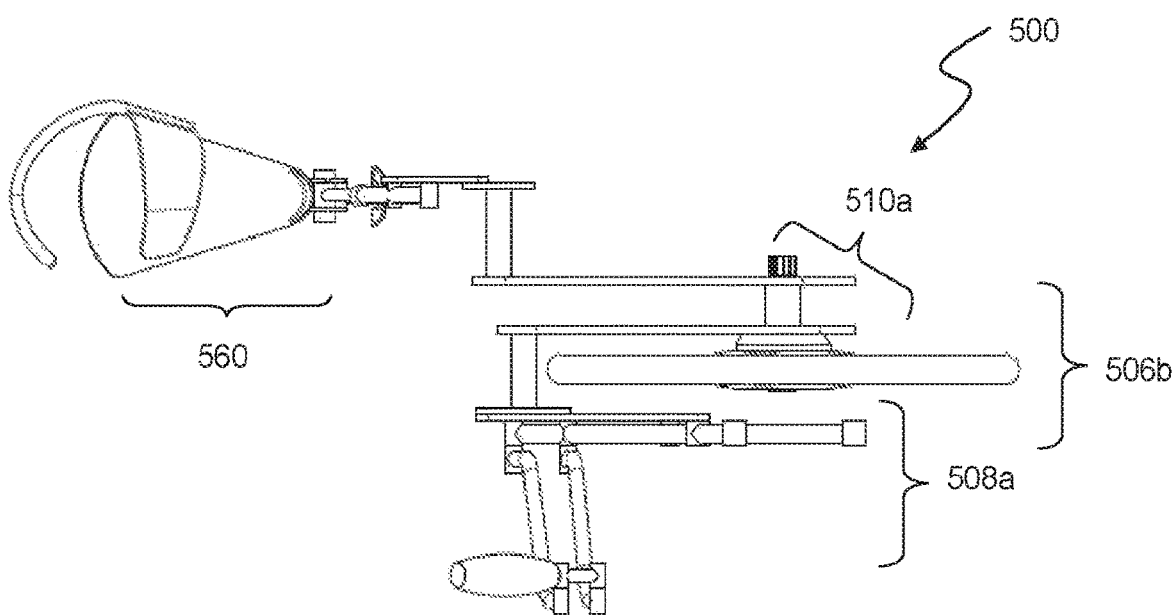
FIG. 33C is a top view of the one-half combined foot and hand mechanism assemblies of FIG. 33A.
Figure 33D:
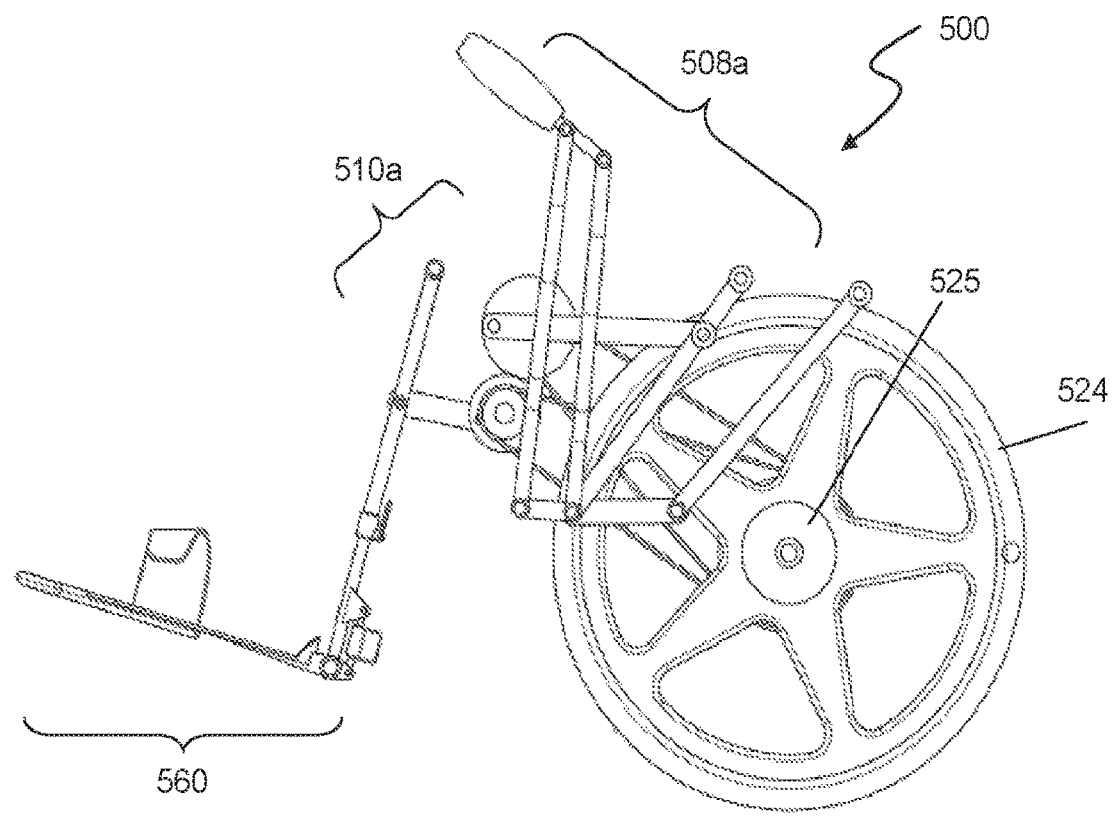
FIG. 33D is a left hand side elevational view of the one-half combined foot and hand mechanism assemblies of FIG. 33A.
Figures 33E, 33F:
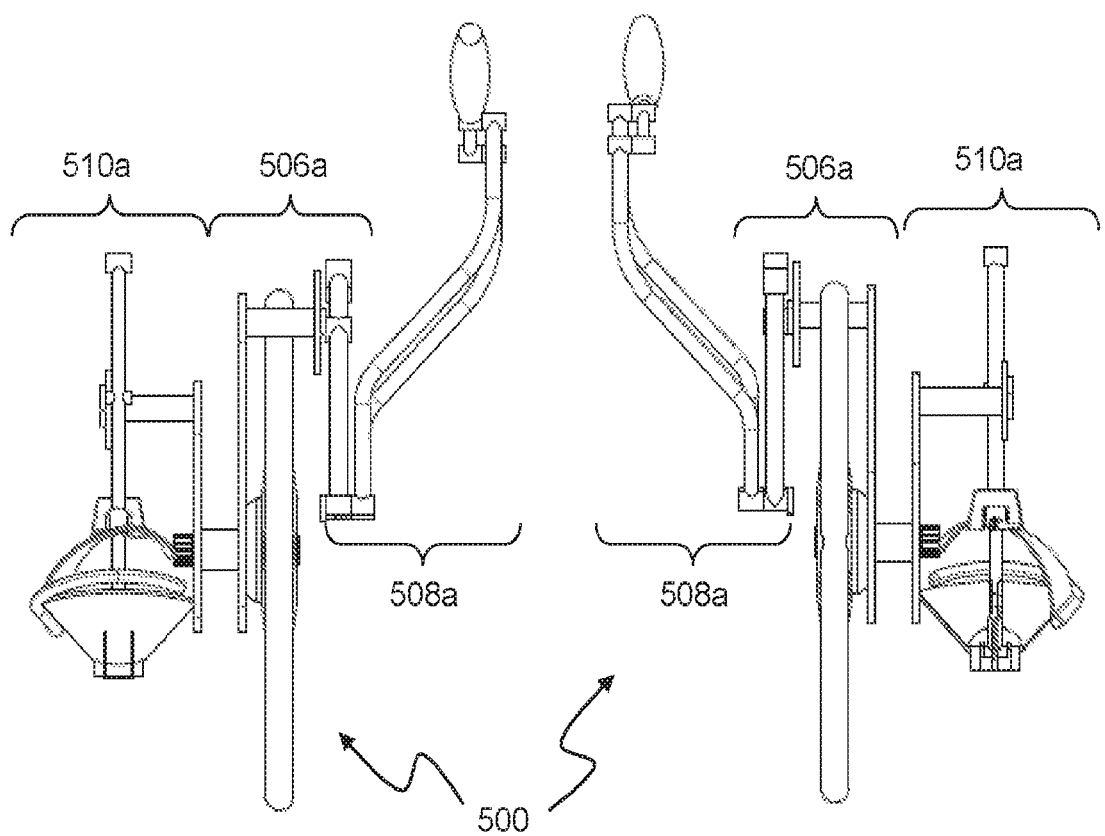
FIG. 33E is a front elevational view of the one-half combined foot and hand mechanism assemblies of FIG. 33A.
FIG. 33F is a rear elevational view of the one-half combined foot and hand mechanism assemblies of FIG. 33A.
Figure 35A:
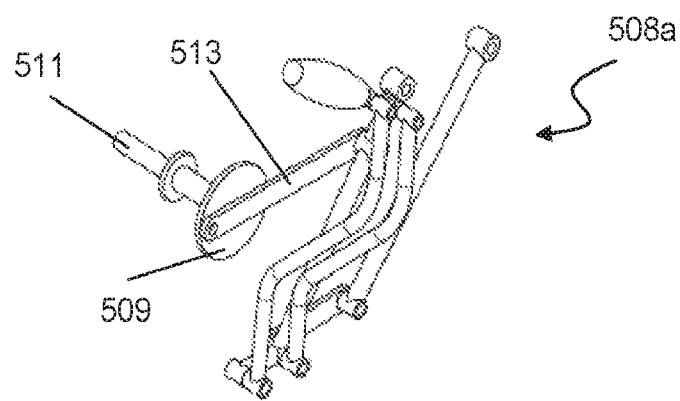
FIG. 35A is a perspective view of an assembled hand mechanism assembly of FIG. 33A.
Figure 35B:
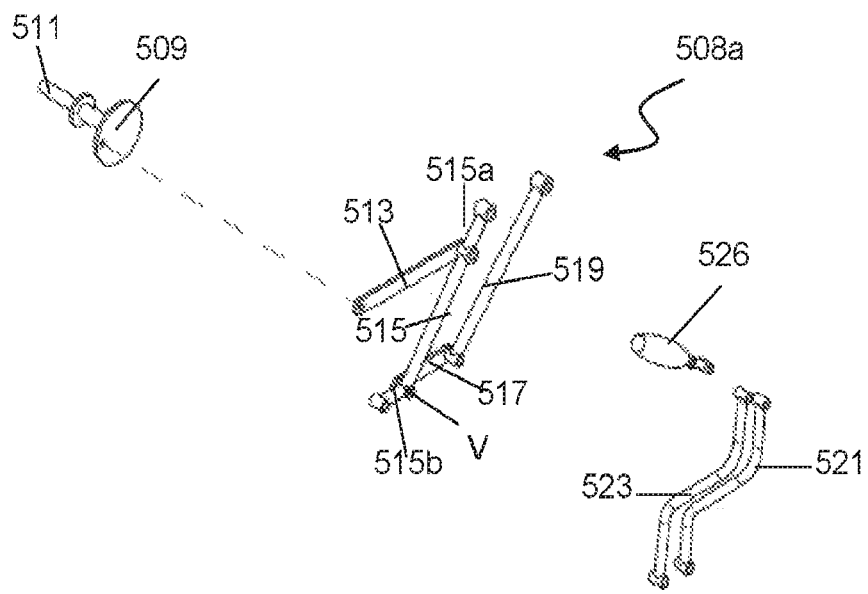
FIG. 35B is an exploded view of the hand mechanism assembly of FIG. 35A.

Now referring to FIGS. 32A and 35A, drive-wheel and chain assembly 506 is also operably coupled to hand mechanism assembly 508 by the pair of arm drive chains 527 which transfer energy from hand mechanism assembly 508 to hub assembly 525. Hand mechanism assembly 508 generally includes two subassemblies (right side and left side) positioned on each side of chair 500. More specifically, and referring to the LS hand mechanism subassembly 508a depicted in FIGS. 35A and 35B, the drive chain (not shown) is coupled at a second end to an arm drive-wheel 509 having an axel 511 that is positioned in front of wheel 524. More specifically, a linkage 513 is fixedly coupled at a first terminal end to drive-wheel 509. A second terminal end of linkage 513 is pivotally coupled to an angled member 515 having a first arm 515a connected to a second arm 515b at a vertex V, forming an obtuse angle. Linkage 513 is coupled near a top portion of first arm 515a. A second linkage 517 is coupled at a first terminal end to the vertex V of angled member 515, and is pivotally coupled at a second terminal end to first terminal end of an arm link 519. A first arcuate grip link 521 is pivotably coupled to the first terminal end of second linkage 517 and vertex V of angled member 515. A second arcuate grip link 523 is pivotably coupled at a first terminal end to a terminal end of second arm 515b of angled member 515. A grip 526 is pivotably coupled to a second terminal end of first and second grip links 521, 523.

Similar to hand mechanism assemblies 204 and 304, in use, this interlinked four-sided geometry follows a curved or arced path causing the angle of grip 526 to adjust to be tangent to the arc path, as depicted in FIG. 36. More specifically, a user grips left hand grip 526 with the user's hand. As force is applied to downward to grip 526, the force causes grip 526 to pivot, which in turn causes grip links 521, 523 to pivot with respect to arm links 515, 519 which in turn causes drive-wheel 509 to rotate via linkage 513 because linkage 513 converts the translational or pivoting motion of interlinked links 515, 519, 521, and 523 into rotational movement of drive-wheel 509. This rotation causes energy to be transferred via axel 511 and drive chain 527 to hub assembly 525. Due to hub assembly 525 being coupled to wheels 524, chair 500 moves forward or backward (depending on the direction of motion of grips 526), and the corresponding connected and opposite foot mechanism subassembly 510a moves in motion with hand mechanism assembly 508a, and vice versa for 510b and 508b, causing a contralateral locomotion. In other words, forcing right grip 526 in forward motion ultimately causes left foot link 553 to swing outwardly, and chair 500 to move forward, and vice versa, mimicking the contralateral movement of walking.

Figure 37A:
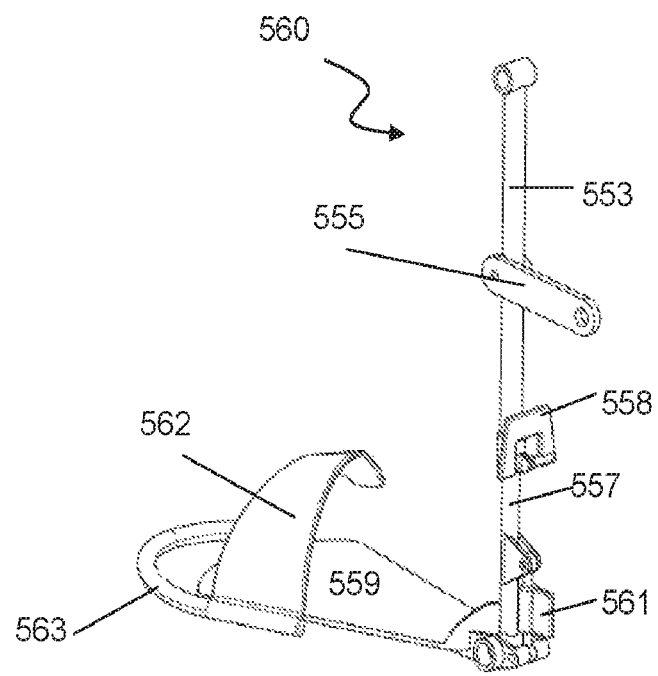
FIG. 37A is a perspective view of an assembled foot rest assembly of FIG. 33A.
Figure 37B:
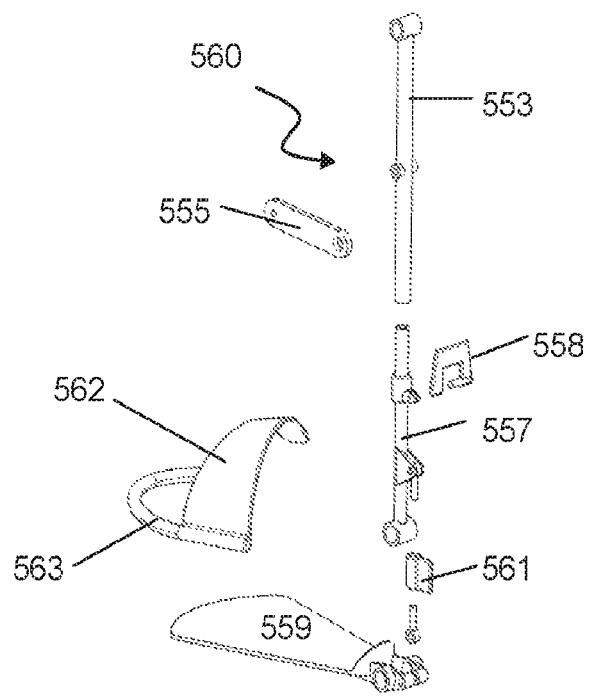
FIG. 37B is an exploded view of the foot rest assembly of FIG. 37A.
Figures 38E, 38F:
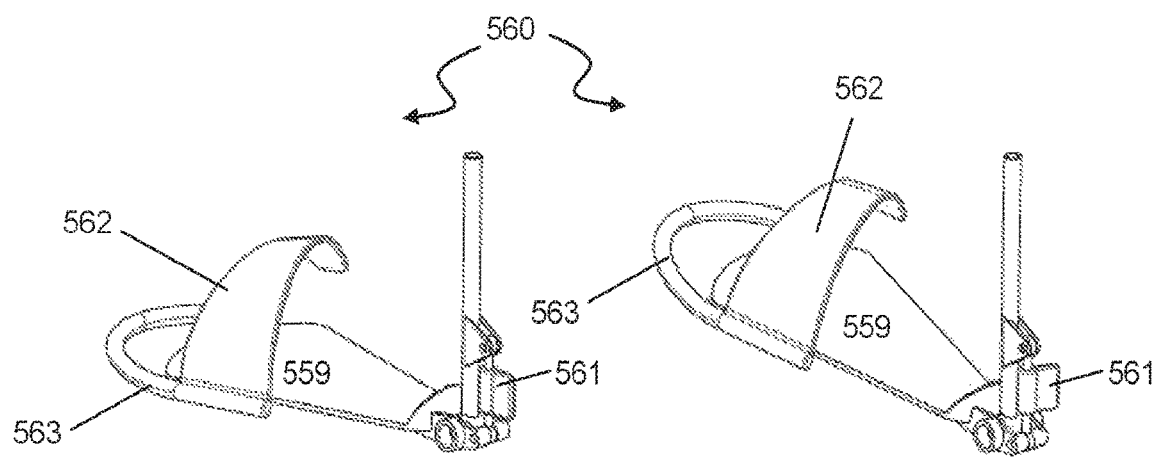
Figures 38G, 38H:
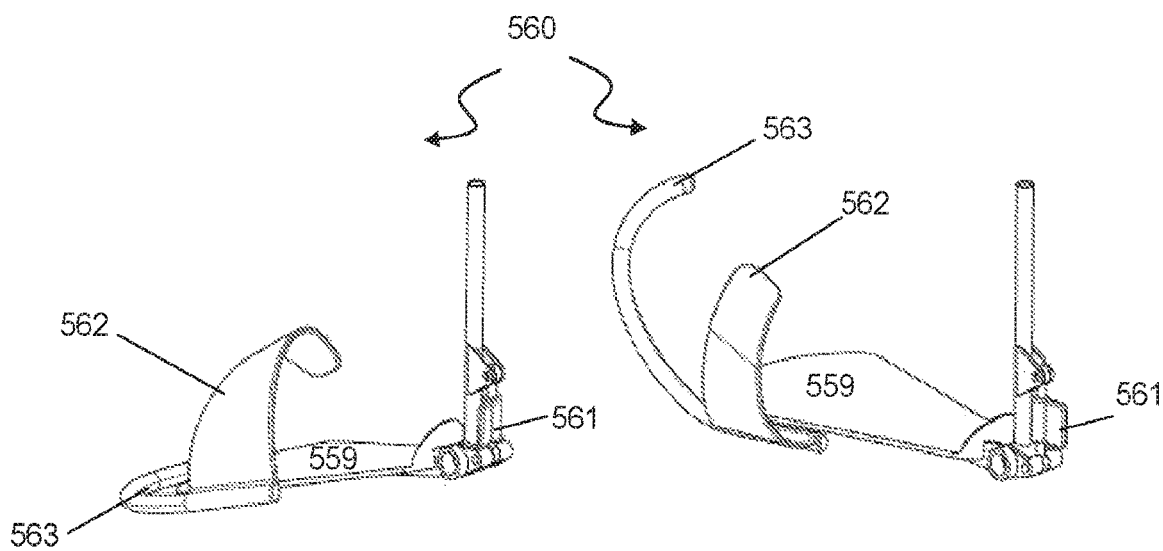
Figure 39:
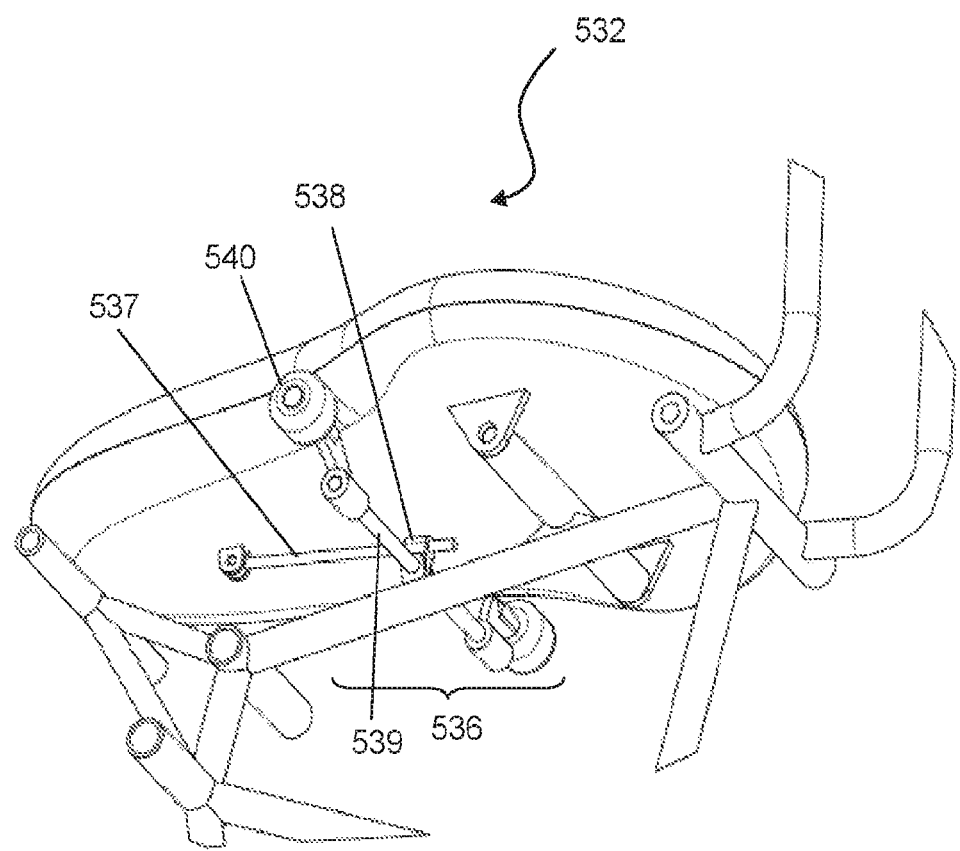
FIG. 39 is a perspective view of a seat adjustment assembly of FIG. 33A.
Figure 40A:
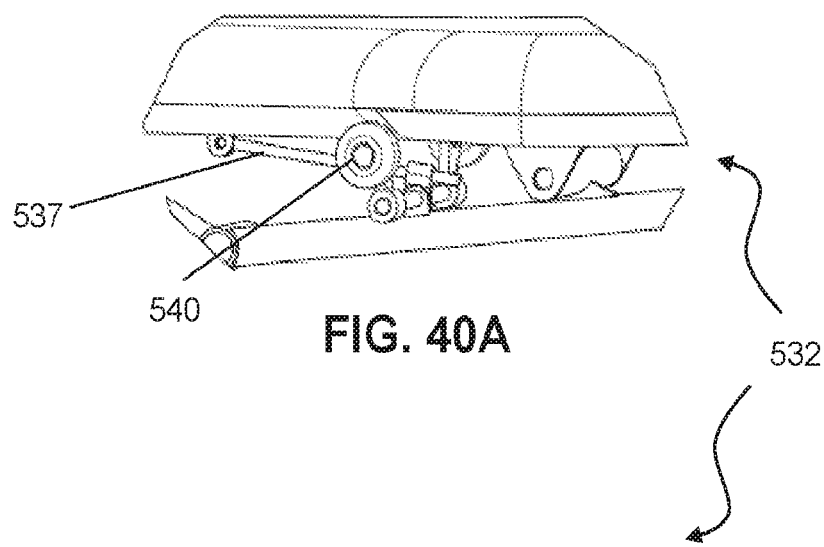
FIG. 40A-40D is a series of perspective and side views depicting seat inclination adjustment of the seat of FIG. 39.
Figure 40B:
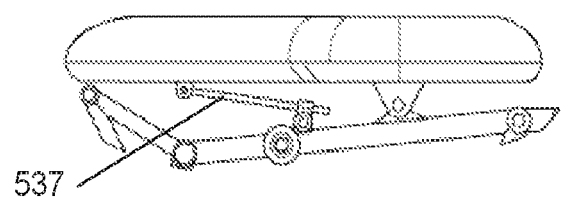
Figure 40C:
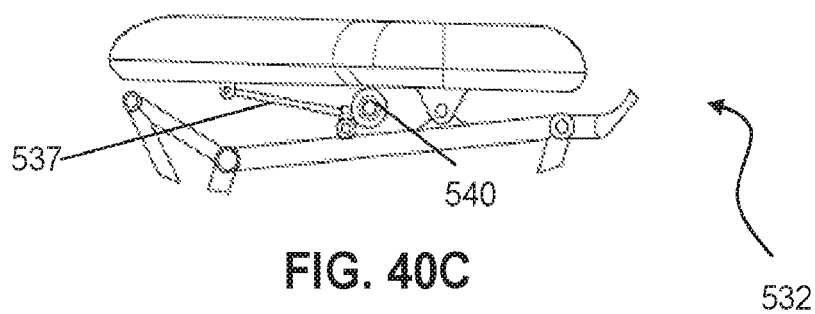
Figure 40D:
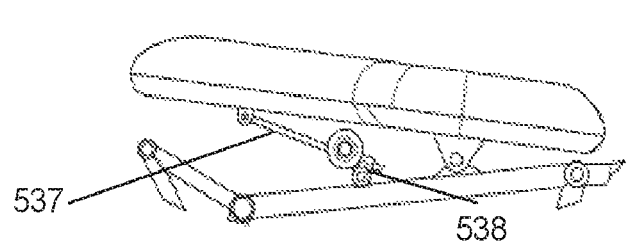
Figure 41:
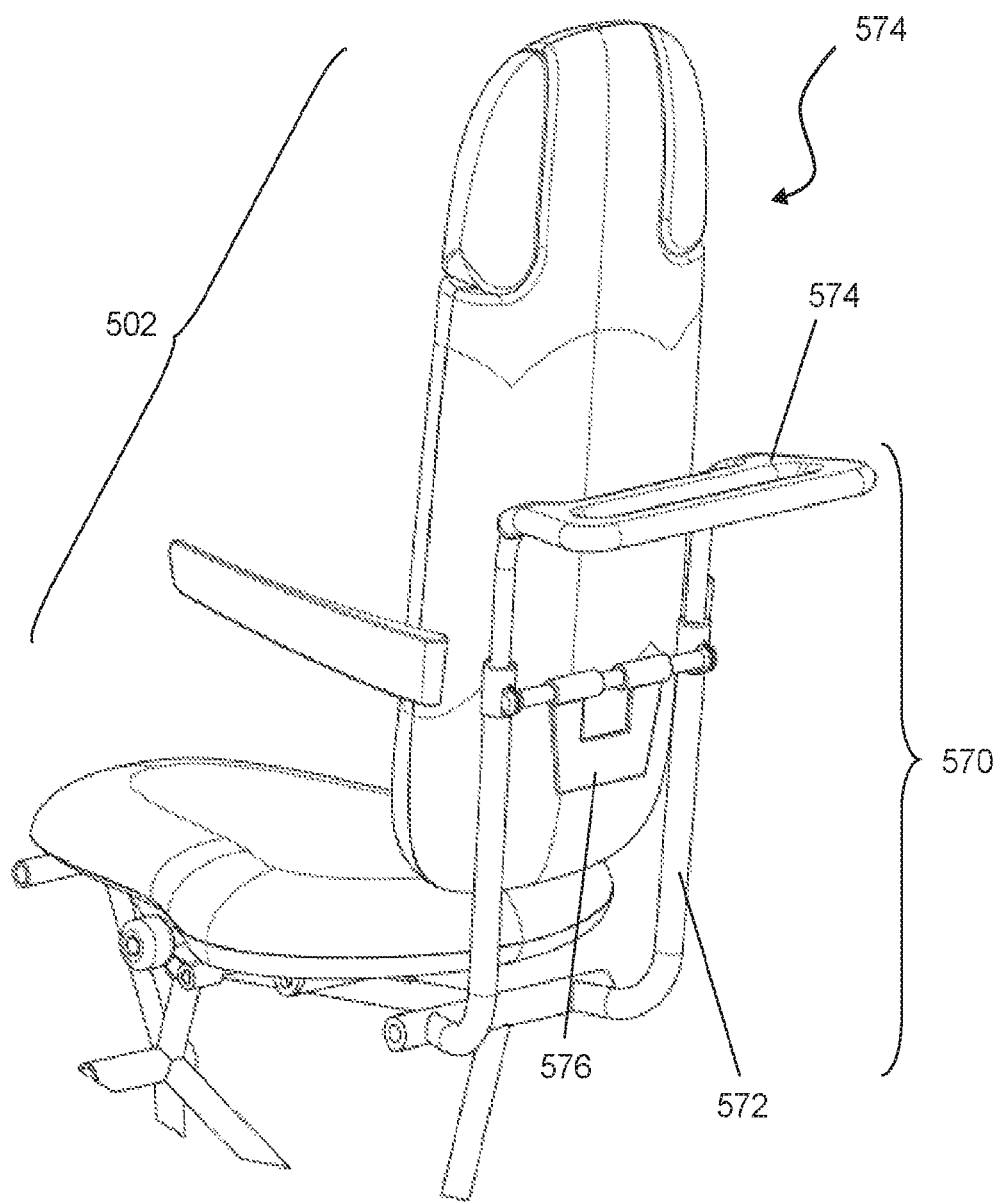
FIG. 41 is a rear perspective view of a seat assembly and handlebar assembly of FIG. 33A.
Figure 43A:
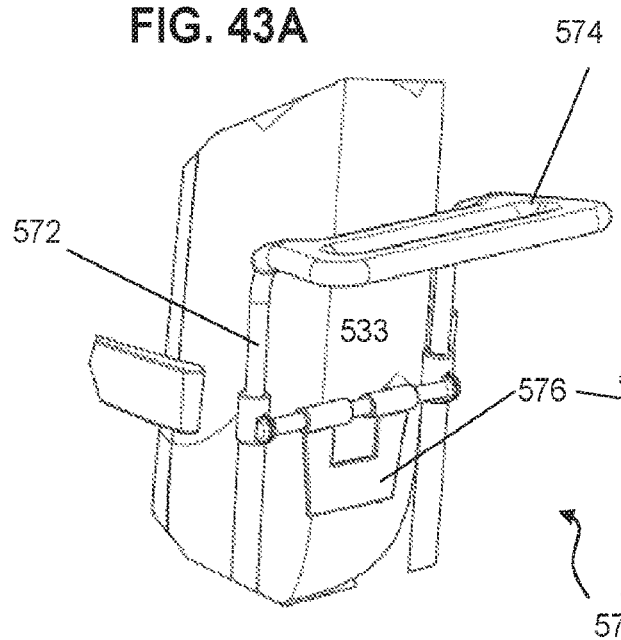
FIGS. 43A-43D is a series of perspective views depicting handlebar height adjustment of the handlebar assembly of FIG. 41.
Figure 43B:
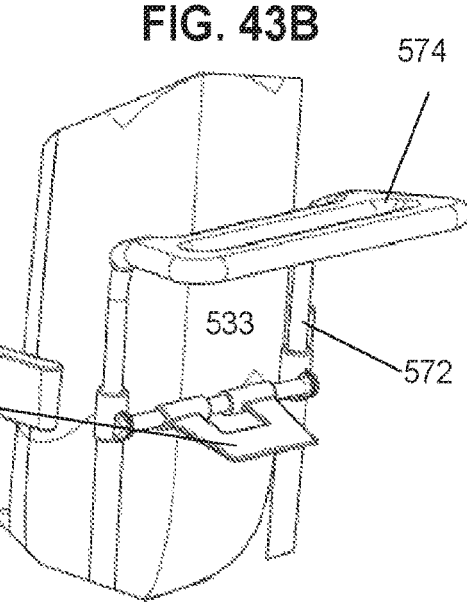
Figure 43C:
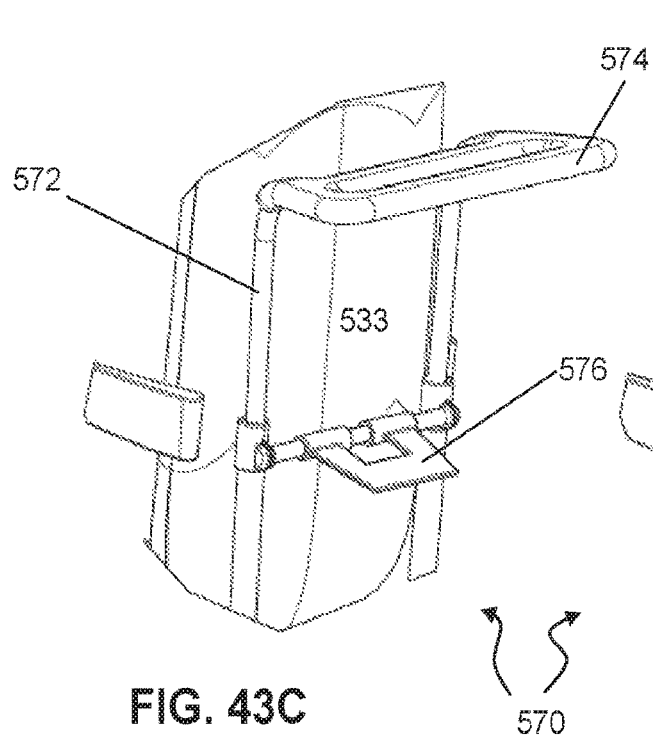
Figure 43D:
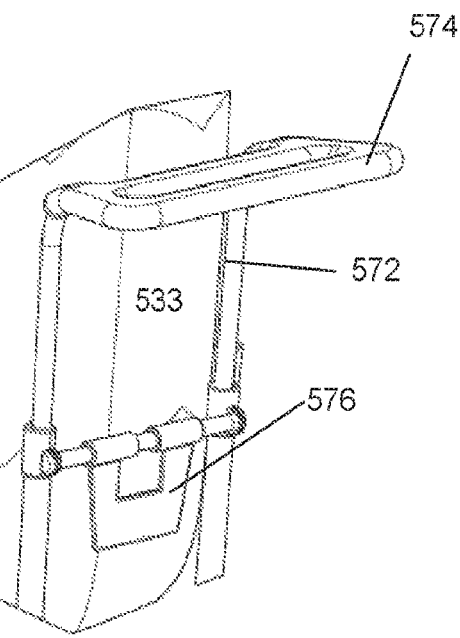

Now referring to FIGS. 37A and 37B, a foot rest assembly 560 can generally include a foot rest link 557, which fits telescopically within leg link 553. Foot rest assembly 560 can be height adjusted by telescoping link 557 within leg link 553 until a desired height is reached as depicted in FIGS. 38A-38D. Pivoting lock lever 558 can then be secured in a vertical position to fix link 557 with respect to leg link 553. To re-adjust, lock lever 558 is moved to a horizontal position to unlock link 557 from leg link 553. A foot rest portion 559 for resting the foot of a user can be pivotably connected to a bottom portion of link 557. Referring to FIGS. 38E-38H, foot rest portion 559 can be coupled to link 557 with at least two degrees of freedom such that an angle of inclination (i.e. pitch) of foot rest portion 559 can be adjusted, and/or foot rest portion 559 can be rotated about link 557 (i.e. yaw). Adjustment tab 561 can be used to adjust foot rest portion 559 with respect to link 557. A foot strap portion 562 and foot rest bar 563 can optionally be present and adjustable to further secure a user's foot to foot rest portion 559.

Referring back to FIGS. 32A and 32B, seat assembly 502 can generally include a seat 532 and a back rest 534, both of which optionally have a molded seat frame 531 and 533, respectively, for additional stability. Referring now to FIGS. 39 and 40A-40D, an inclination of seat 532 is optionally adjustable either manually, automatically (e.g. by incorporating an electric or battery-operated motor), or both. In an embodiment shown in FIGS. 39-40D, seat 532 includes an adjustment assembly 536 including a seat rod 537 fixedly coupled to a bottom of seat 523, and an adjustment mechanism including a seat adjustment web 538, an adjustment handle rod 539, and one or more adjustment knobs 540 coupled to each end of adjustment handle rod 539. As knobs 540 are rotated, rod 539 also rotates, which in turn allows web 538 to translate up or down seat rod 537, thereby adjusting the inclination of seat 532. For example, as web 538 translates toward the end of rod 537, this in turn causes the seat to be pushed upward by rod 537.

Referring now to FIGS. 41 and 42A-42C, a handle assembly 570 can also be incorporated. Handle assembly 570 can be couple to seat assembly 502 via a tubular frame assembly 572. Handle assembly 570 can include a height adjustable handle bar 574 that telescopes within frame assembly 572. Referring to FIGS. 43A-43D, handle bar 574 can be adjusted by rotating handle lock 576 to an outward position. When the desired height is determined, the handle lock 576 is pushed downwardly until it is flush with back rest 534 to lock the handle bar 574 relative to frame assembly 572.

Referring now to FIGS. 44A-44D, back rest 534 can include one or more finials 575. In embodiments, finials 575 can shift between a substantially vertical position in which they are flush with back rest 534, and a substantially horizontal position in which they extend outwardly from back rest 534 for use as an additional handle option, or for added comfort and/or stability to a user.

Referring to FIGS. 45A-45D, back rest 533 can further include on or more adjustable arms or wings 576. Wings 576 can independently shift between a first position in which they are substantially perpendicular to back rest 533 to be used as arms, and a second position in which they are substantially parallel to back rest 533. This allows the user more flexibility to rotate in seat 532, and can help secure the user on seat 532.

Figure 48A:
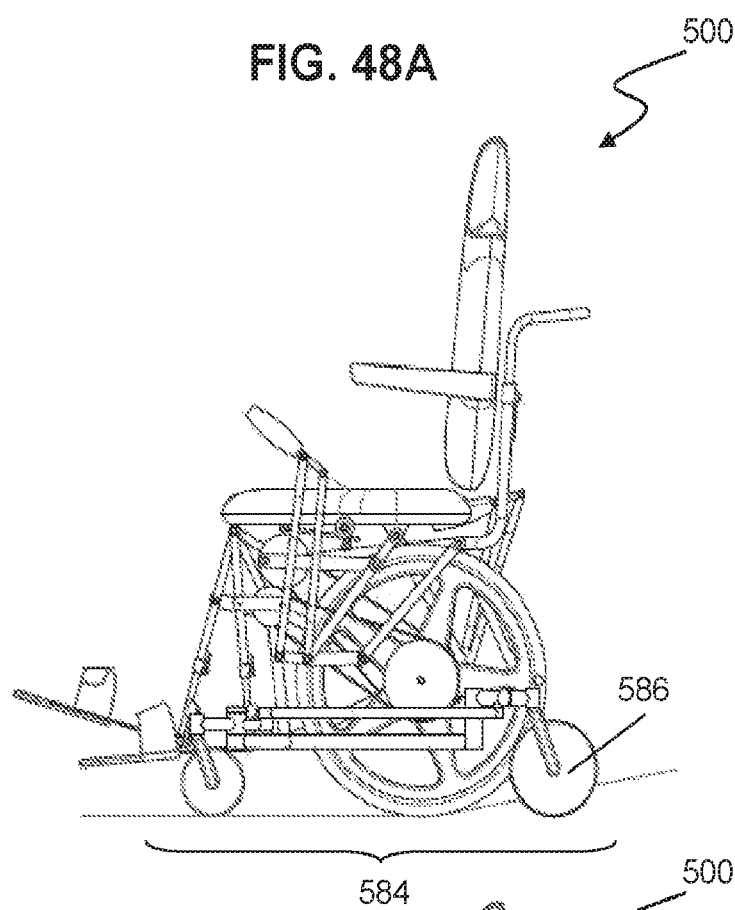
FIGS. 48A and 48B are left hand side views of the wheelchair of FIG. 33A on an inclined surface.
Figure 48B:
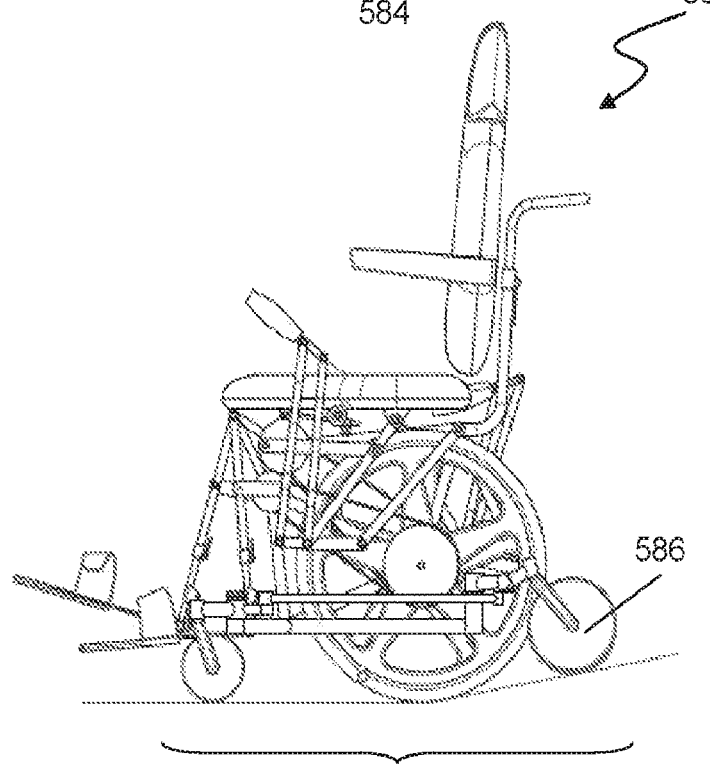

Referring now to FIGS. 46A-47B, stability frame assembly 504 generally includes a plurality of foldable tubular frame members which provides support and to seat assembly 502. As mentioned previously, a portion of frame assembly 504 is connectable to handle assembly 570 at a rear portion 580 and can comprise a U-shaped upright section. A mid portion 582 generally provides support for seat assembly 530, and to which the adjustment mechanism of seat adjustment assembly 536 is fixed. A bottom frame portion 584 includes a rectangular frame, and at each corner, an anti-tip or stability wheel 586 is pivotably coupled to the frame portion 584 via pivot couplers 583. As shown in FIGS. 48A and 48B, wheels 586 provide additional stability to chair 500 when moving up and down inclined surfaces.

Referring to FIGS. 47C-47F, the tube members of frame assembly 572 are preferably pivotably coupled to one another such that anti-tip wheels 586 and bottom frame portion 584 can be folded inwardly toward a center of chair 500 when not in use or during transport or starge. This allows chair 500 to be vertically foldable to aid in transporting from one location to another in a vehicle or other means. When desired, frame portion 584 and wheels 586 can be folded outwardly which lends to a wider base for chair 500 than seat assembly 502 as shown in FIGS. 48A and 48B. Such pivotable connections between tube members can be accomplished via pivoting joint members 586 as depicted in FIGS. 46a and 46B.

Figure 50:
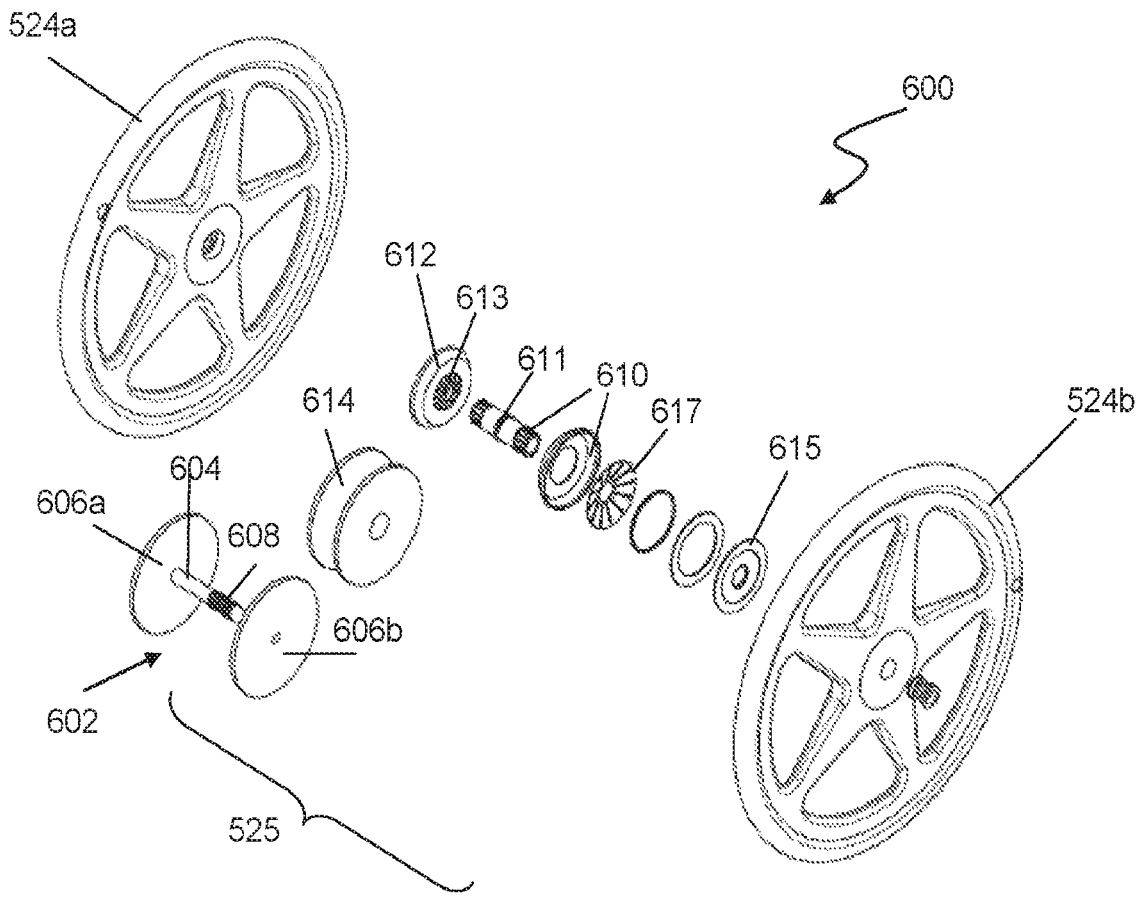
FIG. 50 is an exploded view of the assembly of FIG. 49A.
Figure 51:
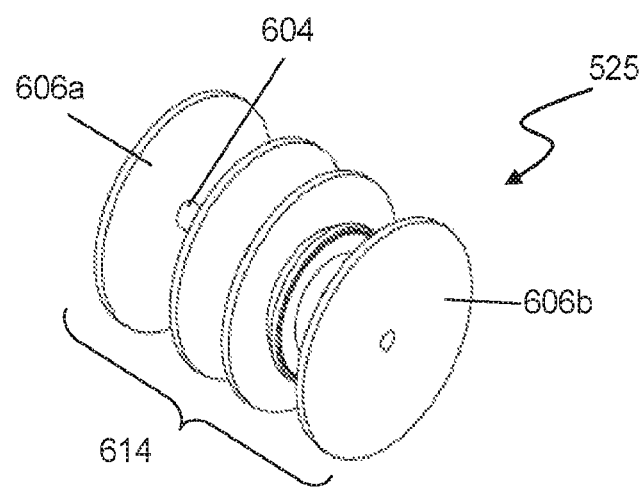
FIG. 51 is a perspective view of the hub assembly of FIG. 49A.
Figure 52A:
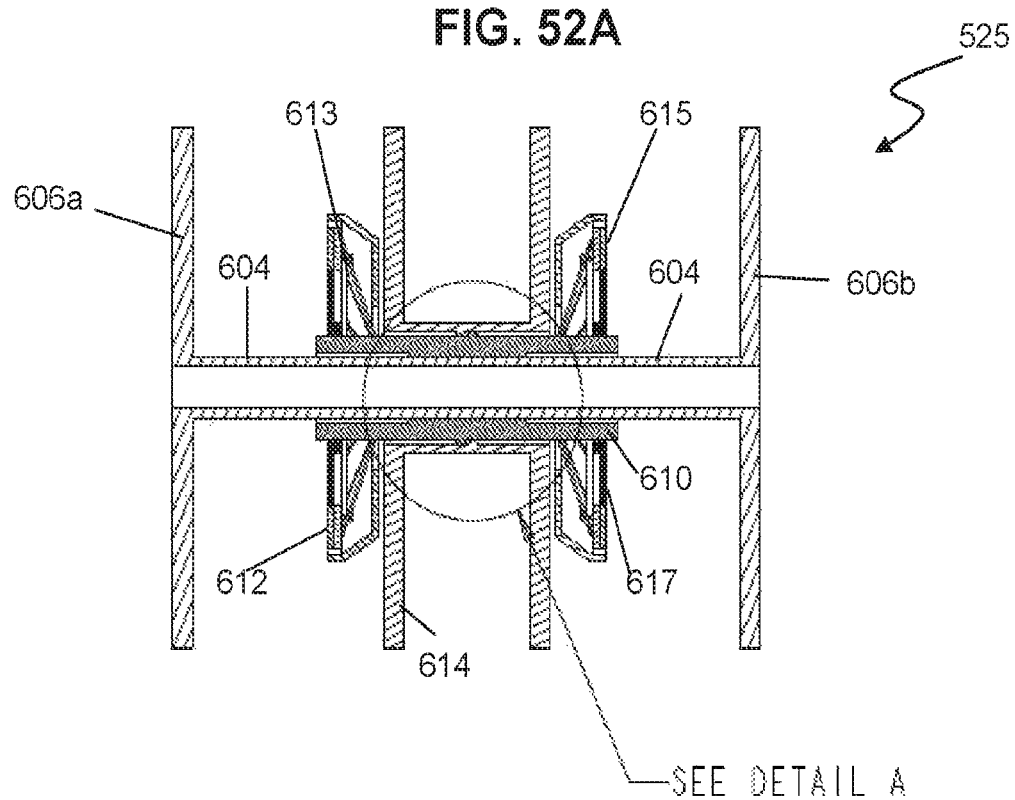
FIG. 52A is a cross-sectional view of the hub assembly of FIG. 51 in an equilibrium configuration.
Figure 52B:
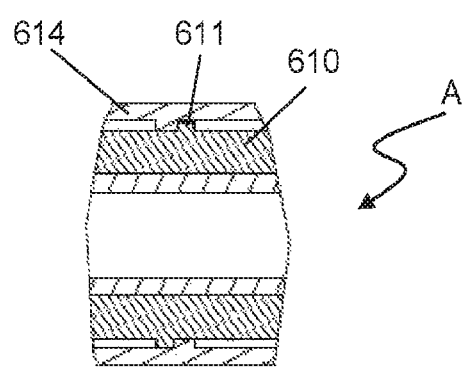
FIG. 52B is a sectional view of FIG. 52A at "A".
Figure 53A:
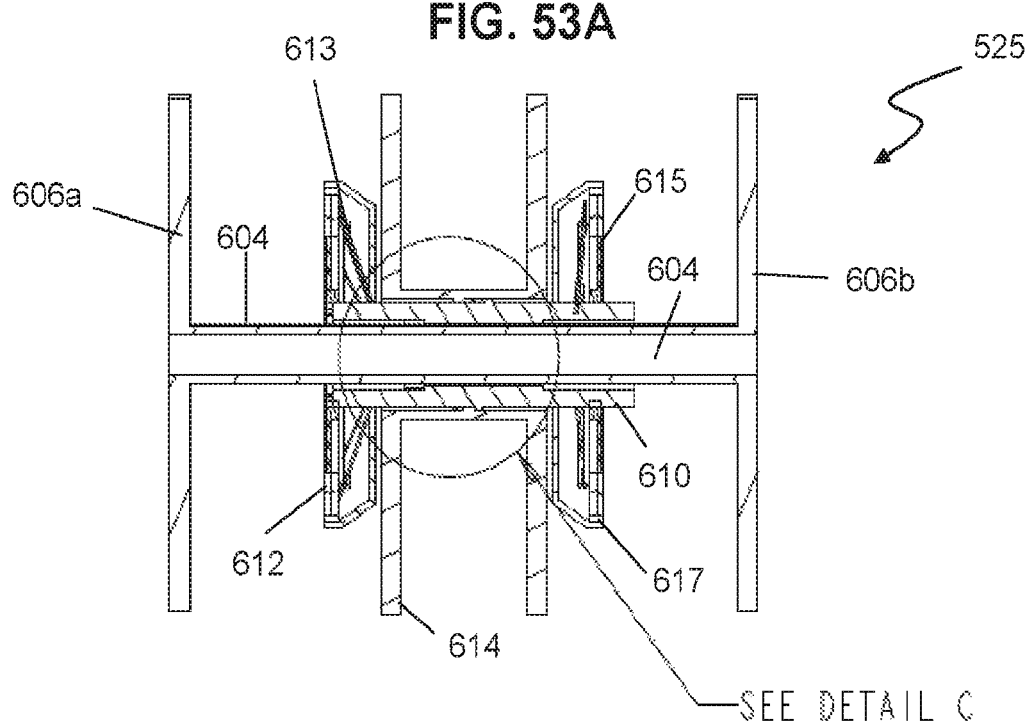
FIG. 53A is a cross-sectional view of the hub assembly of FIG. 51 in a disengaged configuration.
Figure 53B:
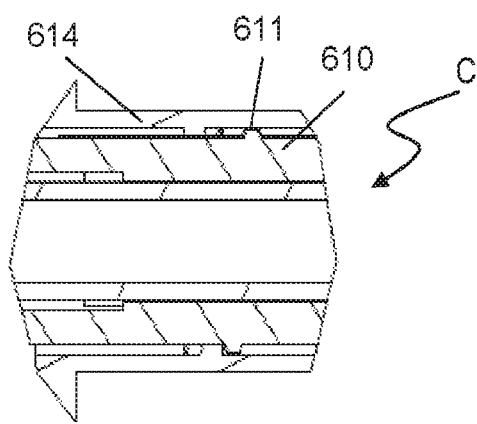
FIG. 53B is a sectional view of FIG. 53A at "C".

Now referring to FIGS. 49A-54B, movement of chair 500 is controlled by a dual clutch transmission assembly 600. Dual clutch transmission assembly 600 generally includes hub assembly 525 and two wheels 524 coupled to hub assembly 525. Referring to FIGS. 50 and 51, hub assembly 525 includes an inner first hub 602 formed of an axel 604 and a drive wheel 606 fixedly coupled to each end of axel 604. Axel 604 includes structure defining a spline 608. Clutch drive 610 covers a portion of axel 604, and includes structure defining an acme thread 611 in a center of clutch drive 610. Clutch drive 610 is radially fixed to axel 604 via spline 608 such that it turns with axel 604. A left clutch plate 612 is coupled to a first end (left end) of clutch drive 610 and is radially fixed to clutch drive 610. A diaphragm spring 613 is sandwiched between left clutch plate 612 and clutch drive 610. Wheel 524a is sandwiched between left clutch plate 612 and left drive wheel 606a, and is operably coupled to clutch drive 610 at an end thereof.

A second hub 614 is radially fixed to clutch drive 610 via thread 611 (an internal surface of hub 614 includes structure defining a corresponding threading (not shown) to engage threading 611. A right clutch plate 615 is radially fixed to clutch drive 610 at a second (right end) of clutch drive 610. A second diaphragm spring 617 is sandwiched right clutch plate 615 and clutch drive 610, and a second wheel 524b is sandwiched between right clutch plate 615 right drive wheel 606b, and is operably coupled to clutch drive 610 at an end thereof.

Referring now to FIGS. 52A-53B, in use, inner first hub 602 is driven by the left arm (via the LS hand mechanism assembly as described herein) which in turn drives the right leg (via the RS foot mechanism assembly as described herein). Second hub 614 is driven by the right arm (via the RS hand mechanism assembly as described herein) which in turn drives the left leg (via the LS foot mechanism assembly as described herein). When inner first hub 602 and outer second hub 614 are turning equally, clutch drive 610 remains engaged with both, allowing contralateral locomotion in the forward or backward direction. In the event the outer second hub 614 is moved slower than inner first hub 602 (i.e. by moving the grip on one side only), clutch drive 610 moves to the right and compresses diaphragm spring 617 (FIG. 53A) until clutch drive 610 is unthreaded from hub 614 and disengages hub 614 (FIG. 53B) and wheel 524b, thereby stopping rotation of wheel 524b. To re-engage clutch drive 610, wheel 524a is moved in the reverse direction until clutch drive 610 is reengaged with hub 614. Contralateral locomotion is then re-established when clutch drive 610 is centered. However, if clutch drive 610 moves too far left, it will similarly depress diaphragm 613 until clutch drive 610 disengages hub 612 and wheel 524a, stopping motion of wheel 524a. Forward motion of wheel 524b then reengages clutch drive 610 to re-establish contralateral locomotion. Therefore, the clutch drive 610, when centered, ensures 180 degree positioning of RS foot mechanism assembly/LS hand mechanism assembly to LS foot mechanism assembly/RS hand mechanism assembly for contralateral locomotion. Through the use of opposing diaphragm springs 613, 617, clutch drive 610 is forced to be centered and contralateral movement equilibrium is reached.

Dual clutch transmission assembly 600 can be incorporated into any embodiment of the invention as described, as the inner hub is connected to the LS hand mechanism assembly by chain 527b and RS foot mechanism assembly by chain 529a, and outer hub is connect to the RS hand mechanism assembly by chain 527a and LS foot mechanism assembly by chain 529b.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A wheelchair configured to impart motion on one or more lower extremities of a user to inhibit inelasticity in joints of the one or more lower extremities as a result of extended immobility, and to promote a natural alignment of one or more upper extremities of the user during manipulation of the wheelchair, the wheelchair comprising:
   a seat assembly comprising a seat and a backrest;
   two ground-engaging wheels;
   a hub assembly including a first drive-wheel and a first chain, and a second drive-wheel and a second chain, the first drive-wheel being operably coupled to the second drive-wheel;
   a hand mechanism assembly including a first arm drive-wheel operably coupled to the first drive-wheel via the first chain, the first arm drive-wheel being configured to be operated using a first upper extremity of a user; and
   a foot mechanism assembly including a first leg drive-wheel operably coupled to the second drive-wheel via the second chain, the first leg drive-wheel being configured to impart motion of a first lower extremity of the user on a side opposite the first upper extremity used to operate the hand mechanism assembly,
   wherein the wheelchair is configured such that actuation of the first arm drive-wheel of hand mechanism assembly by the upper extremity actuates the first leg drive-wheel of the foot mechanism assembly to impart the motion on the first lower extremity, and causes one of the ground-engaging wheels to rotate, thereby resulting in contralateral locomotion, and
   wherein the hand mechanism assembly further comprises a first linkage fixedly coupled to the first arm drive-wheel, at least one elongate grip link pivotably coupled at a first end, either directly or indirectly, of the first linkage, and a grip coupled to a second end of one of the at least one elongate grip links, the grip being configured to be moved when force is applied thereto by the first upper extremity of the user, wherein the first linkage converts translational movement of the grip into rotational movement of the first arm drive-wheel.

2. The wheelchair of claim 1, wherein the hand mechanism assembly comprises rotation of the first arm drive-wheel by one of a right hand or a left hand of the user, which actuates the first leg drive-wheel of the foot mechanism assembly to impart motion of the other of a right leg or left leg of the user.

3. The wheelchair of claim 1, wherein the foot mechanism assembly further comprises a footrest operably coupled to the first leg drive-wheel, and wherein rotation of the first leg drive-wheel imparts one of a linear or arcing motion on the footrest, thereby allowing the lower extremity of the user to swing back and forth.

4. The wheelchair of claim 1, wherein the foot mechanism assembly further comprises a second linkage fixedly coupled to the first leg drive-wheel, a leg link coupled to the second linkage at a first end, and a foot rest coupled to a second end of the leg link, wherein the second linkage converts rotational movement of the first leg drive-wheel into translational movement of the leg link and foot rest.

5. The wheelchair of claim 4, wherein the foot rest is adjustable along a longitudinal axis of the leg link and/or about the longitudinal axis of the leg link.

6. The wheelchair of claim 1, wherein the hub assembly further comprises a third drive-wheel and a third chain, and a fourth drive-wheel and a fourth chain, the third drive-wheel being operably coupled to the fourth drive-wheel;
   wherein the hand mechanism assembly further comprises a second arm drive-wheel operably coupled to the third drive-wheel via the third chain, the second arm drive-wheel being configured to be operated using a second upper extremity of a user on a side opposite the first upper extremity;
   wherein the foot mechanism assembly further comprises a second leg drive-wheel operably coupled to the fourth drive-wheel via the fourth chain, the second leg drive-wheel being configured to impart motion of a second lower extremity of the user on a side opposite the second upper extremity used to operate the hand mechanism assembly, wherein the wheelchair is further configured such that actuation of the second arm drive-wheel of the hand mechanism assembly by the second upper extremity actuates the second leg drive-wheel of the foot mechanism assembly to impart the motion on the second lower extremity, and causes the other of the at least one of the ground-engaging wheels to rotate, thereby resulting in contralateral locomotion.

7. The wheelchair of claim 6, wherein the hand mechanism assembly further comprises a third linkage fixedly coupled to the second arm drive-wheel, at least one elongate grip link pivotably coupled at a first end, either directly or indirectly, to the third linkage, and a grip coupled to a second end of one of the at least one elongate grip links, the grip being configured to be moved when force is applied thereto by the second upper extremity of the user, wherein the third linkage converts translational movement of the grip into rotational movement of the second arm drive-wheel.

8. The wheelchair of claim 6, wherein the foot mechanism assembly further comprises a fourth linkage fixed coupled to the second leg drive-wheel, a leg link coupled to the fourth linkage at a first end, and a foot rest coupled to a second end of the leg link, wherein the fourth linkage converts rotational movement of the second leg drive-wheel into translational movement of the leg link and foot rest.

9. The wheelchair of claim 6, wherein the first drive-wheel of the hub assembly is fixedly coupled to a first end of a first axel, and the second drive-wheel is fixedly coupled to a second end of the axel, thereby defining an inner hub, and wherein the third drive-wheel of the hub assembly is fixedly coupled to a first end of a second axel, and the fourth drive-wheel is fixedly coupled to a second end of the second axel, thereby defining an outer hub, wherein the outer hub is operably coupled to the inner hub such that the second axel covers a portion of the first axel of the inner hub, and the third and forth drive-wheels are positioned between the first and second drive-wheels.

10. The wheelchair of claim 9, wherein the inner hub is operably coupled to the outer hub via a clutch drive positioned radially over the axel of the inner hub, and between the axels, wherein the clutch drive is configured to engage the inner hub and outer hub to rotate both simultaneously, and configured to disengage the inner hub from the outer hub for independent rotation.

11. The wheelchair of claim 10, wherein the axel of the inner hub comprises structure defining a spline on the outer surface thereof, and wherein the clutch drive engages the spline to rotate with the inner hub.

12. The wheelchair of claim 11, wherein a portion of the outer surface of the clutch drive includes structure thereon defining a thread, and wherein an inner surface of the axel of the outer hub includes structure thereon defining a corresponding thread, wherein the hub assembly is configured such that when the threads of the clutch drive and the outer hub are engaged, the outer hub rotates with the clutch drive and the inner hub, and when the threads are disengaged, the inner hub rotates with the clutch drive and the outer hub does not rotate with the clutch drive.

13. The wheelchair of claim 10, wherein the first and second ground-engaging wheels are operably coupled to the clutch drive, wherein the first ground-engaging wheel is positioned between the first drive-wheel of the inner hub and the third drive-wheel of the outer hub, and the second ground-engaging wheel is positioned between the second drive-wheel of the inner hub and the fourth drive-wheel of the outer hub, and wherein the first and second drive.

14. The wheelchair of claim 13, wherein when the clutch drive is disengaged, only one of the first and second ground-engaging wheels rotates, wherein when the clutch drive is engaged, both of the first and second ground-engaging wheels rotates.

15. The wheelchair of claim 6, wherein the wheelchair is configured such that when the first lower extremity is extended in a forward position, the second lower extremity is in a bent, unextended position, and vice versa.

16. The wheelchair of claim 1, wherein the seat assembly is configured such that an inclination of the seat can be adjusted independently of the backrest.

17. The wheelchair of claim 1, further comprising a foldable base frame, the base frame comprising a rectangular frame comprising at least four members, each member being pivotably coupled to an adjacent member, and further comprising an anti-tip wheel coupled to each corner of the rectangular frame.

18. The wheelchair of claim 17, wherein the foldable base frame is configured to fold inwardly toward a center of the wheelchair.

19. A wheelchair configured to impart motion on one or more lower extremities of a user to inhibit inelasticity in joints of the one or more lower extremities as a result of extended immobility, and to promote a natural alignment of one or more upper extremities of the user during manipulation of the wheelchair, the wheelchair comprising:
  a foldable base frame, the base frame comprising a rectangular frame comprising at least four members, each member being pivotably coupled to an adjacent member, and further comprising an anti-tip wheel coupled to each corner of the rectangular frame;
  a seat assembly comprising a seat and a backrest;
  two ground-engaging wheels;
  a hand mechanism assembly including a hand grip on each side of the seat assembly, the hand mechanism assembly being operably coupled to the ground-engaging wheels to rotate the wheels upon application of force on the hand grips; and
  a foot mechanism assembly comprising a footrest on each side of the seat assembly, the foot mechanism assembly being operably coupled to the hand mechanism assembly,
  wherein the wheelchair is configured such that a force applied to one of the hand grips causes the wheels to rotate for locomotion, and actuates the foot mechanism assembly causing the foot rest on the opposite side from the hand grip to move in an arced path, and vice versa, thereby imparting contralateral locomotion.

* * * * *